(12) United States Patent
Pollack et al.

(10) Patent No.: US 10,022,719 B2
(45) Date of Patent: Jul. 17, 2018

(54) DROPLET MANIPULATION DEVICE

(71) Applicant: Duke University, Durham, NC (US)

(72) Inventors: Michael G. Pollack, Durham, NC (US); Vamsee K. Pamula, Cary, NC (US); Richard B. Fair, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 225 days.

(21) Appl. No.: 14/935,823

(22) Filed: Nov. 9, 2015

(65) Prior Publication Data

US 2016/0114320 A1    Apr. 28, 2016

Related U.S. Application Data

(60) Continuation of application No. 14/446,733, filed on Jul. 30, 2014, now Pat. No. 9,180,450, which is a continuation of application No. 13/759,416, filed on Feb. 5, 2013, now Pat. No. 8,871,071, which is a continuation of application No. 12/494,927, filed on (Continued)

(51) Int. Cl.
| | |
|---|---|
| *G01N 27/447* | (2006.01) |
| *B01L 3/00* | (2006.01) |
| *B01F 11/00* | (2006.01) |
| *B01F 13/00* | (2006.01) |
| *G02B 26/00* | (2006.01) |
| *C25B 9/00* | (2006.01) |
| *B41J 2/14* | (2006.01) |

(52) U.S. Cl.
CPC ....... *B01L 3/50273* (2013.01); *B01F 11/0071* (2013.01); *B01F 13/0071* (2013.01); *B01F 13/0076* (2013.01); *B01F 13/0084* (2013.01); *B01L 3/00* (2013.01); *B01L 3/5027* (2013.01); *B01L 3/502784* (2013.01); *B01L 3/502792* (2013.01); *C25B 9/00* (2013.01); *G01N 27/44791* (2013.01); *G02B 26/005* (2013.01); *B01L 2200/06* (2013.01); *B01L 2200/0605* (2013.01); *B01L 2200/10* (2013.01); *B01L 2300/089* (2013.01); *B01L 2300/161* (2013.01); *B01L 2300/165* (2013.01); *B01L 2400/0415* (2013.01); *B01L 2400/0427* (2013.01); *B41J 2002/14395* (2013.01)

(58) Field of Classification Search
CPC ....... B01L 2400/0472; B01L 3/502784; B01L 3/50792
See application file for complete search history.

(56) References Cited

U.S. PATENT DOCUMENTS 6,565,727 B1 *    5/2003    Shenderov .......... B01F 13/0071
                                                                204/600

\* cited by examiner

*Primary Examiner* — Alexander S Noguerola
(74) *Attorney, Agent, or Firm* — Nexsen Pruet PLLC; E. Eric Mills

(57) ABSTRACT

Methods are provided for manipulating droplets. The methods include providing the droplet on a surface comprising an array of electrodes and a substantially co-planer array of reference elements, wherein the droplet is disposed on a first one of the electrodes, and the droplet at least partially overlaps a second one of the electrodes and an intervening one of the reference elements disposed between the first and second electrodes. The methods further include activating the first and second electrodes to spread at least a portion of the droplet across the second electrode and deactivating the first electrode to move the droplet from the first electrode to the second electrode.

46 Claims, 40 Drawing Sheets

Related U.S. Application Data

Jun. 30, 2009, now Pat. No. 8,394,249, which is a division of application No. 11/077,569, filed on Mar. 10, 2005, now Pat. No. 7,569,129, which is a division of application No. 10/253,368, filed on Sep. 24, 2002, now Pat. No. 6,911,132.

DROPLET MANIPULATION DEVICE

1 RELATED APPLICATIONS

This application is a continuation of U.S. patent application Ser. No. 14/446,733, filed Jul. 30, 2014, now U.S. Pat. No. 9,180,450, issued on Nov. 10, 2015, which is a continuation of U.S. patent application Ser. No. 13/759,416, filed Feb. 5, 2013, now U.S. Pat. No. 8,871,071, issued Oct. 28, 2014, which is a continuation of U.S. patent application Ser. No. 12/494,927, filed Jun. 30, 2009, now U.S. Pat. No. 8,394,249, issued Mar. 12, 2013, which is a divisional of U.S. patent application Ser. No. 11/077,569, filed Mar. 10, 2005, now U.S. Pat. No. 7,569,129, issued Aug. 4, 2009, which is a divisional of U.S. patent application Ser. No. 10/253,368 filed Sep. 24, 2002, now U.S. Pat. No. 6,911,132, issued Jun. 29, 2005; the disclosures of which are incorporated herein by reference in their entirety.

2 GOVERNMENT INTEREST

This invention was made with Government support under Grant No. F30602-98-2-0140 awarded by the Defense Advanced Research Projects Agency. The Government has certain rights in the invention.

3 TECHNICAL FIELD

The present invention is generally related to the field of droplet-based liquid handling and processing, such as droplet-based sample preparation, mixing, and dilution on a microfluidic scale. More specifically, the present invention relates to the manipulation of droplets by electrowetting-based techniques.

4 BACKGROUND ART

Microfluidic systems are presently being explored for their potential to carry out certain processing techniques on capillary-sized continuous flows of liquid. In particular, there is currently great interest in developing microfluidic devices commonly referred to as "chemistry-on-a-chip" sensors and analyzers, which are also known as labs-on-a-chip (LoC) and micro total analysis systems (µ-TAS). The ultimate goal of research in this field is to reduce most common (bio)chemical laboratory procedures and equipment to miniaturized, automated chip-based formats, thereby enabling rapid, portable, inexpensive, and reliable (bio)chemical instrumentation. Applications include medical diagnostics, environmental monitoring, and basic scientific research.

On-line monitoring of continuous flows is most often accomplished by connecting the output of the continuous-flow to the input of a large analysis instrument such as a HPLC (high pressure liquid chromatography), CE (capillary electrophoresis) or MS (mass spectrometry) system, with appropriate flow control and valving for sample collection and injection. Microfluidic systems for continuous monitoring typically employ miniaturized analyte-specific biosensors where the continuous-flow stream passes over or through a series of the biosensors. Because the sensors lie in a common channel, crosstalk or contamination between sensors is often a concern. In analyses where a reagent must be mixed with the flow, only one analyte can be measured at a time unless the flow is divided into parallel streams with separate means for adding the reagent, controlling and mixing the flow and carrying out detection in each stream. Additionally, mixing in microfluidic flows is usually quite challenging. Sufficient time and distance must be provided for mixing, which places constraints on chip design and system flow rates.

In general, mixing is a fundamental process in chemical analysis and biological applications. Mixing in microfluidic devices is a critical step in realizing a µTAS (micro total analysis system) or "lab on a chip" system. In accordance with the present invention described hereinbelow, it is posited that mixing in these systems could be used for pre-processing sample dilution or for reactions between sample and reagents in particular ratios. It is further posited that the ability to mix liquids rapidly while utilizing minimum chip area would greatly improve the throughput of such systems. The improved mixing would rely on two principles: the ability to either create turbulent, nonreversible flow at such small scales or create multilaminates to enhance mixing via diffusion.

Mixers can be broadly categorized into continuous-flow and droplet-based architectures. A common limitation among all continuous-flow systems is that fluid transport is physically confined to permanently etched structures, and additional mechanisms are required to enhance mixing. The transport mechanisms used are usually pressure-driven by external pumps or electrokinetically-driven by high-voltage supplies. This in turn requires the use of valves and complex channeling, consuming valuable real estate on a chip. These restrictions prevent the continuous-flow micro-mixer from becoming a truly self-contained, reconfigurable lab-on-a-chip. Whereas conventional continuous-flow systems rely on a continuous liquid flow in a confined channel, droplet-based systems utilize discrete volumes of liquid. Both the continuous-flow and droplet-based architectures can be further classified into passive and active mixers. In passive mixers, mixing is mediated through diffusion passively without any external energy inputted for the process. Active mixing, on the other hand, takes advantage of external energy, through actuation of some sort, to create either dispersed multilaminates or turbulence. In the microscopic world, effective mixing is a technical problem because it is difficult to generate turbulent flow by mechanical actuation. The inertial forces that produce turbulence and the resulting large interfacial surface areas necessary to promote mixing are absent. Thus, mixing that depends on diffusion through limited interfacial areas is a limitation.

Recently, active mixing by acoustic wave (see Vivek et al., "Novel acoustic micromixer", MEMS 2000 p. 668-73); ultrasound (see Yang et al., "Ultrasonic micromixer for microfluidic systems", MEMS 2000, p. 80); and a piezo-electrically driven, valveless micropump (see Yang et al., "Micromixer incorporated with piezoelectrically driven valveless micropump", Micro Total Analysis System '98, p. 177-180) have been proposed, and their effectiveness has been demonstrated. Mixing by electroosmotic flow has also been described in U.S. Pat. No. 6,086,243 to Paul et al. Another mixing technique has been recently presented by employing chaotic advection for mixing. See Lee et al., "Chaotic mixing in electrically and pressure driven microflows", The 14$^{th}$ IEEE workshop on MEMS 2001, p. 483-485; Liu et al., "Passive Mixing in a Three-Dimensional Serpentine Microchannel", J. of MEMS. Vol 9 (No. 2), p. 190-197 (June 2000); and Evans et al., "Planar laminar mixer", Proc. of IEEE, The tenth annual workshop on Micro Electro Mechanical Systems (MEMS 97), p. 96-101 (1997). Lee et al. focus on employing dielectrophoretic forces or pressure to generate chaotic advection, while Liu et al. rely on the geometry of a microchannel to induce the similar advection. Evans et al. constructed a planar mixing chamber on the side of which an asymmetrical source and sink generate a flow field, whereby small differences in a fluid particle's initial location leads to large differences in its final location. This causes chaotic rearrangement of fluid particles, and thus the mixing two liquids. Most recently, a technique has been proposed that uses electrohydrodynamic convection for active mixing. See Jin et al., "An active micro mixer using electrohydrodynamic (EHD) convection for microfluidic-based biochemical analysis", Technical Digest, Solid-State Sensor and Actuator Workshop, p. 52-55).

Molecular diffusion plays an important role in small Reynolds number liquid flow. In general, diffusion speed increases with the increase of the contact surface between two liquids. The time required for molecular diffusion increases in proposition to the square of the diffusion distance. A fast diffusion mixer consisting of a simple narrowing of a mixing channel has been demonstrated by Veenstra et al., "Characterization method for a new diffusion mixer applicable in micro flow injection analysis systems", J. Micromech. Microeng., Vol. 9, pg. 199-202 (1999). The primary approach for diffusion-based micromixing has been to increase the interfacial area and to decrease the diffusion length by interleaving two liquids. Interleaving is done by manipulating the structure's geometry. One approach is to inject one liquid into another through a micro nozzle array. See Miyake et al., "Micro mixer with fast diffusion", Proceedings of Micro Electro Mechanical Systems, p. 248-253 (1993). An alternative method is to stack two flow streams in one channel as thin layers by multiple stage splitting and recombining. See Branebjerg et al., "Fast mixing by lamination", Proc. IEEE Micro Electro Mechanical Systems, p. 441 (1996); Krog et al., "Experiments and simulations on a micro-mixer fabricated using a planar silicon/glass technology", MEMS, p. 177-182 (1998); Schwesinger et al., "A modular microfluidic system with an integrated micro-mixer", J. Micromech. Microeng., Vol 6, pg. 99-102 (1996); and Schwesinger et al., "A static micromixer built up in silicon", Proceedings of the SPIE, The International Society for Optical Engineering, Micromachined Devices and Components, Vol. 2642, p. 150-155. The characterizations of this type of mixer are provided by Koch et al., "Two simple micromixers based on silicon", J. Micromech. Microeng., Vol 8, p. 123-126 (1998); Koch et al., "Micromachined chemical reaction system", Sensors and Actuators, Physical (74), p. 207-210; and Koch et al., "Improved characterization technique for micromixer", J. Micromech. Microeng, Vol 9, p. 156-158 (1999). A variation of the lamination technique is achieved similarly by fractionation, re-arrangement, and subsequent reunification of liquids in sinusoidally shaped fluid channels (see Kamper et al., "Microfluidic components for biological and chemical microreactors", MEMS 1997, p. 338); in alternative channels of two counter current liquids (see http://www.imm-mainz.de/Lnews/Lnews_4/mire.html); or in a 3D pipe with a series of stationary rigid elements forming intersecting channels inside (see Bertsch et al., "3D micromixers-downscaling large scale industrial static mixers", MEMS 2001 14$^{th}$ International Conference on Micro Electro Mechanical Systems, p. 507-510). One disadvantage of purely diffusion-based static mixing is the requirement of a complex 3D structure in order to provide out-of-plane fluid flow. Another disadvantage is the low Reynolds number characterizing the flow, which results in a long mixing time.

A problem for active mixers is that energy absorption during the mixing process makes them inapplicable to temperature-sensitive fluids. Moreover, some active mixers rely on the charged or polarizable fluid particles to generate convection and local turbulence. Thus, liquids with low conductivity could not be properly mixed. When the perturbation force comes from a mechanical micropump, however, the presence of the valveless micropump makes the control of flow ratios of solutions for mixing quite complex.

In continuous flow systems, the control of the mixing ratio is always a technical problem. By varying the sample and reagent flow rates, the mixing ratio can be obtained with proper control of the pressure at the reagent and sample ports. However, the dependence of pressure on the properties of the fluid and the geometry of the mixing chamber/channels makes the control very complicated. When inlets are controlled by a micropump, the nonlinear relationship between the operating frequency and flow rate make it a nontrivial task to change the flow rate freely. The discontinuous mixing of two liquids by integration of a mixer and an electrically actuated flapper valve has been demonstrated by Voldman et al., "An Integrated Liquid Mixer/Valve", Journal of Microelectromechanical Systems", Vol. 9, No. 3 (September 2000). The design required a sophisticated pressure-flow calibration to get a range of mixing ratios.

Droplet-based mixers have been explored by Hosokawa et al., "Droplet based nano/picoliter mixer using hydrophobic microcapillary vent", MEMS '99, p. 388; Hosokawa et al., "Handling of Picoliter Liquid Samples in a Poly(dimethylsiloxane)-Based Microfluidic Device", Anal. Chem 1999. Vol. 71, p. 4781-4785; Washizu et al., Electrostatic actuation of liquid droplets for micro-reactor applications, IEEE Transactions on Industry Applications, Vol. 34 (No. 4), p. 732-737 (1998); Burns et al., "An Integrated Nanoliter DNA Analysis Device", Science, Vol. 282 (No. 5388), p. 484 (Oct. 16, 1998); Pollack et al., "Electrowetting-based actuation of liquid droplets for microfluidic applications", Appl. Phys. Lett., Vol. 77, p. 1725 (September 2000); Pamula et al., "Microfluidic electrowetting-based droplet mixing", MEMS Conference, 2001, 8-10; Fowler et al., "Enhancement of Mixing by Droplet-based Microfluidics", IEEE MEMS Proceedings, 2002, 97-100; Pollack, "Electrowetting-based microactuation of droplets for digital microfluidics", Ph.D. Thesis, Department of Electrical and Computer Engineering, Duke University; and Wu, "Design and Fabrication of an Input Buffer for a Unit Flow Microfluidic System", Master thesis, Department of Electrical and Computer Engineering, Duke University.

It is believed that droplet-based mixers can be designed and constructed to provide a number of advantages over continuous-flow-based microfluidic devices. Discrete flow can eliminate the limitation on flow rate imposed by continuous microfluidic devices. The design of droplet-based mixing devices can be based on a planar structure that can be fabricated at low cost. Actuation mechanisms based on pneumatic drive, electrostatic force, or electrowetting do not require heaters, and thus have a minimum effect on (bio) chemistry. By providing a proper droplet generation technique, droplet-based mixers can provide better control of liquid volume. Finally, droplet-based mixers can enable droplet operations such as shuttling or shaking to generate internal recirculation within the droplet, thereby increasing mixing efficiency in the diffusion-dominated scale.

In view of the foregoing, it would be advantageous to provide novel droplet-manipulative techniques to address the problems associated with previous analytical and mixing techniques that required continuous flows. In particular, the present invention as described and claimed hereinbelow developed in part from the realization that an alternative and better solution to the continuous flow architecture would be to design a system where the channels and mixing chambers are not permanently etched, but rather are virtual and can be configured and reconfigured on the fly. The present invention enables such a system by providing means for discretizing fluids into droplets and means for independently controlling individual droplets, allowing each droplet to act as a virtual mixing or reaction chamber.

5 DISCLOSURE OF THE INVENTION

The present invention provides droplet-based liquid handling and manipulation methods by implementing electrowetting-based techniques. The droplets can be sub-microliter-sized, and can be moved freely by controlling voltages to electrodes. Generally, the actuation mechanism of the droplet is based upon surface tension gradients induced in the droplet by the voltage-induced electrowetting effect. The mechanisms of the invention allow the droplets to be transported while also acting as virtual chambers for mixing to be performed anywhere on a chip. The chip can include an array of electrodes that are reconfigurable in real-time to perform desired tasks. The invention enables several different types of handling and manipulation tasks to be performed on independently controllable droplet samples, reagents, diluents, and the like. Such tasks conventionally have been performed on continuous liquid flows. These tasks include, for example, actuation or movement, monitoring, detection, irradiation, incubation, reaction, dilution, mixing, dialysis, analysis, and the like. Moreover, the methods of the invention can be used to form droplets from a continuous-flow liquid source, such as a from a continuous input provided at a microfluidic chip. Accordingly, the invention provides a method for continuous sampling by discretizing or fragmenting a continuous flow into a desired number of uniformly sized, independently controllable droplet units.

The partitioning of liquids into discrete, independently controlled packets or droplets for microscopic manipulation provides several important advantages over continuous-flow systems. For instance, the reduction of fluid manipulation, or fluidics, to a set of basic, repeatable operations (for example, moving one unit of liquid one unit step) allows a hierarchical and cell-based design approach that is analogous to digital electronics.

In addition to the advantages identified hereinabove, the present invention utilizes electrowetting as the mechanism for droplet actuation or manipulation for the following additional advantages:

1. Improved control of a droplet's position.
2. High parallelism capability with a dense electrode array layout.
3. Reconfigurability.
4. Mixing-ratio control using programming operations, yielding better controllability and higher accuracy in mixing ratios.
5. High throughput capability, providing enhanced parallelism.
6. Enabling of integration with optical detection that can provide further enhancement on asynchronous controllability and accuracy.

In particular, the present invention provides a sampling method that enables droplet-based sample preparation and analysis. The present invention fragments or discretizes the continuous liquid flow into a series of droplets of uniform size on or in a microfluidic chip or other suitable structure by inducing and controlling electrowetting phenomena. The liquid is subsequently conveyed through or across the structure as a train of droplets which are eventually recombined for continuous-flow at an output, deposited in a collection reservoir, or diverted from the flow channel for analysis. Alternatively, the continuous-flow stream may completely traverse the structure, with droplets removed or sampled from specific locations along the continuous flow for analysis. In both cases, the sampled droplets can then be transported to particular areas of the structure for analysis. Thus, the analysis is carried out on-line, but not in-line with respect to the main flow, allowing the analysis to be decoupled from the main flow.

Once removed from the main flow, a facility exists for independently controlling the motion of each droplet. For purposes of chemical analysis, the sample droplets can be combined and mixed with droplets containing specific chemical reagents formed from reagent reservoirs on or adjacent to the chip or other structure. Multiple-step reactions or dilutions might be necessary in some cases with portions of the chip assigned to certain functions such as mixing, reacting or incubation of droplets. Once the sample is prepared, it can be transported by electrowetting to another portion of the chip dedicated to detection or measurement of the analyte. Some detection sites can, for example, contain bound enzymes or other biomolecular recognition agents, and be specific for particular analytes while others can consist of a general means of detection such as an optical system for fluorescence or absorbance based assays. The flow of droplets from the continuous flow source to the analysis portion of the chip (the analysis flow) is controlled independently of the continuous flow (the input flow), allowing a great deal of flexibility in carrying out the analyses. Other features and advantages of the methods of the present invention are described in more detail hereinbelow.

Methods of the present invention use means for forming microdroplets from the continuous flow and for independently transporting, merging, mixing, and other processing of the droplets. The preferred embodiment uses electrical control of surface tension (i.e., electrowetting) to accomplish these manipulations. In one embodiment, the liquid is contained within a space between two parallel plates. One plate contains etched drive electrodes on its surface while the other plate contains either etched electrodes or a single, continuous plane electrode that is grounded or set to a reference potential. Hydrophobic insulation covers the electrodes and an electric field is generated between electrodes on opposing plates. This electric field creates a surface-tension gradient that causes a droplet overlapping the energized electrode to move towards that electrode. Through proper arrangement and control of the electrodes, a droplet can be transported by successively transferring it between adjacent electrodes. The patterned electrodes can be arranged in a two dimensional array so as to allow transport of a droplet to any location covered by that array. The space surrounding the droplets may be filled with a gas such as air or an immiscible fluid such as oil.

In another embodiment, the structure used for ground or reference potential is co-planar with the drive electrodes and the second plate, if used, merely defines the containment space. The co-planar grounding elements can be a conductive grid superimposed on the electrode array. Alternatively, the grounding elements can be electrodes of the array dynamically selected to serve as ground or reference electrodes while other electrodes of the array are selected to serve as drive electrodes.

Droplets can be combined together by transporting them simultaneously onto the same electrode. Droplets are subsequently mixed either passively or actively. Droplets are mixed passively by diffusion. Droplets are mixed actively by moving or "shaking" the combined droplet by taking advantage of the electrowetting phenomenon. In a preferred embodiment, droplets are mixed by rotating them around a two-by-two array of electrodes. The actuation of the droplet creates turbulent non-reversible flow, or creates dispersed multilaminates to enhance mixing via diffusion. Droplets can be split off from a larger droplet or continuous body of liquid in the following manner: at least two electrodes adjacent to the edge of the liquid body are energized along with an electrode directly beneath the liquid, and the liquid moves so as to spread across the extent of the energized electrodes. The intermediate electrode is then de-energized to create a hydrophobic region between two effectively hydrophilic regions. The liquid meniscus breaks above the hydrophobic regions, thus forming a new droplet. This process can be used to form the droplets from a continuously flowing stream.

According to one embodiment of the present invention, an apparatus for manipulating droplets comprises a substrate comprising a substrate surface, an array of electrodes disposed on the substrate surface, an array of reference elements, a dielectric layer disposed on the substrate surface, and an electrode selector. The reference elements are settable to a reference potential. The array of reference elements is disposed of in substantially co-planar relation to the electrode array, such that each reference element is adjacent to at least one of the electrodes. The dielectric layer is disposed on the substrate surface and is patterned to cover the electrodes. The electrode selector can be provided as a microprocessor or other suitable component for sequentially activating and de-activating one or more selected electrodes of the array to sequentially bias the selected electrodes to an actuation voltage. The sequencing performed by the electrode selector enables a droplet disposed on the substrate surface to move along a desired path that is defined by the selected electrodes.

According to one method of the present invention, a droplet is actuated by providing the droplet on a surface that comprises an array of electrodes and a substantially co-planar array of reference elements. The droplet is disposed on a first one of the electrodes, and at least partially overlaps a second one of the electrodes and an intervening one of the reference elements disposed between the first and second electrodes. The first and second electrodes are activated to spread at least a portion of the droplet across the second electrode. The first electrode is de-activated to move the droplet from the first electrode to the second electrode.

According to one aspect of this method, the second electrode is adjacent to the first electrode along a first direction. In addition, the electrode array comprises one more additional electrodes adjacent to the first electrode along one or more additional directions. The droplet at least partially overlaps these additional electrodes as well as the second electrode. In accordance with this aspect of the method, the first direction that includes the first electrode and the second electrode is selected as a desired direction along which the droplet is to move. The second electrode is selected for activation based on the selection of the first direction.

In accordance with another method of the present invention, a droplet is split into two or more droplets. A starting droplet is provided on a surface comprising an array of electrodes and a substantially co-planar array of reference elements. The electrode array comprises at least three electrodes comprising a first outer electrode, a medial electrode adjacent to the first outer electrode, and a second outer electrode adjacent to the medial electrode. The starting droplet is initially disposed on at least one of these three electrodes, and at least partially overlaps at least one other of the three electrodes. Each of the three electrodes is activated to spread the starting droplet across the three electrodes. The medial electrode is de-activated to split the starting droplet into first and second split droplets. The first split droplet is disposed on the first outer electrode and the second split droplet is disposed on the second outer electrode.

In yet another method of the present invention, two or more droplets are merged into one droplet. First and second droplets are provided on a surface comprising an array of electrodes in a substantially co-planar array of reference elements. The electrode array comprises at least three electrodes comprising a first outer electrode, a medial electrode adjacent to the first outer electrode, and a second outer electrode adjacent to the medial electrode. The first droplet is disposed on the first outer electrode and at least partially overlaps the medial electrode. The second droplet is disposed on the second outer electrode and at least partially overlaps the medial electrode. One of the three electrodes is selected as a destination electrode. Two or more of the three electrodes are selected for sequential activation and de-activation, based on the selection of the destination electrode. The electrodes selected for sequencing are sequentially activated and de-activated to move one of the first and second droplets toward the other droplet, or both of the first and second droplets toward each other. The first and second droplets merge together to form a combined droplet on the destination electrode.

According to one aspect of this method, the first droplet comprises a first composition, the second droplet comprises a second composition, and the combined droplet comprises both the first and second compositions. The method further comprises the step of mixing the first and second compositions together. In accordance with the present invention, the mixing step can be passive or active. In one aspect of the invention, the mixing step comprises moving the combined droplet on a two-by-two sub-array of four electrodes by sequentially activating and de-activating the four electrodes to rotate the combined droplet. At least a portion of the combined droplet remains substantially stationary at or near an intersecting region of the four electrodes while the combined droplet rotates. In another aspect of the invention, the mixing step comprises sequentially activating and de-activating a linearly arranged set of electrodes of the electrode array to oscillate the combined droplet back and forth along the linearly arranged electrode set a desired number of times and at a desired frequency. Additional mixing strategies provided in accordance with the invention are described in detail hereinbelow.

According to another embodiment of the present invention, an apparatus for manipulating droplets comprises a substrate comprising a substrate surface, an array of electrodes disposed on the substrate surface, a dielectric layer disposed on the substrate surface and covering the electrodes, and an electrode selector. The electrode selector dynamically creates a sequence of electrode pairs. Each electrode pair comprises a selected first one of the electrodes biased to a first voltage, and a selected second one of the electrodes disposed adjacent to the selected first electrode and biased to a second voltage that is less than the first voltage. Preferably, the second voltage is a ground voltage or some other reference voltage. A droplet disposed on the substrate surface moves along a desired path that runs between the electrode pairs created by the electrode selector.

According to yet another method of the present invention, a droplet is actuated by providing the droplet on a surface comprising an array of electrodes. The droplet is initially disposed on a first one of the electrodes and at least partially overlaps a second one of the electrodes that is separated from the first electrode by a first gap. The first electrode is biased to a first voltage and the second electrode is biased to a second voltage lower than the first voltage. In this manner, the droplet becomes centered on the first gap. A third one of the electrodes that is proximate to the first and second electrodes is biased to a third voltage that is higher than the second voltage to spread the droplet onto the third electrode. The bias on the first electrode is then removed to move the droplet away from the first electrode. The droplet then becomes centered on a second gap between the second and third electrodes.

According to still another method of the present invention, a droplet is split into two or more droplets. A starting droplet is provided on a surface comprising an array of electrodes. The electrode array comprises at least three electrodes comprising a first outer electrode, a medial electrode adjacent to the first outer electrode, and a second outer electrode adjacent to the medial electrode. The starting droplet is initially disposed on at least one of the three electrodes and at least partially overlaps at least one other of the three electrodes. Each of the three electrodes is biased to a first voltage to spread the initial droplet across the three electrodes. The medial electrode is biased to a second voltage lower than the first voltage to split the initial droplet into first and second split droplets. The first split droplet is formed on the first outer electrode and the second split droplet is formed on the second outer electrode.

According to a further method of the present invention, two or more droplets are merged into one droplet. First and second droplets are provided on a surface comprising an array of electrodes. The electrode array comprises at least three electrodes comprising a first outer electrode, a medial electrode adjacent to the first outer electrode, and a second outer electrode adjacent to the medial electrode. The first droplet is disposed on the first outer electrode and at least partially overlaps the medial electrode. The second droplet is disposed on the second outer electrode and at least partially overlaps the medial electrode. One of the three electrodes is selected as a destination electrode. Two or more of the three electrodes are selected for sequential biasing based on the selection of the destination electrode. The electrodes selected for sequencing are sequentially biased between a first voltage and a second voltage to move one of the first and second droplets toward the other droplet or both of the first and second droplets toward each other. The first and second droplets merge together to form a combined droplet on the destination electrode.

The present invention also provides a method for sampling a continuous liquid flow. A liquid flow is supplied to a surface along a first flow path. The surface comprises an array of electrodes and a substantially co-planar array of reference elements. At least a portion of the liquid flow is disposed on a first one of the electrodes, and at least partially overlaps a second one of the electrodes and a reference element between the first and second electrodes. The first electrode, the second electrode, and a third one of the electrodes adjacent to second electrode are activated to spread the liquid flow portion across the second and third electrodes. The second electrode is de-activated to form a droplet from the liquid flow on the third electrode. The droplet is distinct from and in controllable independently of the liquid flow.

In accordance with another method of the present invention for sampling a continuous liquid flow, a liquid flow is supplied to a surface along a first flow path. The surface comprises an array of electrodes. At least a portion of the liquid flow is disposed on a first one of the electrodes and at least partially overlaps a second one of the electrodes. The first electrode, the second electrode, and a third one of the electrodes adjacent to the second electrode are biased to a first voltage to spread the liquid flow portion across the second and third electrodes. The second electrode is biased to a second voltage that is less than the first voltage to form a droplet from the liquid flow on the third electrode. The droplet so formed is distinct from and controllable independently of the liquid flow.

According to still another embodiment of the present invention, a binary mixing apparatus comprises a first mixing unit, a second mixing unit, and an electrode selector. The first mixing unit comprises a first surface area, an array of first electrodes disposed on the first surface area, and an array of first reference elements disposed in substantially co-planar relation to the first electrodes. The second mixing unit comprises a second surface area, an array of second electrodes disposed on the second surface area, an array of second reference elements disposed in substantially co-planar relation to the second electrodes, and a droplet outlet area communicating with the second surface area and with the first mixing unit. The electrode selector sequentially activates and de-activates one or more selected first electrodes to mix together two droplets supplied to the first surface area. The electrode selector also sequentially activates and de-activates one or more selected second electrodes to mix together two other droplets supplied to the second surface area.

It is therefore an object of the present invention to sample a continuous flow liquid input source from which uniformly sized, independently controllable droplets are formed on a continuous and automated basis.

It is another object of the present invention to utilize electrowetting technology to implement and control droplet-based manipulations such as transportation, mixing, detection, analysis, and the like.

It is yet another object of the present invention to provide an architecture suitable for efficiently performing binary mixing of droplets to obtain desired mixing ratios with a high degree of accuracy.

Some of the objects of the invention having been stated hereinabove, other objects will become evident as the description proceeds when taken in connection with the accompanying drawings as best described hereinbelow.

6 BRIEF DESCRIPTION OF THE DRAWINGS

Figure 9A:
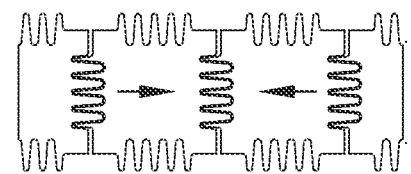
Figure 9B:
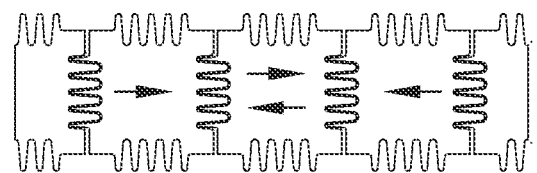
Figure 9C:
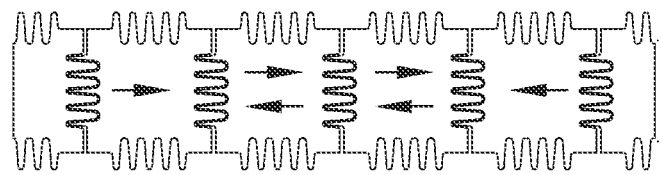
Figure 10A:
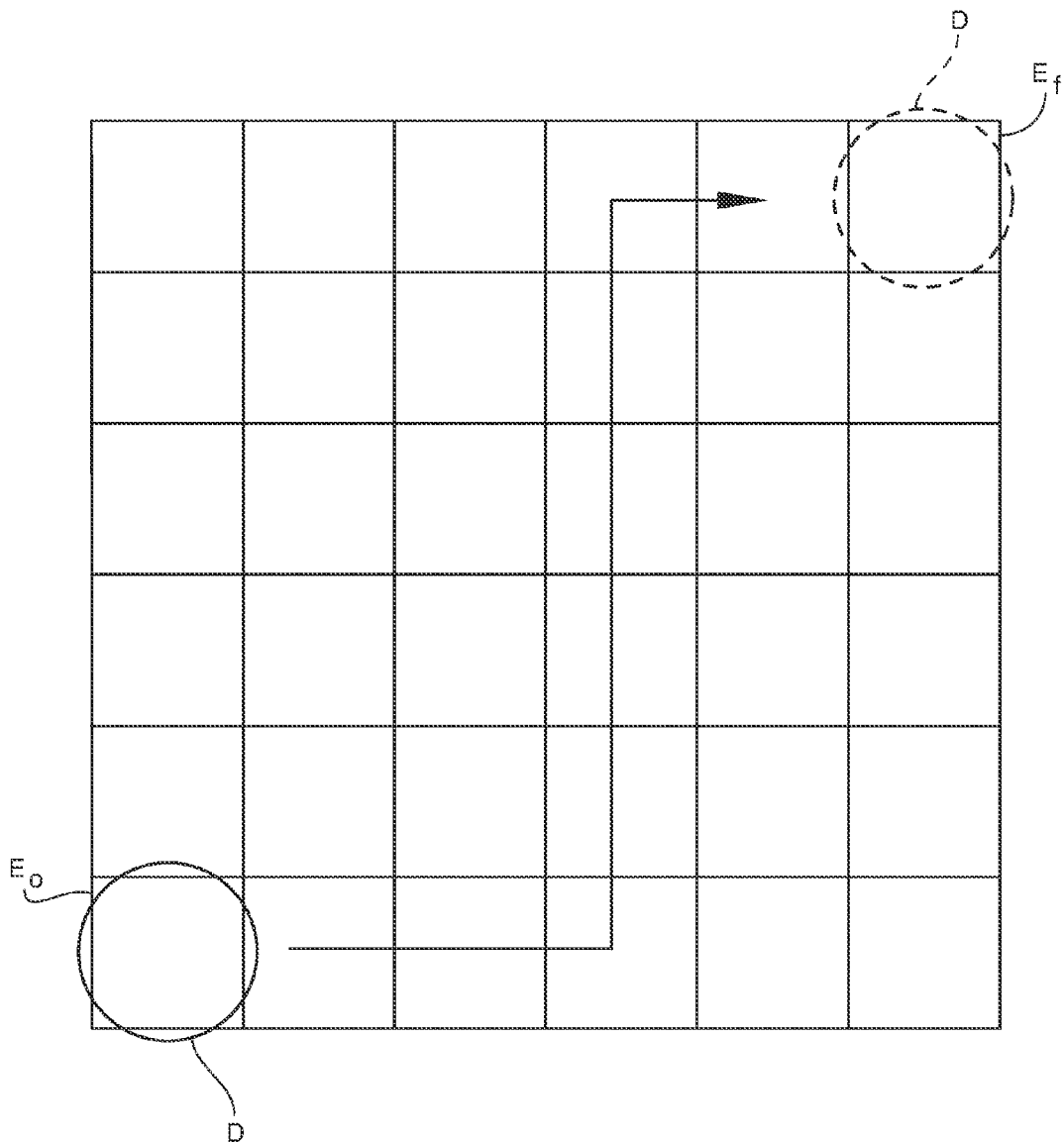
Figure 10B:
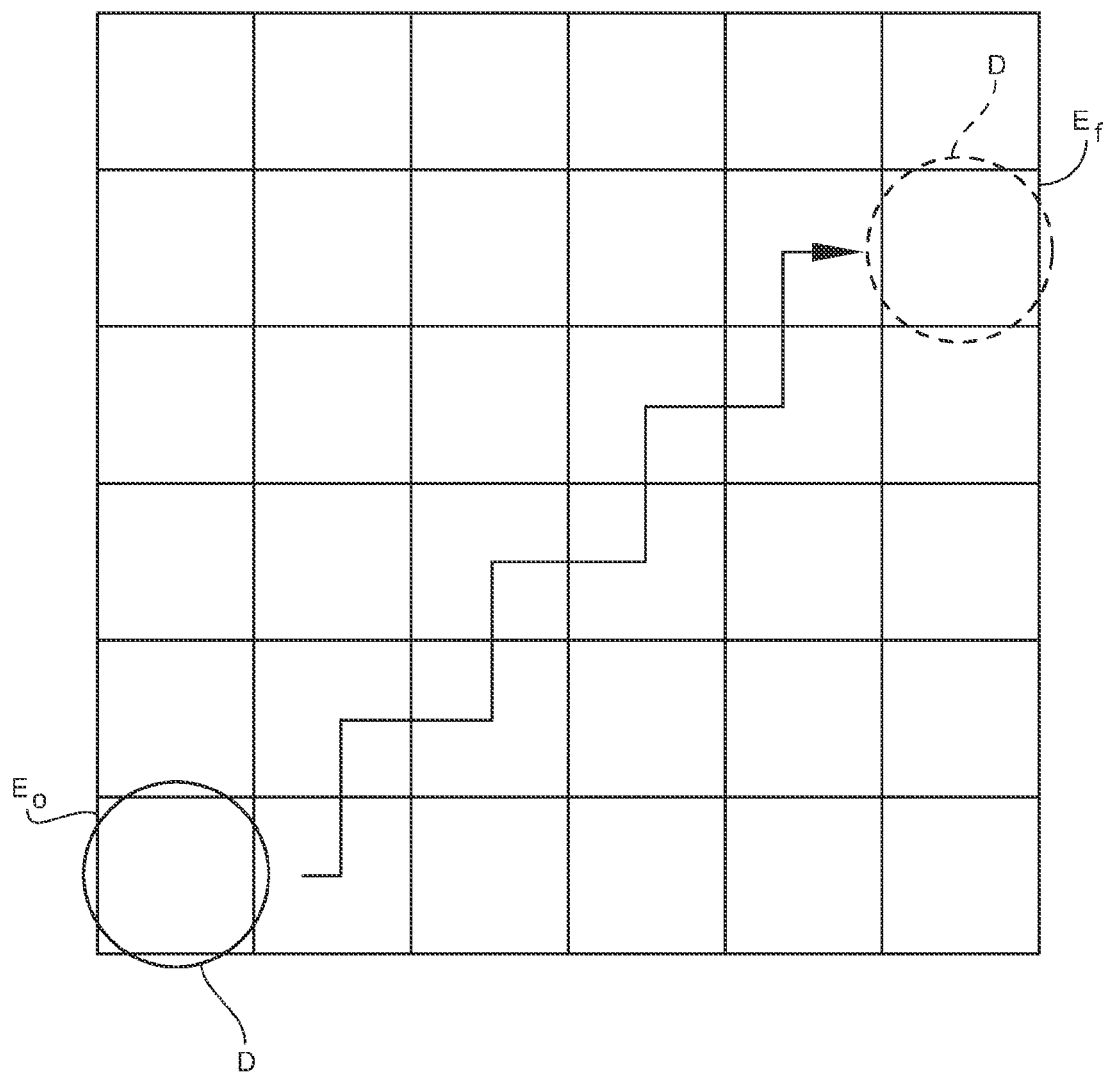
Figure 10C:
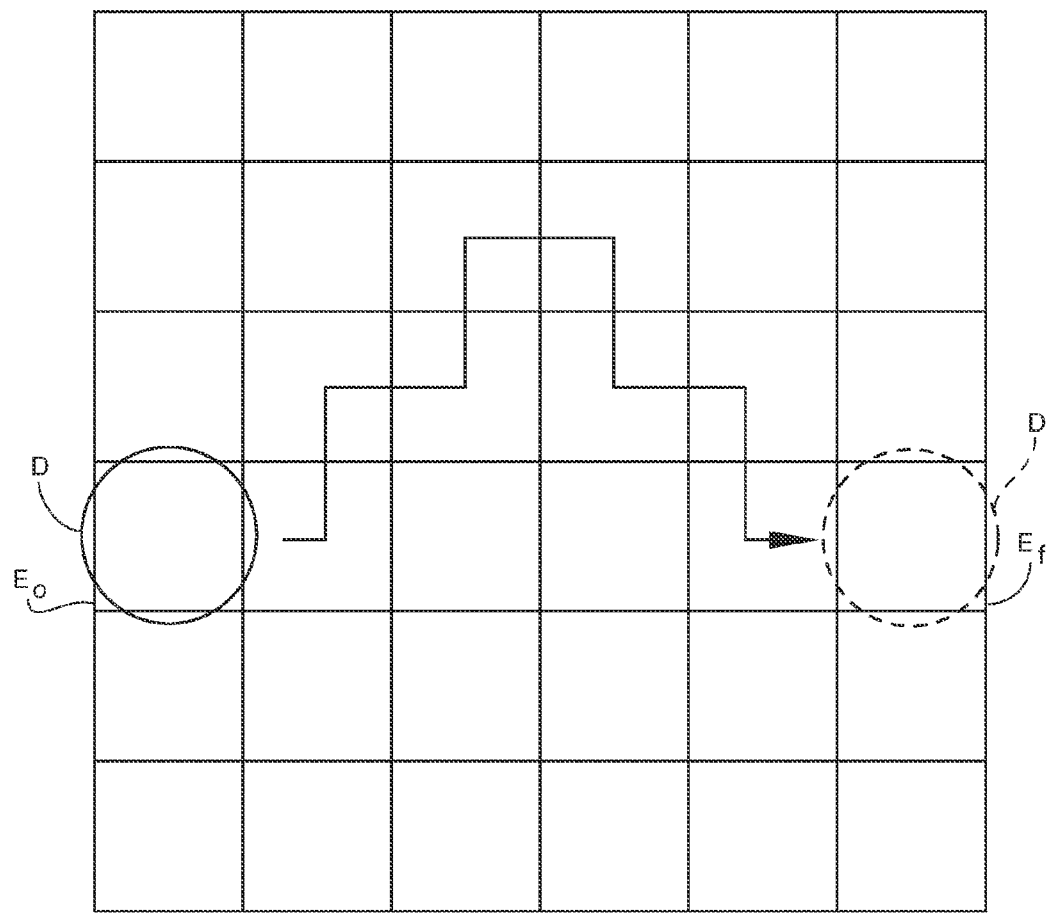
Figure 11:
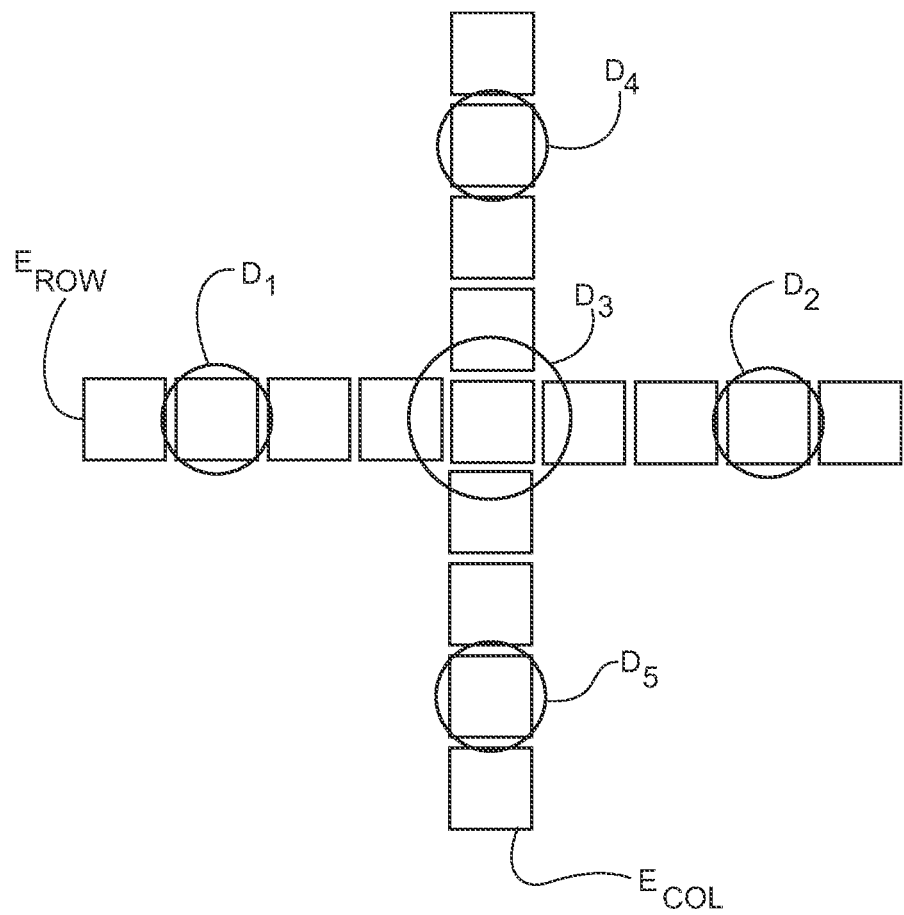
Figure 12A:
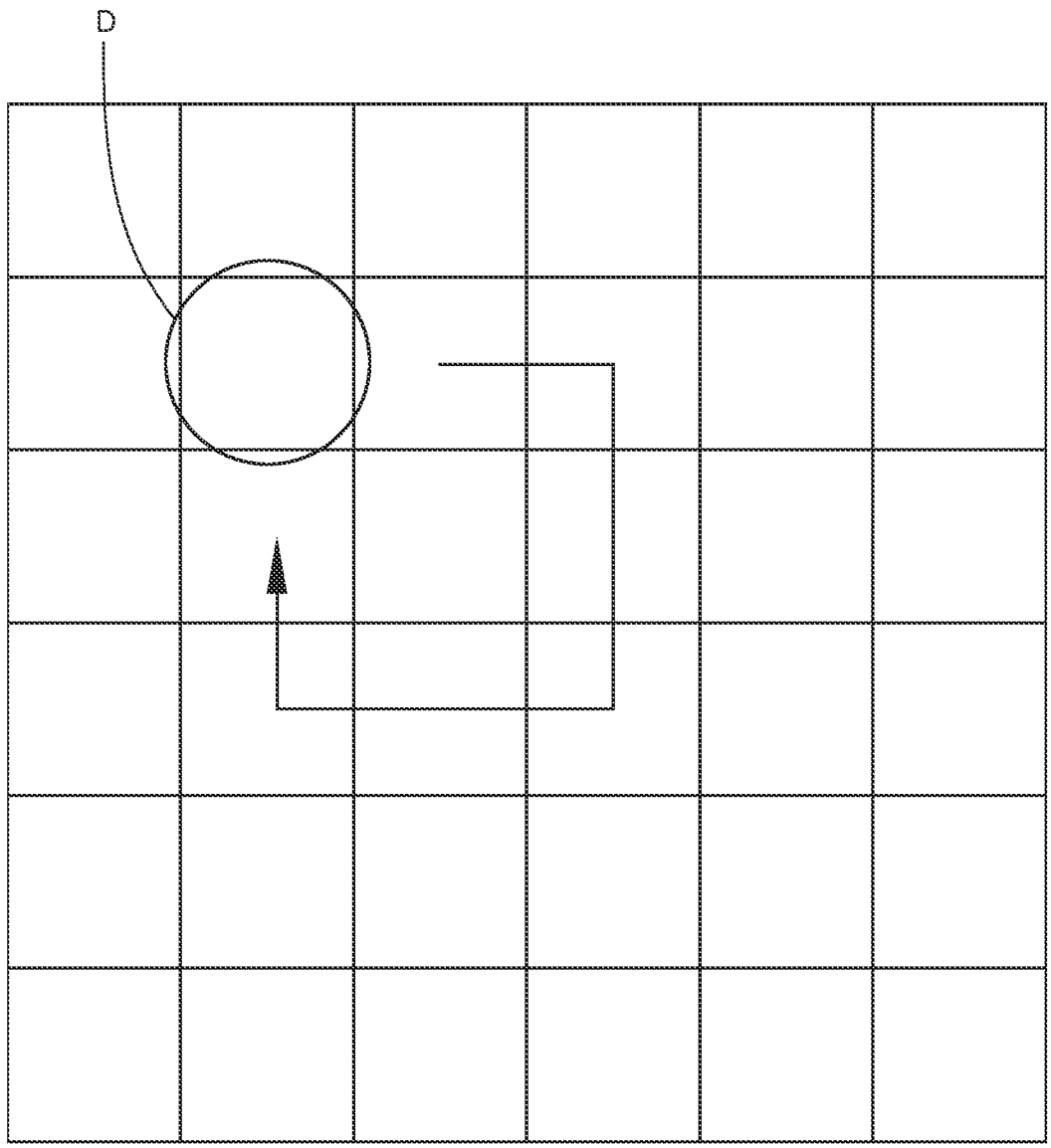
Figure 12B:
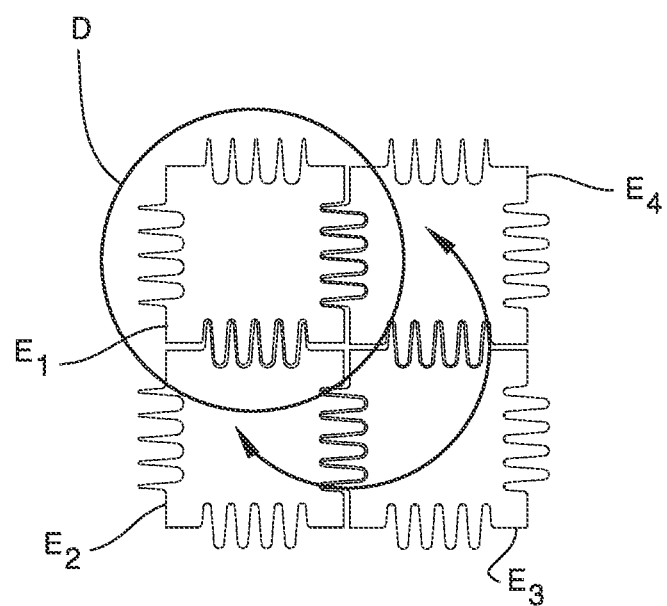
Figure 13:
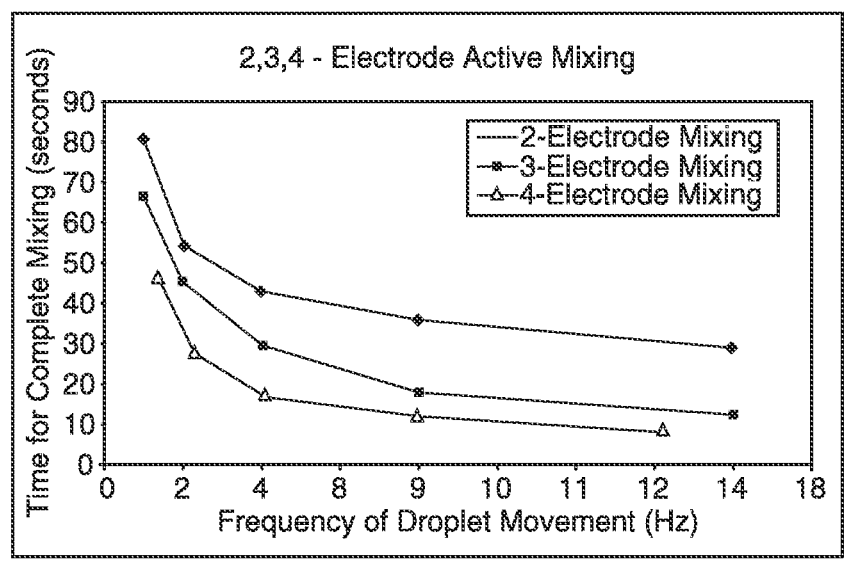
Figure 14:
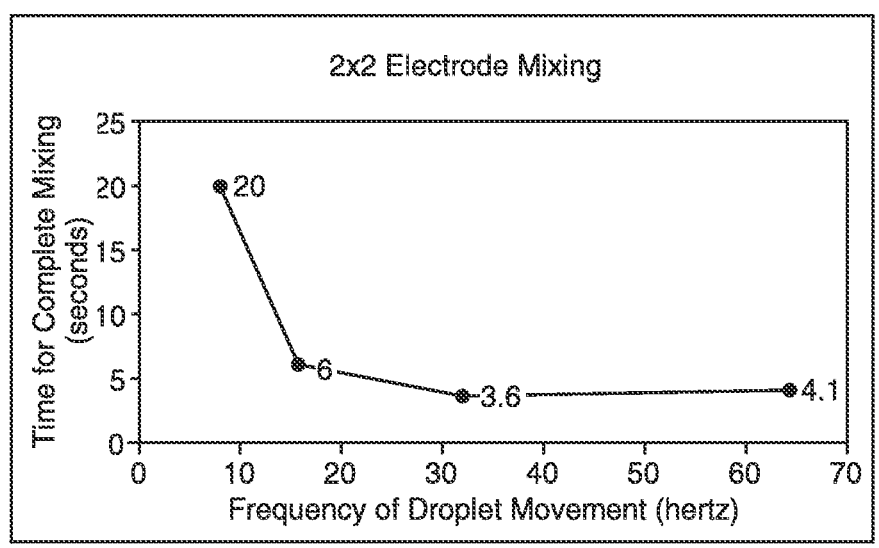
Figure 15A:
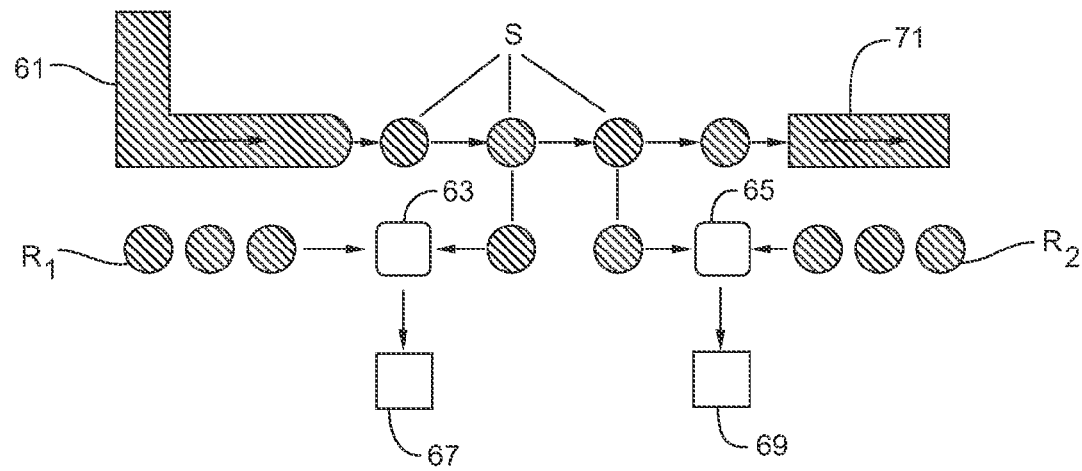
Figure 15B:
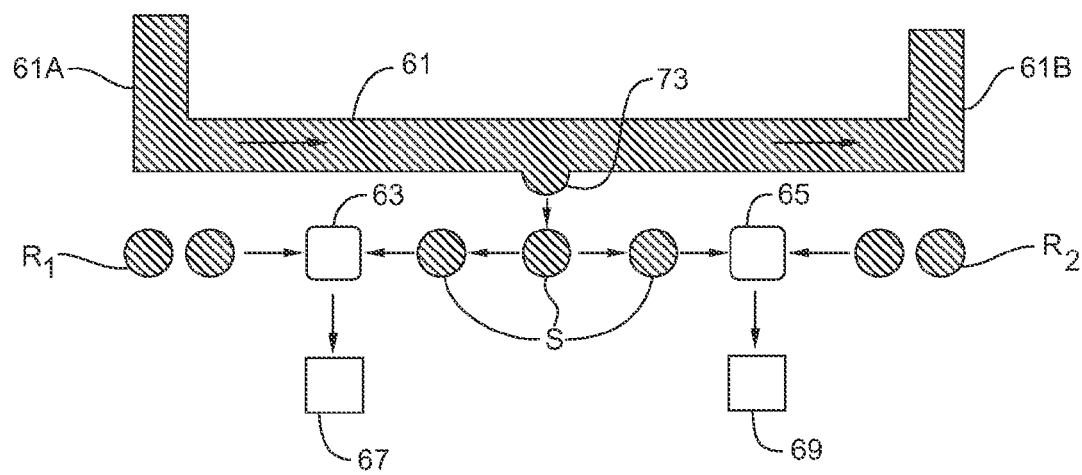
Figure 16:
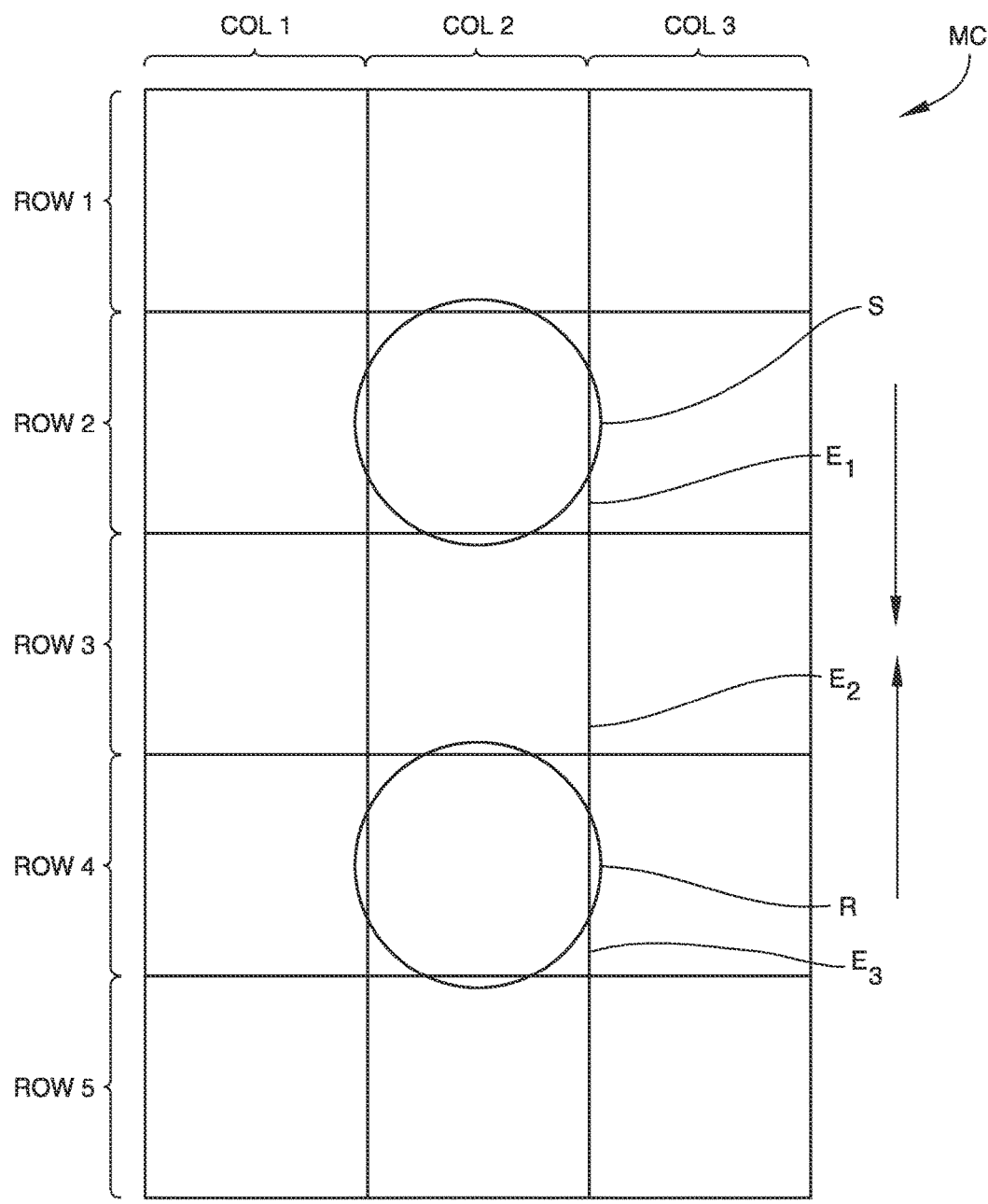
Figure 17:
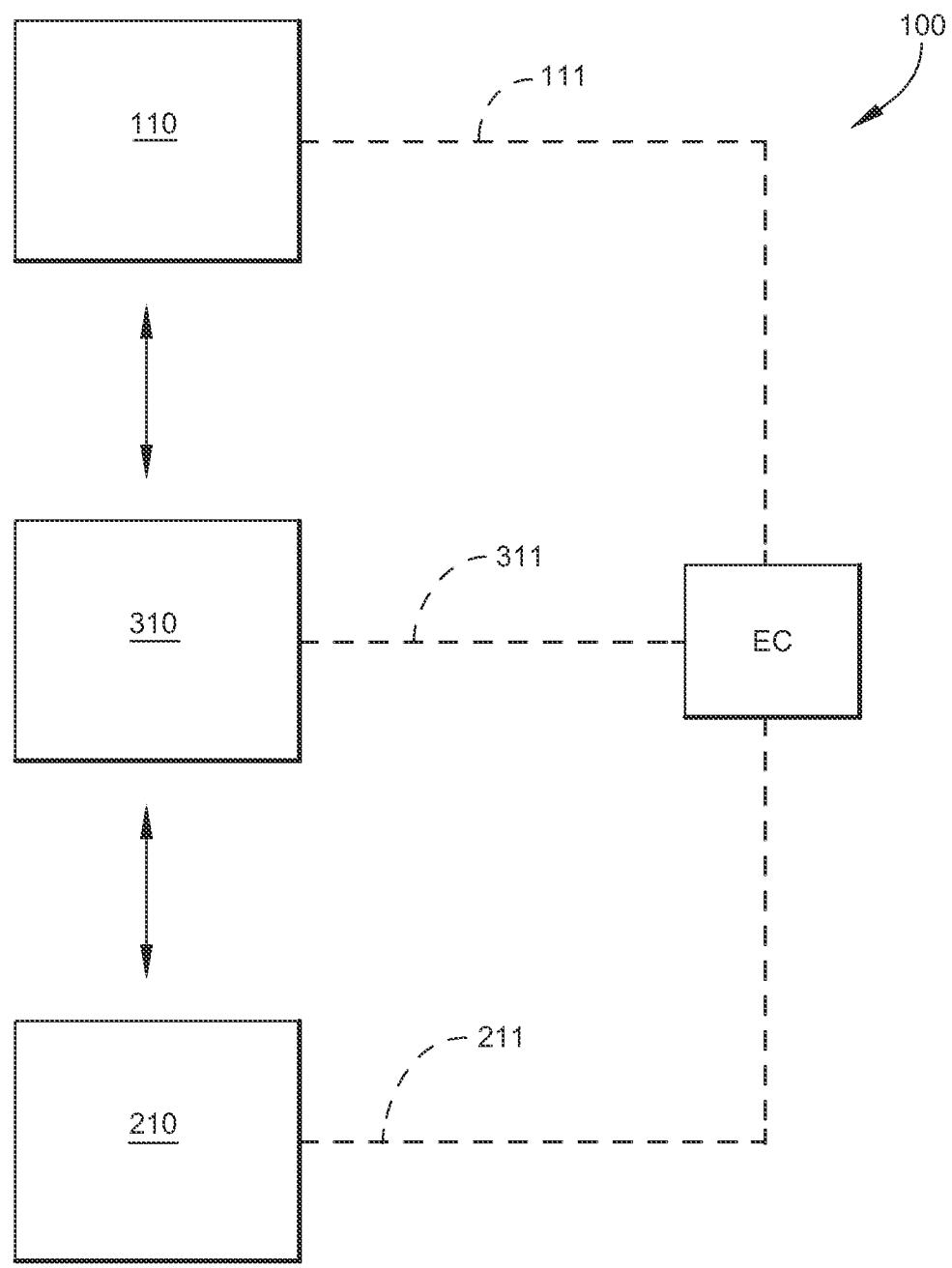
Figure 18A:
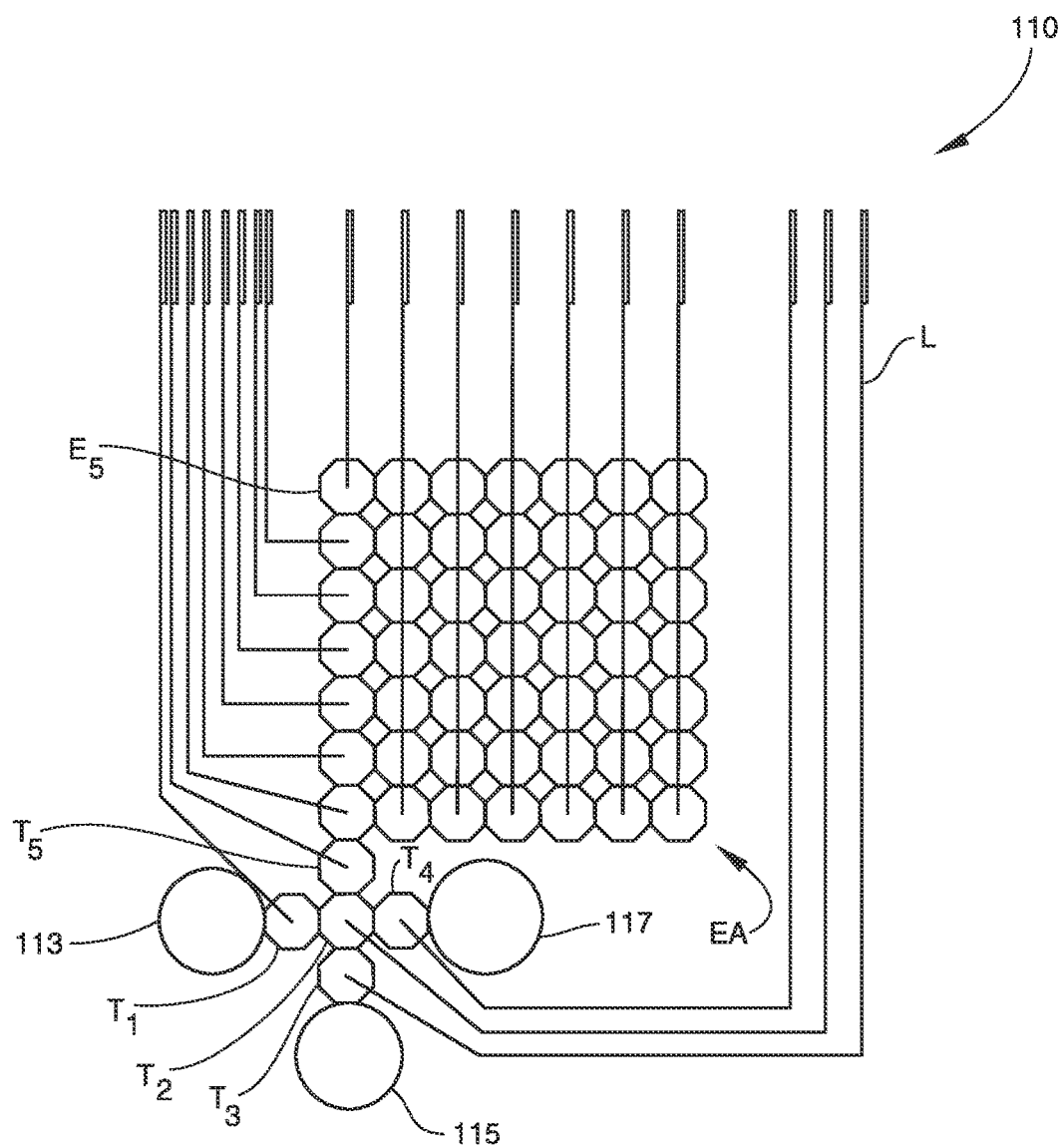
Figure 18B:
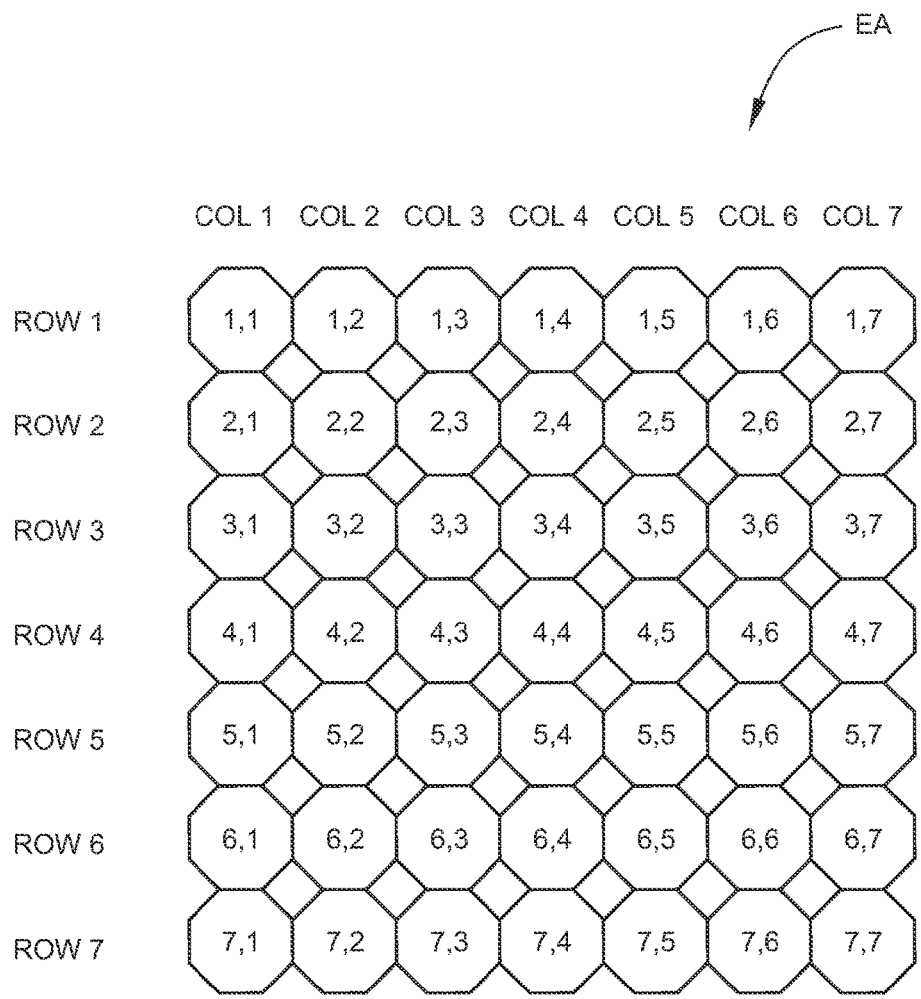
Figure 20:
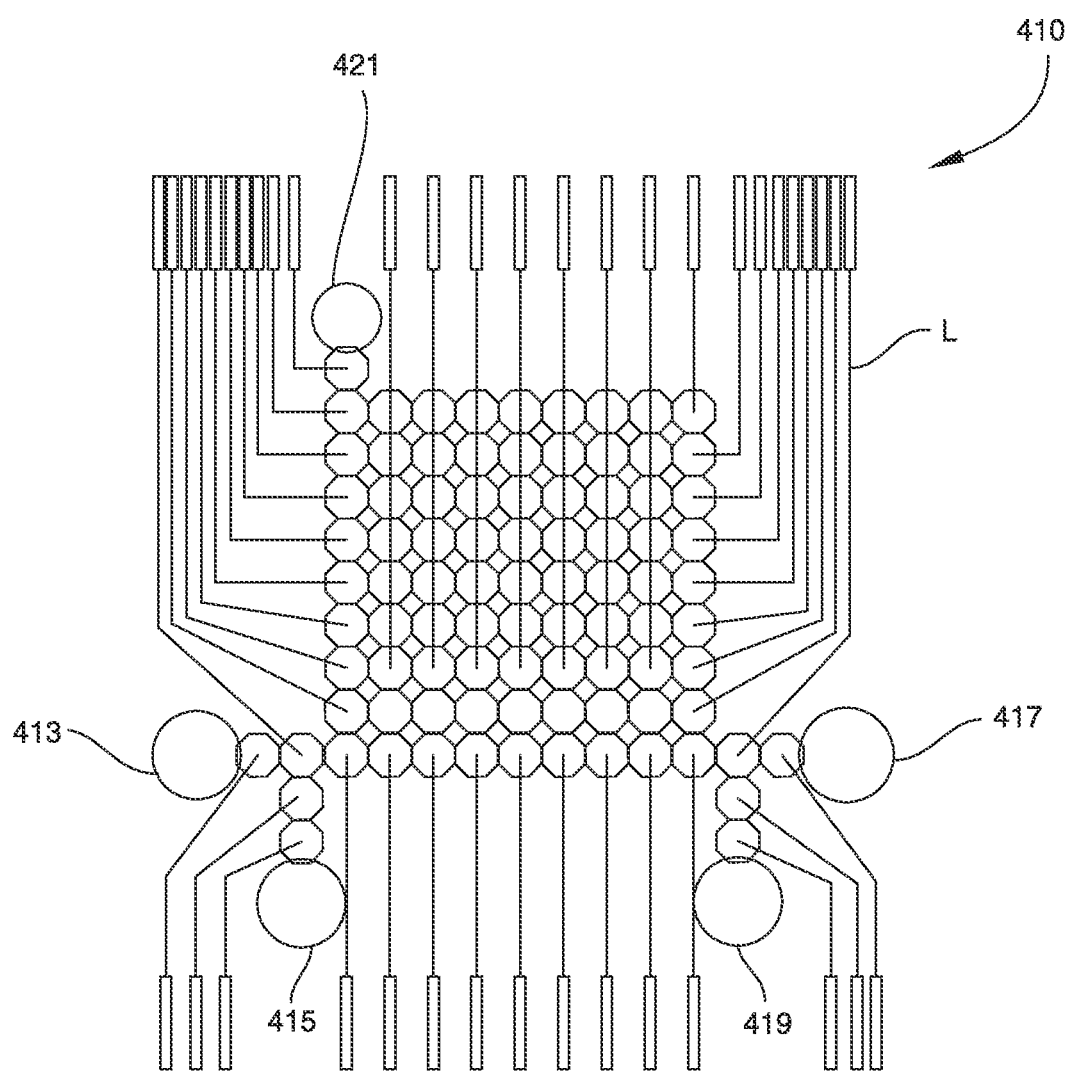
Figure 21:
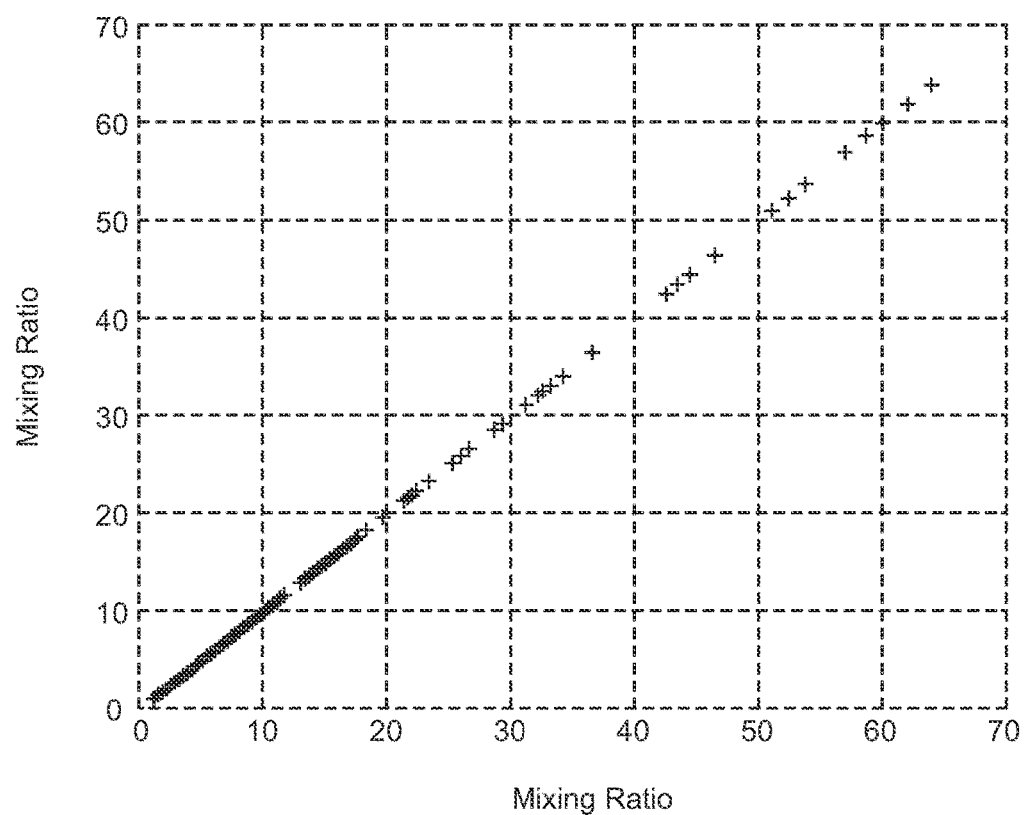
Figure 22:
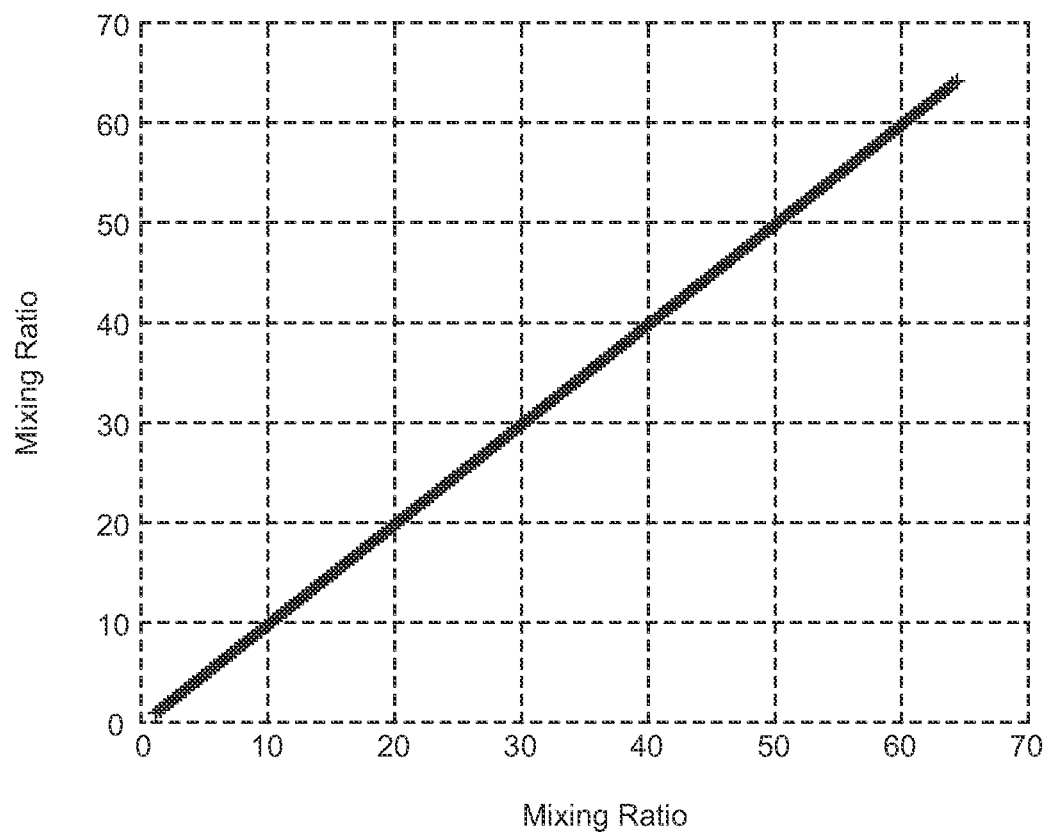

FIGS. 9A, 9B, and 9C are respective top plan views of two-, three-, and four-electrode configurations on which one-dimensional linear mixing of droplets can be performed in accordance with the present invention;

FIGS. 10A, 10B, and 10C are schematic diagrams illustrating the examples of a mixing-in-transport process enabled by the present invention;

FIG. 11 is a schematic view illustrating a two-dimensional linear mixing process enabled by the present invention;

FIG. 12A is a top plan view of an array of electrode cells on which a two-dimensional loop mixing process is performed in accordance with the present invention;

FIG. 12B is a top plan view of a 2×2 array of electrode cells on which a two-dimensional loop mixing process is performed in which a portion of the droplet remains pinned during rotation;

FIG. 13 is a plot of data characterizing the performance of active droplet mixing using the two-, three- and four-electrode configurations respectively illustrated in FIGS. 9A, 9B, and 9C;

FIG. 14 is a plot of data characterizing the performance of the 2×2 electrode configuration illustrated in FIG. 12B;

FIG. 15A is a schematic view illustrating the formation of droplets from a continuous flow source and movement of the droplets across an electrode-containing surface to process areas of the surface;

FIG. 15B is a schematic view illustrating the formation of droplets from a continuous flow that traverses an entire electrode-containing surface or section thereof;

FIG. 16 is a top plan view of a droplet-to-droplet mixing unit that can be defined on an electrode array on a real-time basis;

FIG. 17 is a schematic view of a binary mixing apparatus provided in accordance with the present invention;

FIG. 18A is a schematic view of the architecture of a binary mixing unit capable of one-phase mixing according to the present invention;

FIG. 18B is a schematic sectional view of the binary mixing unit illustrated in FIG. 18A, showing details of the matrix section thereof where binary mixing operations occur;

FIGS. 19A-19F are sequential schematic views of an electrode array or section thereof provided by a binary mixing unit of the present invention, showing an exemplary process for performing binary mixing operations to obtain droplets having a predetermined, desired mixing ratio;

FIG. 20 is a schematic view illustrating the architecture for a binary mixing unit capable of two-phase mixing in accordance with the present invention;

FIG. 21 is a plot of mixing points of a one- and two-phase mixing plan enabled by the binary mixing architecture of the present invention; and FIG. 22 is a plot of mixing points of a one-, two- and three-phase mixing plan enabled by the binary mixing architecture of the present invention.

Figure 23A:
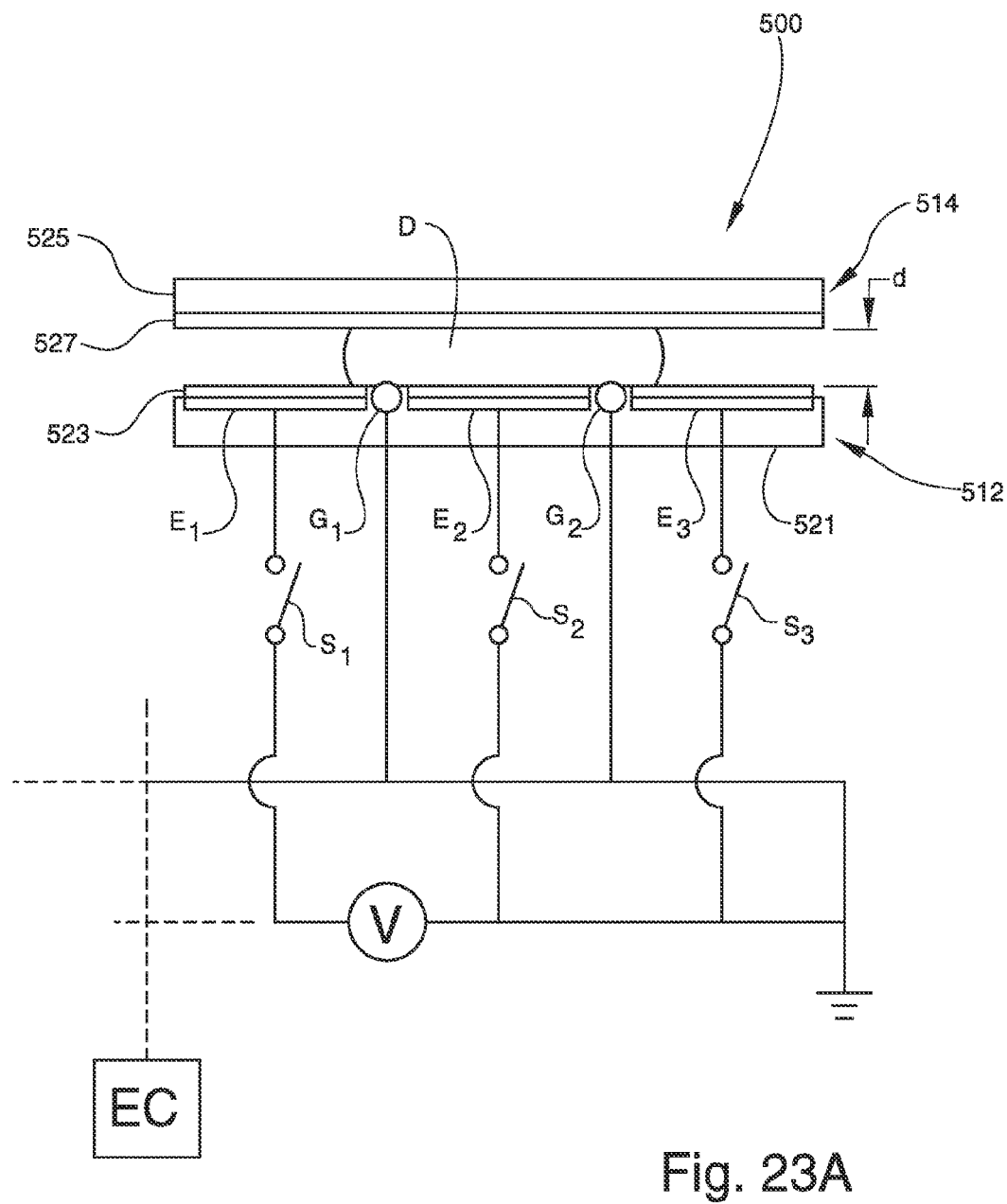
Figure 23B:
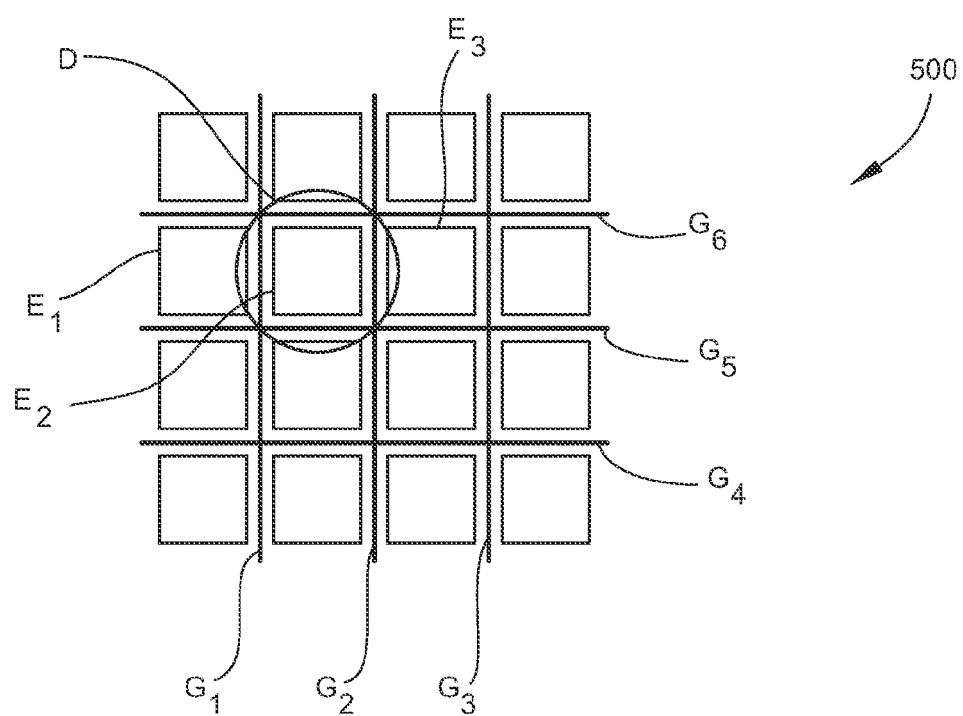
Figure 24A:
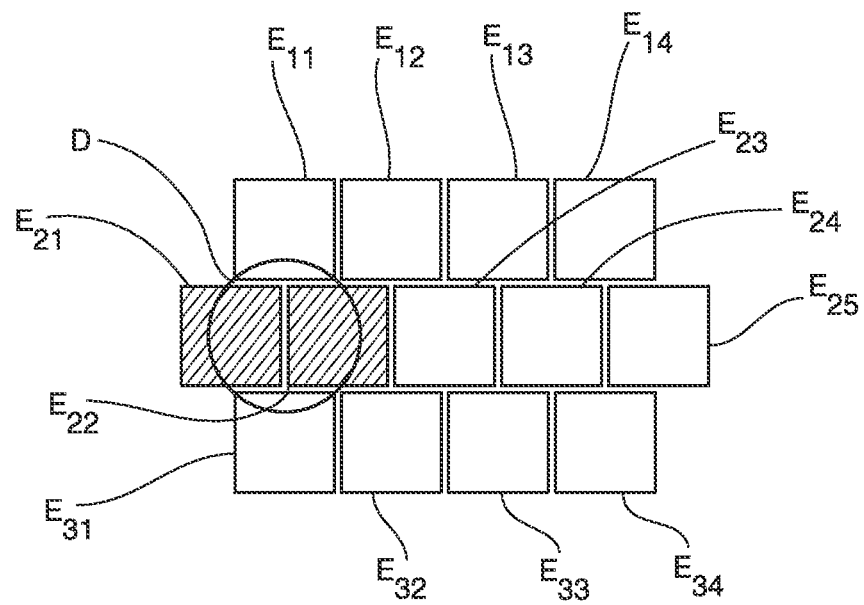
Figure 24B:
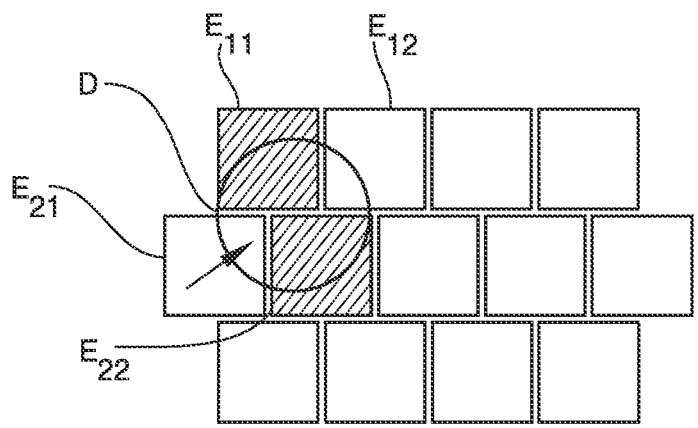
Figure 24C:
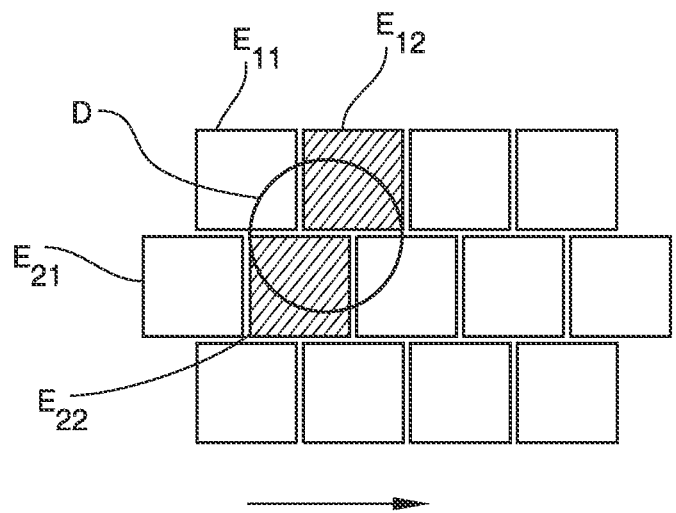
Figure 24D:
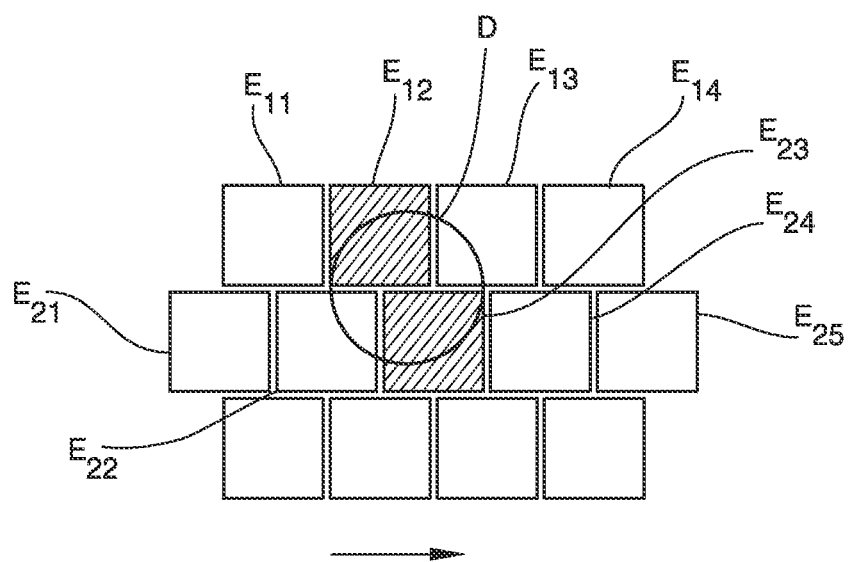
Figure 25A:
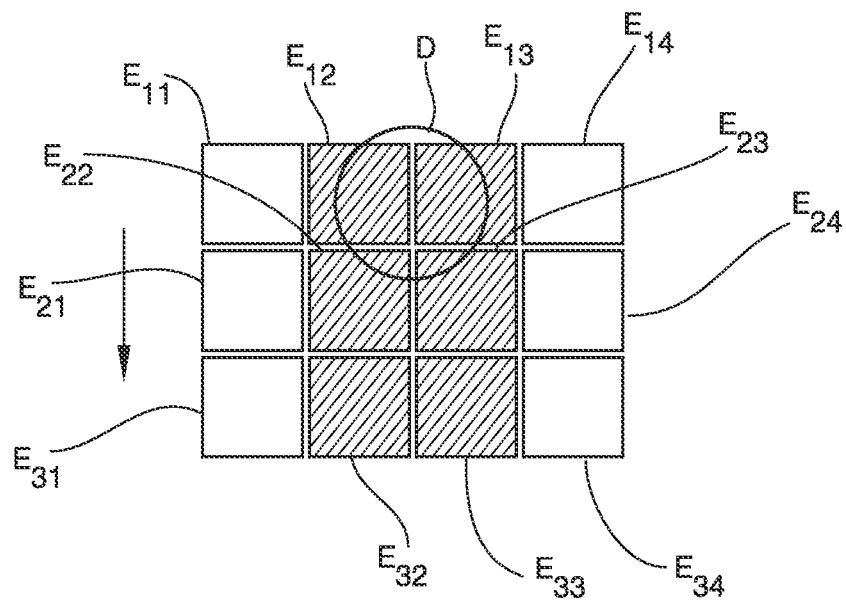
Figure 25B:
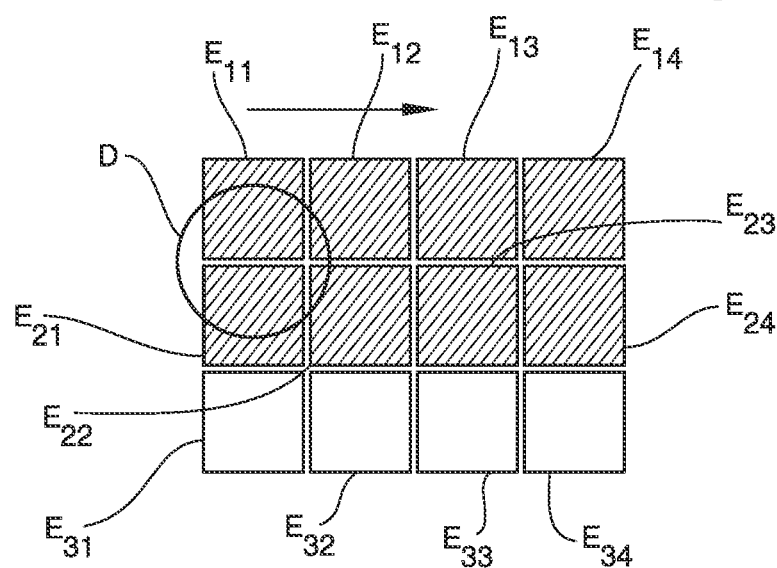

FIG. 23A is a cross-sectional view of an electrowetting microactuator mechanism having a single-sided electrode configuration in accordance with another embodiment of the present invention;

FIG. 23B is a top plan view of a portion of the mechanism illustrated in FIG. 23A with its upper plane removed;

FIGS. 24A-24D are sequential schematic views of an electrowetting microactuator mechanism having an alternative single-sided electrode configuration, illustrating electrowetting-based movement of a droplet positioned on a misaligned electrode array of the mechanism; and FIGS. 25A and 25B are schematic views of an alternative electrowetting microactuator mechanism having a single-sided electrode configuration arranged as an aligned array, respectively illustrating a droplet actuated in north-south and east-west directions.

7 DETAILED DESCRIPTION OF THE INVENTION

For purposes of the present disclosure, the terms "layer" and "film" are used interchangeably to denote a structure or body that is typically but not necessarily planar or substantially planar, and is typically deposited on, formed on, coats, treats, or is otherwise disposed on another structure.

For purposes of the present disclosure, the term "communicate" (e.g., a first component "communicates with" or "is in communication with" a second component) is used herein to indicate a structural, functional, mechanical, electrical, optical, or fluidic relationship, or any combination thereof, between two or more components or elements. As such, the fact that one component is said to communicate with a second component is not intended to exclude the possibility that additional components may be present between, and/or operatively associated or engaged with, the first and second components.

For purposes of the present disclosure, it will be understood that when a given component such as a layer, region or substrate is referred to herein as being disposed or formed "on", "in", or "at" another component, that given component can be directly on the other component or, alternatively, intervening components (for example, one or more buffer layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

For purposes of the present disclosure, it will be understood that when a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

As used herein, the term "reagent" describes any material useful for reacting with, diluting, solvating, suspending, emulsifying, encapsulating, interacting with, or adding to a sample material.

The droplet-based methods and apparatus provided by the present invention will now be described in detail, with reference being made as necessary to the accompanying FIGS. 1-25B.

7.1 Droplet-Based Actuation by Electrowetting

Figure 1:
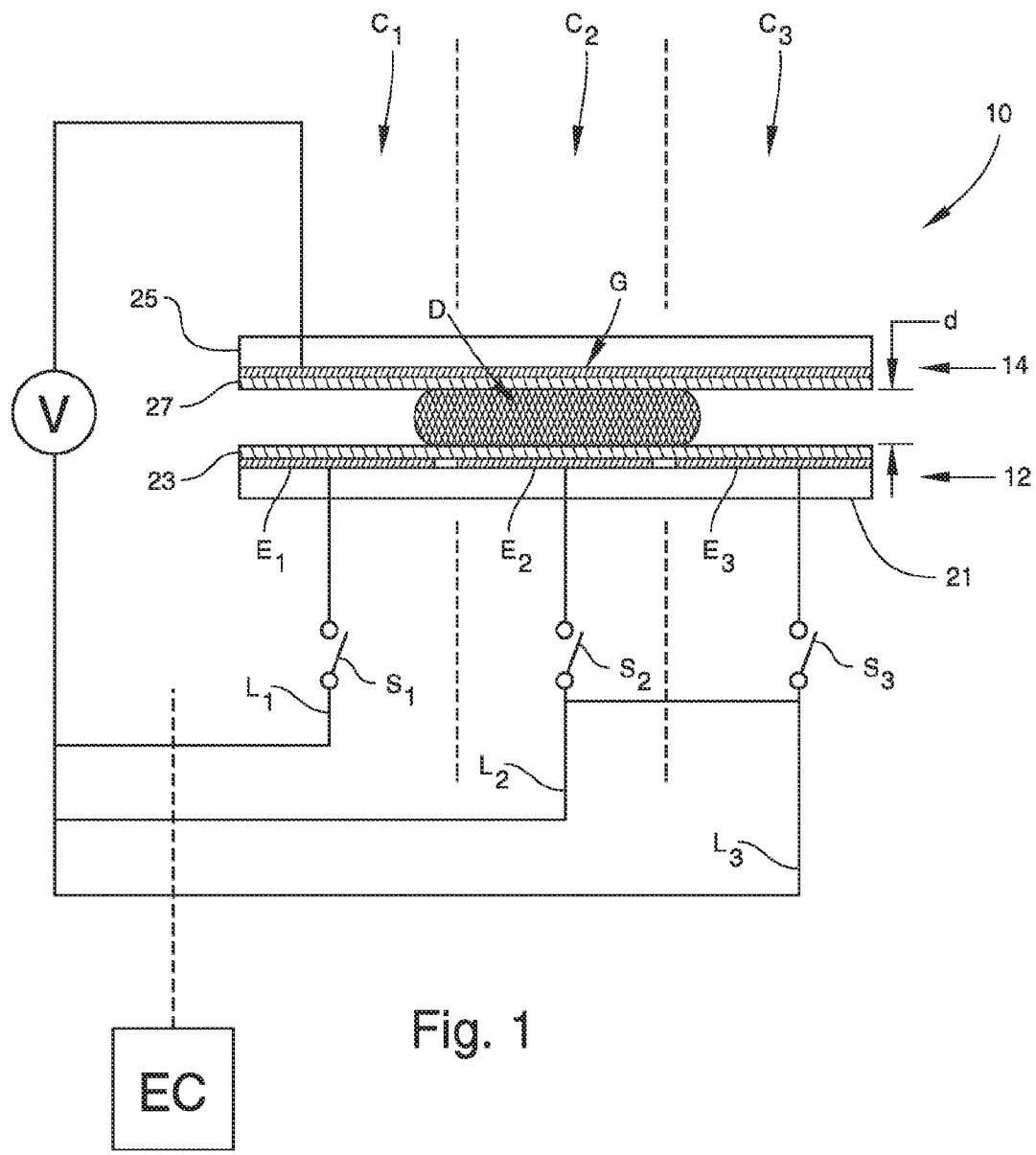
FIG. 1 is a cross-sectional view of an electrowetting microactuator mechanism having a two-sided electrode configuration in accordance with the present invention.

Referring now to FIG. 1, an electrowetting microactuator mechanism, generally designated 10, is illustrated as a preferred embodiment for effecting electrowetting-based manipulations on a droplet D without the need for pumps, valves, or fixed channels. Droplet D is electrolytic, polarizable, or otherwise capable of conducting current or being electrically charged. Droplet D is sandwiched between a lower plane, generally designated 12, and an upper plane, generally designated 14. The terms "upper" and "lower" are used in the present context only to distinguish these two planes 12 and 14, and not as a limitation on the orientation of planes 12 and 14 with respect to the horizontal. Lower plane 12 comprises an array of independently addressable control electrodes. By way of example, a linear series of three control or drive electrodes E (specifically $E_1$, $E_2$, and $E_3$) are illustrated in FIG. 1. It will be understood, however, that control electrodes $E_1$, $E_2$, and $E_3$ could be arranged along a non-linear path such as a circle. Moreover, in the construction of devices benefiting from the present invention (such as a microfluidic chip), control electrodes $E_1$, $E_2$, and $E_3$ will typically be part of a larger number of control electrodes that collectively form a two-dimensional electrode array or grid. FIG. 1 includes dashed lines between adjacent control electrodes $E_1$, $E_2$, and $E_3$ to conceptualize unit cells, generally designated C (specifically $C_1$, $C_2$ and $C_3$). Preferably, each unit cell $C_1$, $C_2$, and $C_3$ contains a single control electrode, $E_1$, $E_2$, and $E_3$, respectively. Typically, the size of each unit cell C or control electrode E is between approximately 0.05 mm to approximately 2 mm.

Control electrodes $E_1$, $E_2$, and $E_3$ are embedded in or formed on a suitable lower substrate or plate 21. A thin lower layer 23 of hydrophobic insulation is applied to lower plate 21 to cover and thereby electrically isolate control electrodes $E_1$, $E_2$, and $E_3$. Lower hydrophobic layer 23 can be a single, continuous layer or alternatively can be patterned to cover only the areas on lower plate 21 where control electrodes $E_1$, $E_2$ and $E_3$ reside. Upper plane 14 comprises a single continuous ground electrode G embedded in or formed on a suitable upper substrate or plate 25. Alternatively, a plurality of ground electrodes G could be provided in parallel with the arrangement of corresponding control electrodes $E_1$, $E_2$ and $E_3$, in which case one ground electrode G could be associated with one corresponding control electrode E. Preferably, a thin upper layer 27 of hydrophobic insulation is also applied to upper plate 25 to isolate ground electrode G. One non-limiting example of a hydrophobic material suitable for lower layer 23 and upper layer 27 is TEFLON® AF 1600 material (available from E. I. duPont deNemours and Company, Wilmington, Del.). The geometry of microactuator mechanism 10 and the volume of droplet D are controlled such that the footprint of droplet D overlaps at least two control electrodes (e.g., $E_1$ and $E_3$) adjacent to the central control electrode (e.g., $E_2$) while also making contact with upper layer 27. Preferably, this is accomplished by specifying a gap or spacing d, which is defined between lower plane 12 and upper plane 14 as being less than the diameter that droplet D would have in an unconstrained state. Typically, the cross-sectional dimension of spacing d is between approximately 0.01 mm to approximately 1 mm. Preferably, a medium fills gap d and thus surrounds droplet D. The medium can be either an inert gas such as air or an immiscible fluid such as silicone oil to prevent evaporation of droplet D.

Ground electrode G and control electrodes $E_1$, $E_2$ and $E_3$ are placed in electrical communication with at least one suitable voltage source V, which preferably is a DC voltage source but alternatively could be an AC voltage source, through conventional conductive lead lines $L_1$, $L_2$ and $L_3$. Each control electrode $E_1$, $E_2$ and $E_3$ is energizable independently of the other control electrodes $E_1$, $E_2$ and $E_3$. This can be accomplished by providing suitable switches $S_1$, $S_2$ and $S_3$ communicating with respective control electrodes $E_1$, $E_2$ and $E_3$, or other suitable means for independently rendering each control electrode $E_1$, $E_2$ and $E_3$ either active (ON state, high voltage, or binary 1) or inactive (OFF state, low voltage, or binary 0). In other embodiments, or in other areas of the electrode array, two or more control electrodes E can be commonly connected so as to be activated together.

The structure of electrowetting microactuator mechanism 10 can represent a portion of a microfluidic chip, on which conventional microfluidic and/or microelectronic components can also be integrated. As examples, the chip could also include resistive heating areas, microchannels, micropumps, pressure sensors, optical waveguides, and/or biosensing or chemosensing elements interfaced with MOS (metal oxide semiconductor) circuitry.

Figure 2:
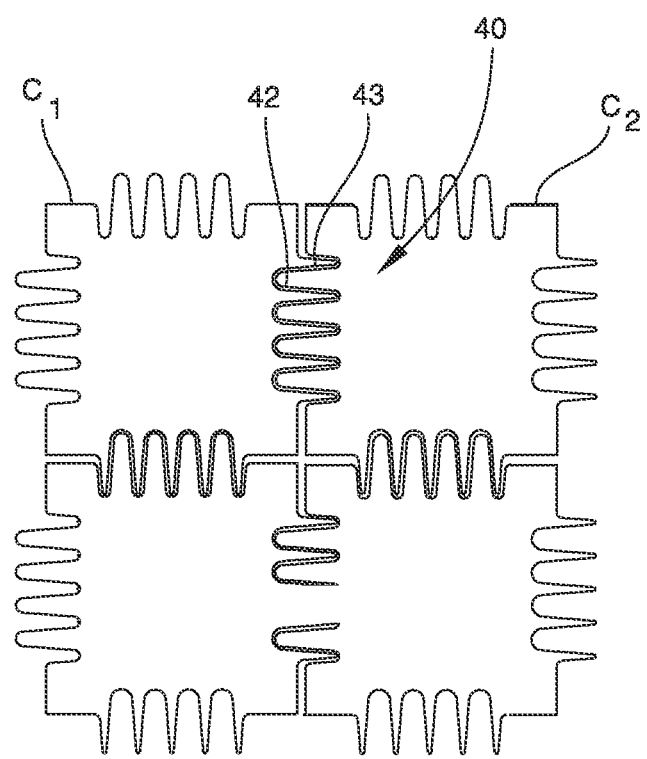
FIG. 2 is a top plan view of an array of electrode cells having interdigitated perimeters accordance with one embodiment of the present invention.
Figure 3:
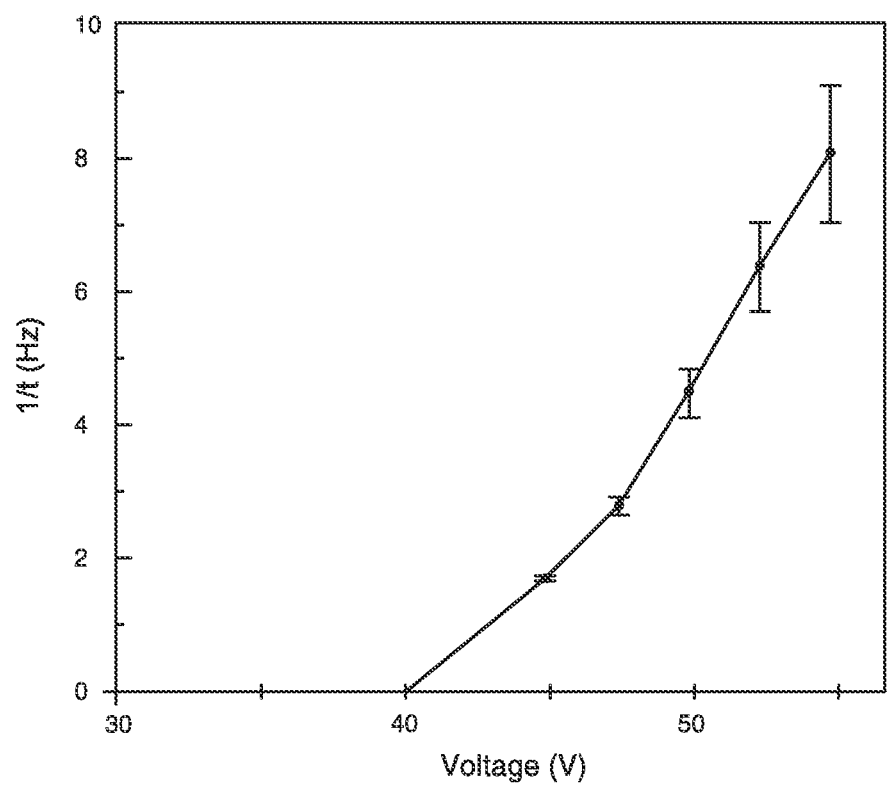
FIG. 3 is a plot of switching rate as a function of voltage demonstrating the performance of an electrowetting microactuator mechanism structured in accordance with the present invention.

Referring now to FIG. 2, an electrode array or portion thereof is illustrated in which each structural interface between adjacent unit cells (e.g., $C_1$ and $C_2$) associated with control electrodes (not shown) is preferably characterized by an interdigitated region, generally designated 40, defined by interlocking projections 42 and 43 extending outwardly from the main planar structures of respective unit cells $C_1$ and $C_2$. Such interdigitated regions 40 can be useful in rendering the transition from one unit cell (e.g., $C_1$) to an adjacent unit cell (e.g., $C_2$) more continuous, as opposed to providing straight-edged boundaries at the cell-cell interfaces. It will be noted, however, that the electrodes or unit cells according to any embodiment of the invention can have any polygonal shape that is suitable for constructing a closely-packed two-dimensional array, such as a square or octagon.

Referring back to FIG. 1, the basic electrowetting technique enabled by the design of microactuator mechanism 10 will now be described. Initially, all control electrodes (i.e., control electrode $E_2$ on which droplet D is centrally located and adjacent control electrodes $E_1$ and $E_3$) are grounded or floated, and the contact angle everywhere on droplet D is equal to the equilibrium contact angle associated with that droplet D. When an electrical potential is applied to control electrode $E_2$ situated underneath droplet D, a layer of charge builds up at the interface between droplet D and energized control electrode $E_2$, resulting in a local reduction of the interfacial energy $\gamma_{SL}$. Since the solid insulator provided by lower hypdrophobic insulating layer 23 controls the capacitance between droplet D and control electrode $E_2$, the effect does not depend on the specific space-charge effects of the electrolytic liquid phase of droplet D, as is the case in previously developed uninsulated electrode implementations.

The voltage dependence of the interfacial energy reduction is described by $$\gamma_{SL}(V) = \gamma_{SL}(O) - \frac{\varepsilon}{2d}V^2, \quad (1)$$

where $\varepsilon$ is the permittivity of the insulator, d is the thickness of the insulator, and V is the applied potential. The change in $\gamma_{SL}$ acts through Young's equation to reduce the contact angle at the interface between droplet D and energized control electrode $E_2$. If a portion of droplet D also overlaps a grounded electrode $E_1$ or $E_3$, the droplet meniscus is deformed asymmetrically and a pressure gradient is established between the ends of droplet D, thereby resulting in bulk flow towards the energized electrode $E_1$ or $E_3$. For example, droplet D can be moved to the left (i.e., to unit cell $C_1$) by energizing control electrode $E_1$ while maintaining control electrodes $E_2$ and $E_3$ at the ground state. As another example, droplet D can be moved to the right (i.e., to unit cell $C_3$) by energizing control electrode $E_3$ while maintaining control electrodes $E_1$ and $E_2$ at the ground state.

The following EXAMPLE describes a prototypical embodiment of electrowetting microactuator mechanism 10, with reference being generally made to FIGS. 1 and 2.

7.2 Example

A prototype device consisting of a single linear array of seven interdigitated control electrodes E at a pitch of 1.5 mm was fabricated and tested. Control electrodes E were formed by patterning a 2000-Å thick layer of chrome on a glass lower plate 21 using standard microfabrication techniques. The chips were then coated with a 7000 Å layer of Parylene C followed by a layer 23 of approximately 2000 Å of TEFLON® AF 1600. Ground electrode G consisted of an upper plate 25 of glass coated with a conducting layer ($R_\varsigma$<20 Ω/square) of transparent indium-tin-oxide (ITO). A thin (~500 Å) layer 27 of TEFLON® AF 1600 was also applied to ground electrode G. The thin TEFLON® coating on ground electrode G served to hydrophobize the surface, but was not presumed to be insulative. After coating with TEFLON®, both surfaces had a contact angle of 104° with water.

Water droplets (0.7-1.0 μl) of 100 mM KCl were dispensed onto the array using a pipette, and upper plate 25 was positioned to provide a gap d of 0.3 mm between the opposing electrodes E and G. A customized clamp with spring-loaded contact pins (not shown) was used to make connections to the bond pads. A computer was used to control a custom-built electronic interface which was capable of independently switching each output between ground and the voltage output of a 120 V DC power supply.

A droplet D was initially placed on the center of the grounded control electrode (e.g., $E_2$) and the potential on the adjacent electrode (e.g., control electrode $E_1$ or $E_3$) was increased until motion was observed. Typically, a voltage of 30-40 V was required to initiate movement of droplet D. Once this threshold was exceeded, droplet movement was both rapid and repeatable. It is believed that contact angle hysteresis is the mechanism responsible for this threshold effect. By sequentially energizing four adjacent control electrodes E at 80 V of applied potential, droplet D was moved repeatedly back and forth across all four control electrodes E at a switching frequency of 15 Hz.

The transit time $t_{tr}$ of the droplet D was defined as the time required for droplet D to reach the far edge of the adjacent electrode following the application of the voltage potential. The transit time $t_{tr}$ thus represented the minimum amount of time allowed between successive transfers, and ($1/t_{tr}$) was the maximum switching rate for continuous transfer of a droplet D. The maximum switching rate as a function of voltage is plotted in FIG. 3, where $t_{tr}$ was determined by counting recorded video frames of a moving droplet D.

Sustained droplet transport over 1000's of cycles at switching rates of up to 1000 Hz has been demonstrated for droplets of 6 nL volume. This rate corresponds to an average droplet velocity of 10.0 cm/s, which is nearly 300 times faster than a previously reported method for electrical manipulation of droplets. See M. Washizu, IEEE Trans. Ind. Appl. 34, 732 (1998). Comparable velocities cannot be obtained in thermocapillary systems because (for water) the required temperature difference between the ends of droplet D exceeds 100° C. See Sammarco et al., AIChE J., 45, 350 (1999). These results demonstrate the feasibility of electrowetting as an actuation mechanism for droplet-based microfluidic systems. This design can be extended to arbitrarily large two-dimensional arrays to allow precise and independent control over large numbers of droplets D and to serve as a general platform for microfluidic processing.

Referring now to FIGS. 4A-7B, examples of some basic droplet-manipulative operations are illustrated. As in the case of FIG. 1, a linear arrangement of three unit cells $C_1$, $C_2$ and $C_3$ and associated control electrodes $E_1$, $E_2$ and $E_3$ are illustrated, again with the understanding that these unit cells $C_1$, $C_2$ and $C_3$ and control electrodes $E_1$, $E_2$ and $E_3$ can form a section of a larger linear series, non-linear series, or two-dimensional array of unit cells/control electrodes. For convenience, in FIGS. 4B-7B, corresponding control electrodes and unit cells are collectively referred to as control electrodes $E_1$, $E_2$ and $E_3$. Moreover, unit cells $C_1$, $C_2$, and $C_3$ can be physical entities, such as areas on a chip surface, or conceptual elements. In each of FIGS. 4A-7B, an active (i.e., energized) control electrode $E_1$, $E_2$, or $E_3$ is indicated by designating its associated electrical lead line $L_1$, $L_2$, or $L_3$ "ON", while an inactive (i.e., de-energized, floated, or grounded) control electrode $E_1$, $E_2$, or $E_3$ is indicated by designating its associated electrical lead line $L_1$, $L_2$, or $L_3$ "OFF".

Figure 4A:
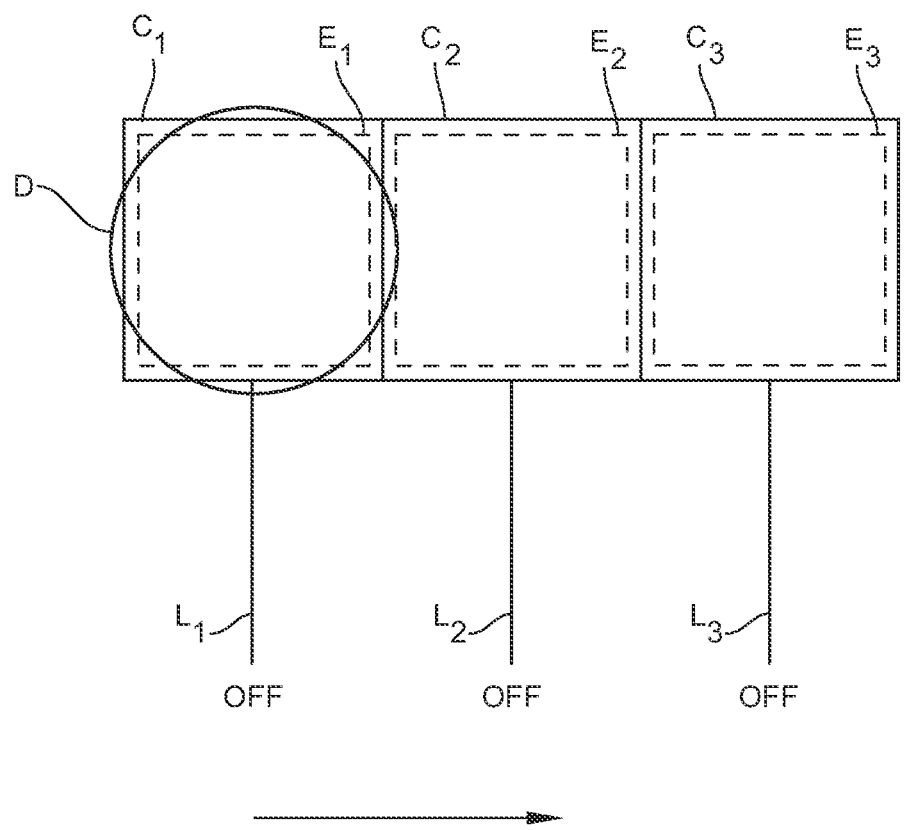
FIGS. 4A-4D are sequential schematic views of a droplet being moved by the electrowetting technique of the present invention.
Figure 4B:
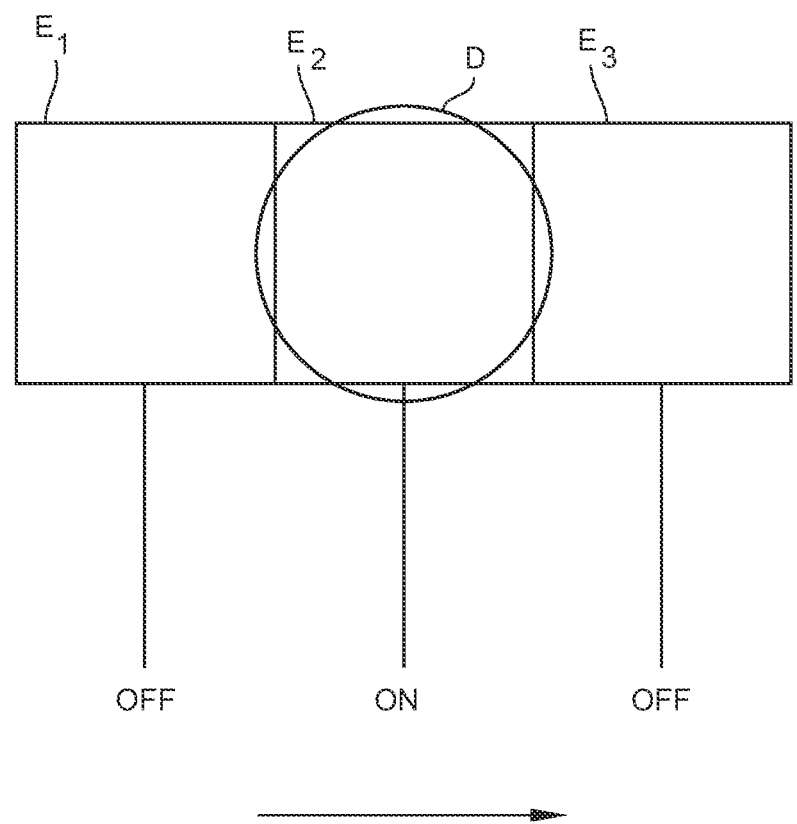
Figure 4C:
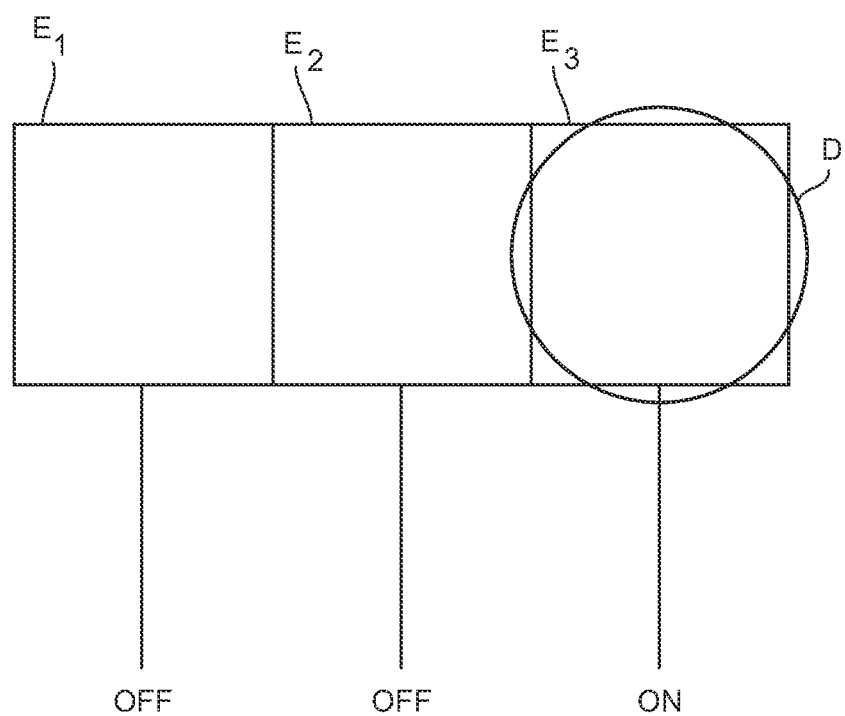
Figure 4D:
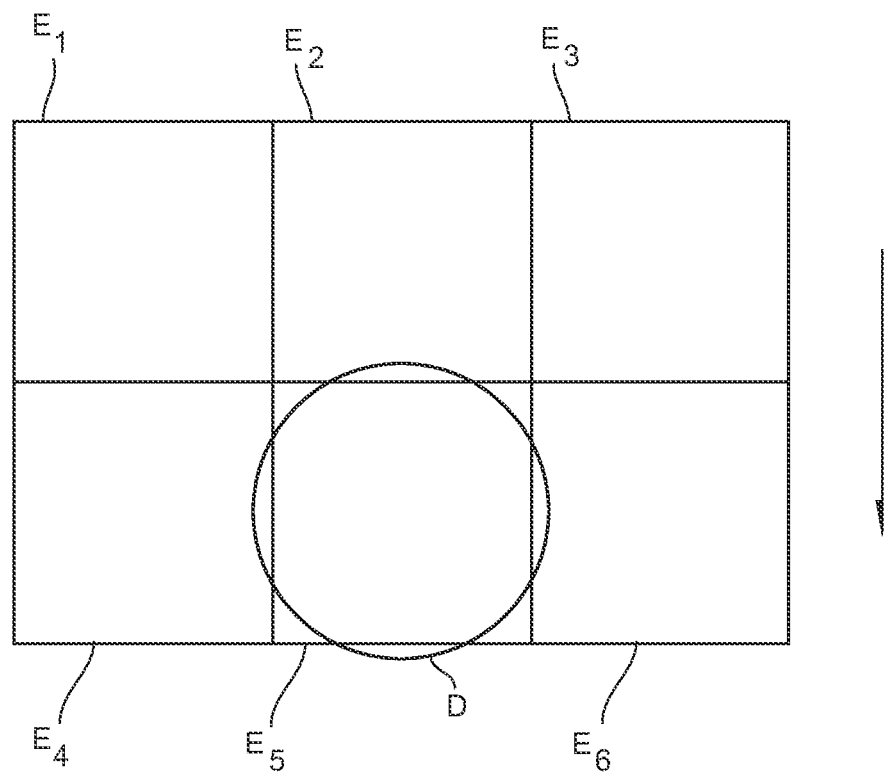

Turning to FIGS. 4A-4D, a basic MOVE operation is illustrated. FIG. 4A illustrates a starting position at which droplet D is centered on control electrode $E_1$. Initially, all control electrodes $E_1$, $E_2$ and $E_3$ are grounded so that droplet D is stationary and in equilibrium on control electrode $E_1$. Alternatively, control electrode $E_1$ could be energized while all adjacent control electrodes (e.g., $E_2$) are grounded so as to initially maintain droplet D in a "HOLD" or "STORE" state, and thereby isolate droplet D from adjoining regions of an array where other manipulative operations might be occurring on other droplets. To move droplet D in the direction indicated by the arrow in FIGS. 4A-4B, control electrode $E_2$ is energized to attract droplet D and thereby cause droplet D to move and become centered on control electrode $E_2$, as shown in FIG. 4B. Subsequent activation of control electrode $E_3$, followed by removal of the voltage potential at control electrode $E_2$, causes droplet D to move onto control electrode $E_3$ as shown in FIG. 4C. This sequencing of electrodes can be repeated to cause droplet D to continue to move in the desired direction indicated by the arrow. It will also be evident that the precise path through which droplet D moves across the electrode array is easily controlled by appropriately programming an electronic control unit (such as a conventional microprocessor) to activate and de-activate selected electrodes of the array according to a predetermined sequence. Thus, for example, droplet D can be actuated to make right- and left-hand turns within the array. For instance, after droplet D has been moved to control electrode $E_2$ from $E_1$ as shown in FIG. 4B, droplet D can then be moved onto control electrode $E_5$ of another row of electrodes $E_4$-$E_6$ as shown in FIG. 4D. Moreover, droplet D can be cycled back and forth (e.g., shaken) along a desired number of unit cells and at a desired frequency for various purposes such as agitation of droplet D, as described in the EXAMPLE hereinabove.

Figure 5A:
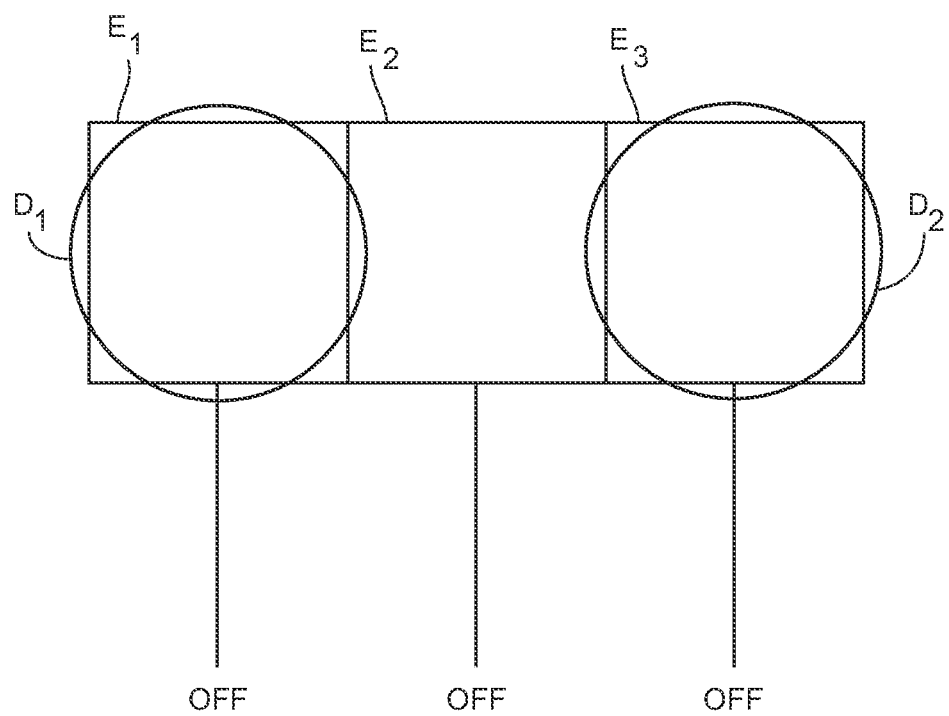
FIGS. 5A-5C are sequential schematic views illustrating two droplets combining into a merged droplet using the electrowetting technique of the present invention.
Figure 5B:
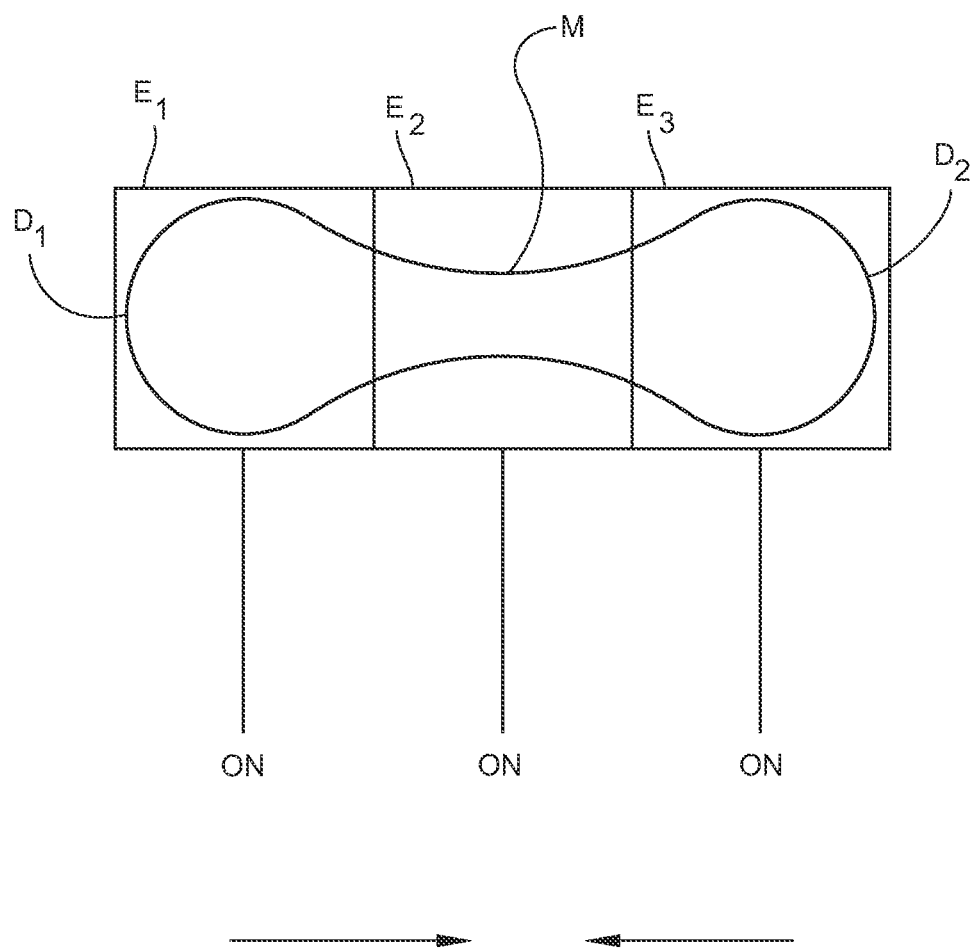
Figure 5C:
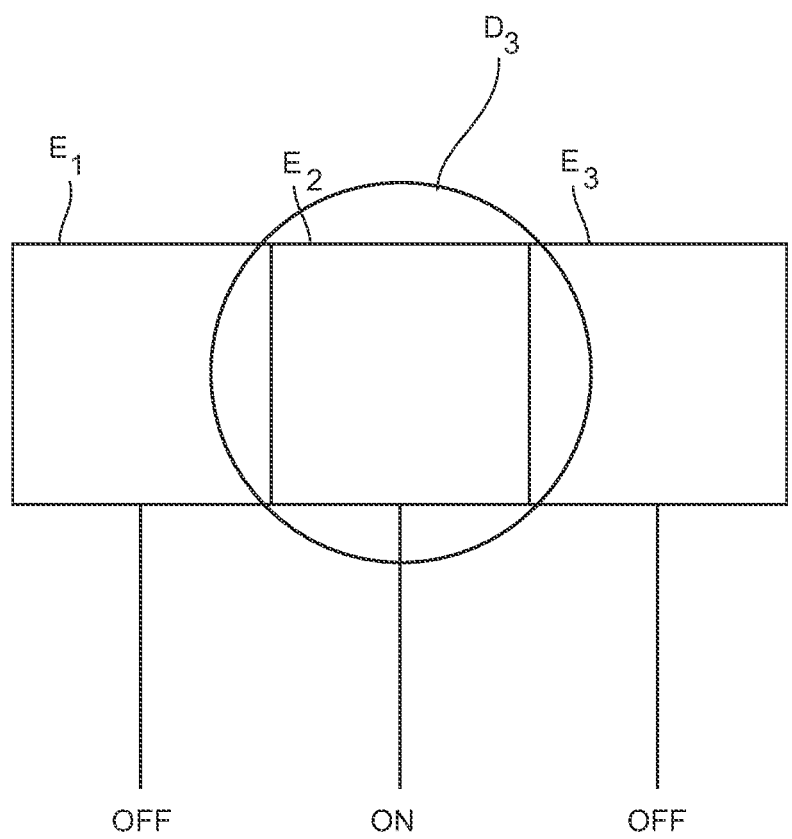

FIGS. 5A-5C illustrate a basic MERGE or MIX operation wherein two droplets $D_1$ and $D_2$ are combined into a single droplet $D_3$. In FIG. 5A, two droplets $D_1$ and $D_2$ are initially positioned at control electrodes $E_1$ and $E_3$ and separated by at least one intervening control electrode $E_2$. As shown in FIG. 5B, all three control electrodes $E_1$, $E_2$ and $E_3$ are then activated, thereby drawing droplets $D_1$ and $D_2$ toward each other across central control electrode $E_2$ as indicated by the arrows in FIG. 5B. Once the opposing sides of droplets $D_1$ and $D_2$ encounter each other at central control electrode $E_2$, a single meniscus M is created that joins the two droplets $D_1$ and $D_2$ together. As shown in FIG. 5C, the two outer control electrodes $E_1$ and $E_3$ are then returned to the ground state, thereby increasing the hydrophobicity of the surfaces of the unit cells associated with outer electrodes $E_1$ and $E_3$ and repelling the merging droplets $D_1$ and $D_2$, whereas energized central control electrode $E_2$ increases the wettability of its proximal surface contacting droplets $D_1$ and $D_2$. As a result, droplets $D_1$ and $D_2$ combine into a single mixed droplet $D_3$ as shown in FIG. 5C, which represents the lowest energy state possible for droplet $D_3$ under these conditions. The resulting combined droplet $D_3$ can be assumed to have twice the volume or mass as either of the original, non-mixed droplets $D_1$ and $D_2$, since parasitic losses are negligible or zero. This is because evaporation of the droplet material is avoided due to the preferable use of a filler fluid (e.g., air or an immiscible liquid such as silicone oil) to surround the droplets, because the surfaces contacting the droplet material (e.g., upper and lower hydrophobic layers 27 and 23 shown in FIG. 1) are low-friction surfaces, and/or because the electrowetting mechanism employed by the invention is non-thermal.

In the present discussion, the terms MERGE and MIX have been used interchangeably to denote the combination of two or more droplets. This is because the merging of droplets does not in all cases directly or immediately result in the complete mixing of the components of the initially separate droplets. Whether merging results in mixing can depend on many factors. These factors can include the respective compositions or chemistries of the droplets to be mixed, physical properties of the droplets or their surroundings such as temperature and pressure, derived properties of the droplets such as viscosity and surface tension, and the amount of time during which the droplets are held in a combined state prior to being moved or split back apart. As a general matter, the mechanism by which droplets are mixed together can be categorized as either passive or active mixing. In passive mixing, the merged droplet remain on the final electrode throughout the mixing process. Passive mixing can be sufficient under conditions where an acceptable degree of diffusion within the combined droplet occurs. In active mixing, on the other hand, the merged droplet is then moved around in some manner, adding energy to the process to effect complete or more complete mixing. Active mixing strategies enabled by the present invention are described hereinbelow.

It will be further noted that in the case where a distinct mixing operation is to occur after a merging operation, these two operations can occur at different sections or areas on the electrode array of the chip. For instance, two droplets can be merged at one section, and one or more of the basic MOVE operations can be implemented to convey the merged droplet to another section. An active mixing strategy can then be executed at this other section or while the merged droplet is in transit to the other section, as described hereinbelow.

Figure 6A:
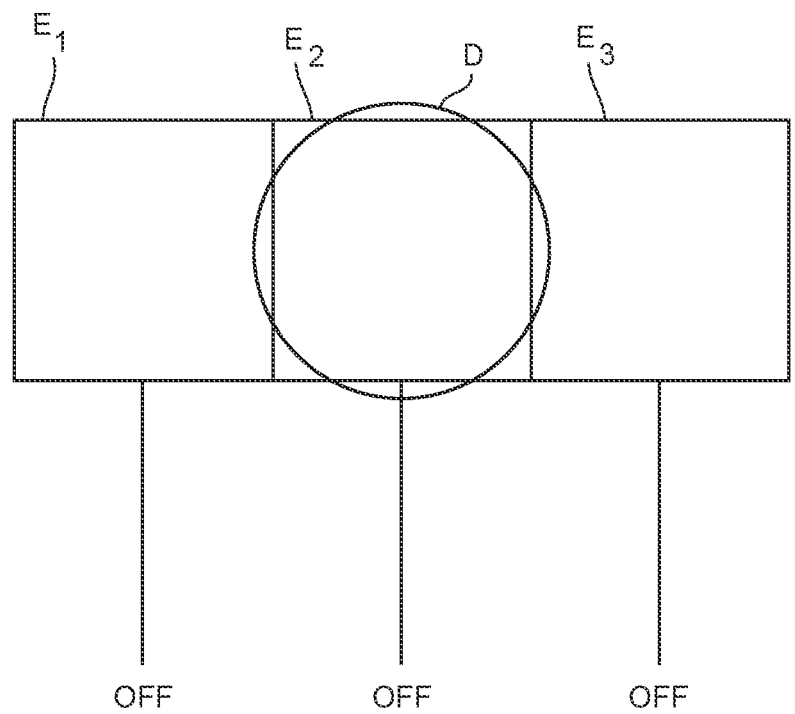
FIGS. 6A-6C are sequential schematic views showing a droplet being split into two droplets by the electrowetting technique of the present invention.
Figure 6B:
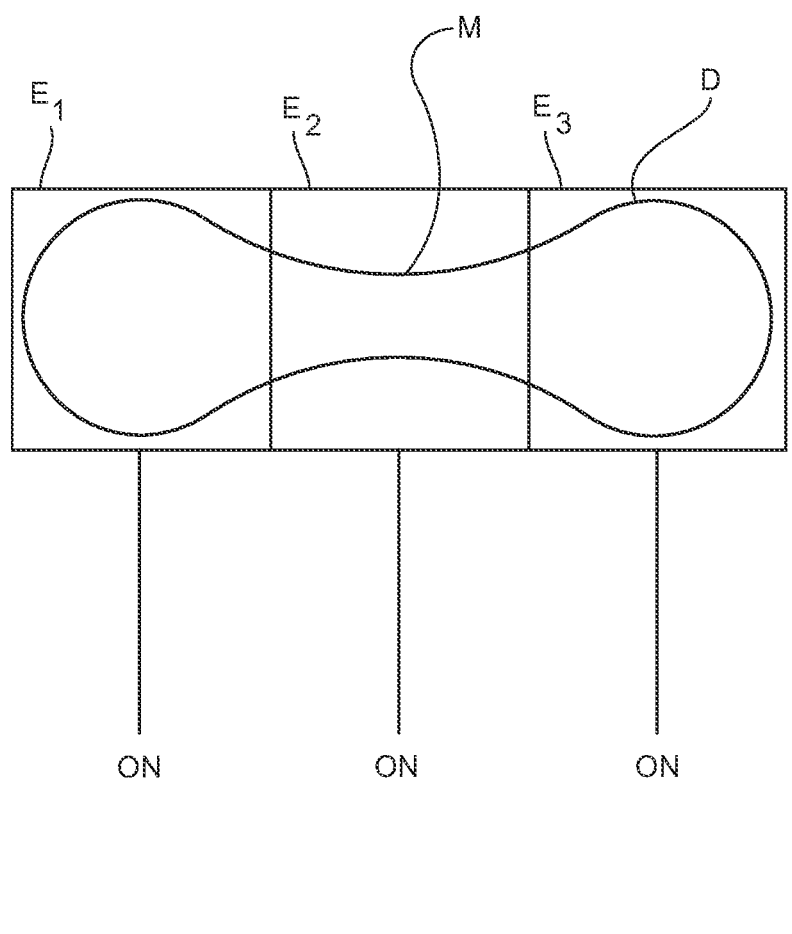
Figure 6C:
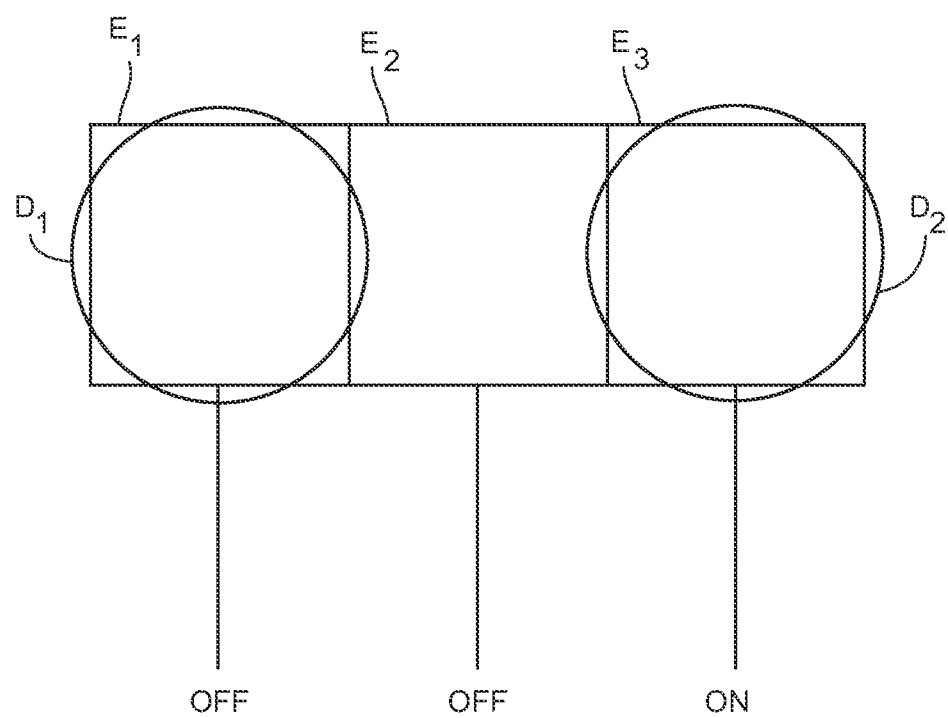

FIGS. 6A-6C illustrate a basic SPLIT operation, the mechanics of which are essentially the inverse of those of the MERGE or MIX operation just described. Initially, as shown in FIG. 6A, all three control electrodes $E_1$, $E_2$ and $E_3$ are grounded, so that a single droplet D is provided on central control electrode $E_2$ in its equilibrium state. As shown in FIG. 6B, outer control electrodes $E_1$ and $E_3$ are then energized to draw droplet D laterally outwardly (in the direction of the arrows) onto outer control electrodes $E_1$ and $E_3$. This has the effect of shrinking meniscus M of droplet D, which is characterized as "necking" with outer lobes being formed on both energized control electrodes $E_1$ and $E_3$. Eventually, the central portion of meniscus M breaks, thereby creating two new droplets $D_1$ and $D_2$ split off from the original droplet D as shown in FIG. 6C. Split droplets $D_1$ and $D_2$ have the same or substantially the same volume, due in part to the symmetry of the physical components and structure of electrowetting microactuator mechanism 10 (FIG. 1), as well as the equal voltage potentials applied to outer control electrodes $E_1$ and $E_3$. It will be noted that in many implementations of the invention, such as analytical and assaying procedures, a SPLIT operation is executed immediately after a MERGE or MIX operation so as to maintain uniformly-sized droplets on the microfluidic chip or other array-containing device.

Figure 7A:
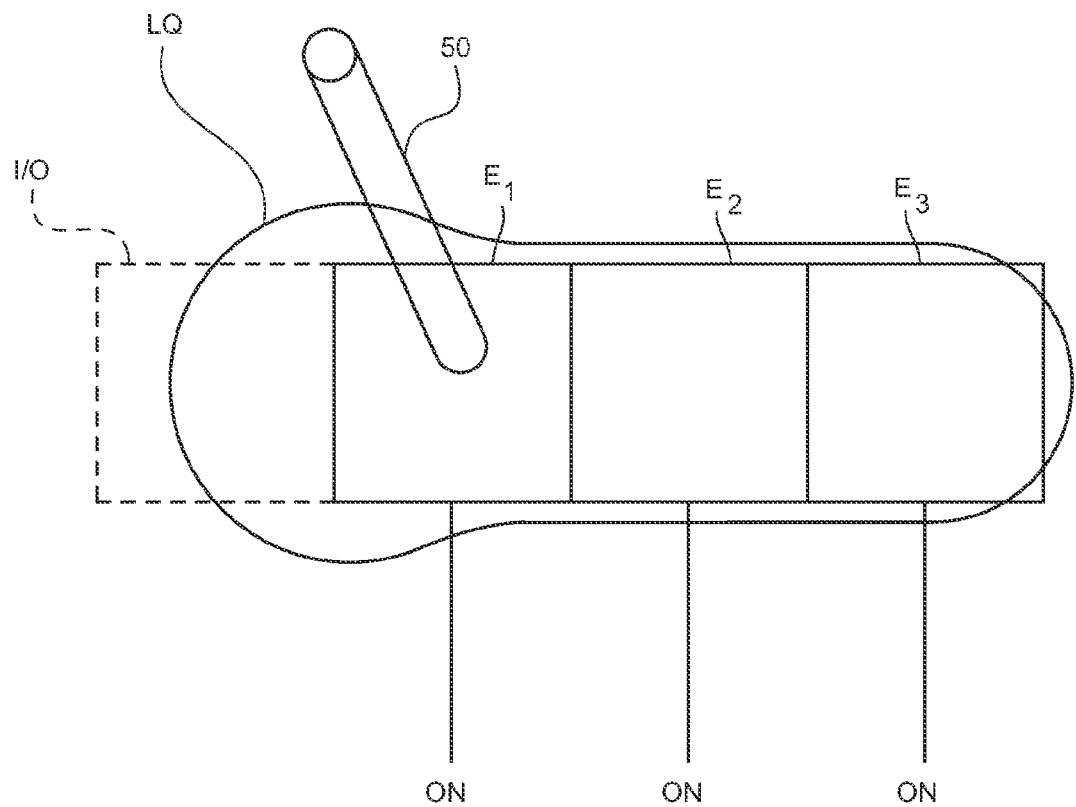
FIGS. 7A and 7B are sequential schematic views showing a liquid being dispensed on an electrode array and a droplet being formed from the liquid.
Figure 7B:
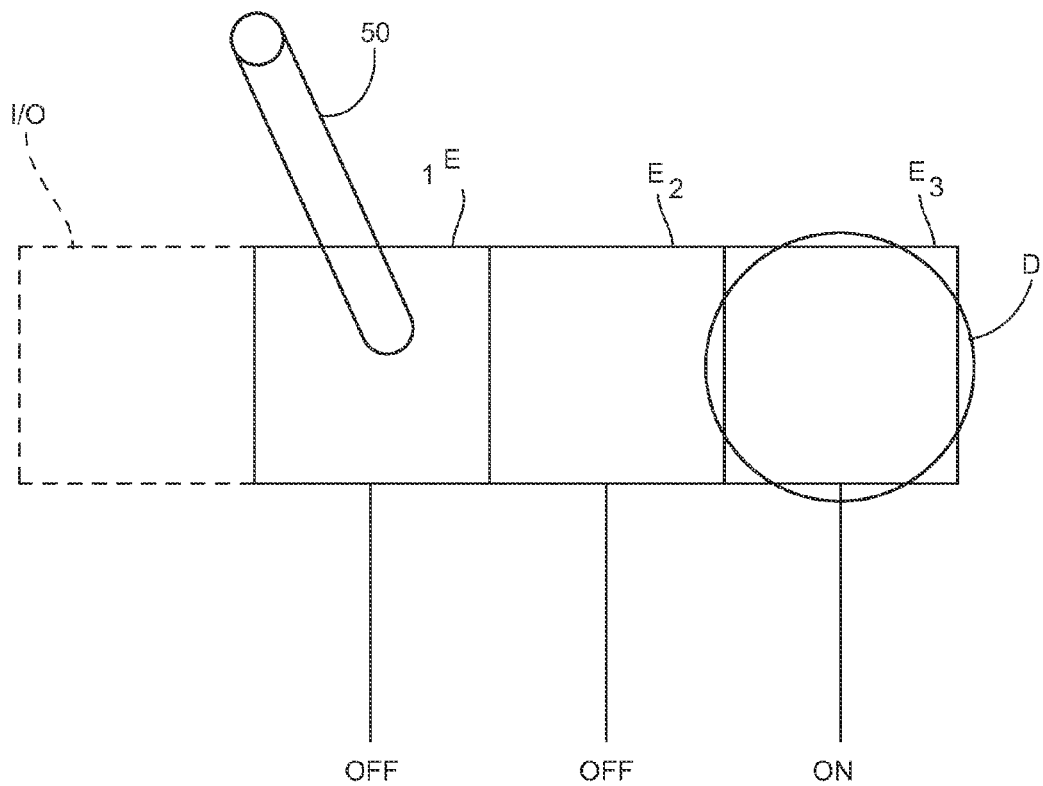

Referring now to FIGS. 7A and 7B, a DISCRETIZE operation can be derived from the basic SPLIT operation. As shown in FIG. 7A, a surface or port I/O is provided either on an electrode grid or at an edge thereof adjacent to electrode-containing unit cells (e.g., control electrode $E_1$), and serves as an input and/or output for liquid. A liquid dispensing device 50 is provided, and can be of any conventional design (e.g., a capillary tube, pipette, fluid pen, syringe, or the like) adapted to dispense and/or aspirate a quantity of liquid LQ. Dispensing device 50 can be adapted to dispense metered doses (e.g., aliquots) of liquid LQ or to provide a continuous flow of liquid LQ, either at port I/O or directly at control electrode $E_1$. As an alternative to using dispensing device 50, a continuous flow of liquid LQ could be conducted across the surface of a microfluidic chip, with control electrodes $E_1$, $E_2$, and $E_3$ being arranged either in the direction of the continuous flow or in a non-collinear (e.g., perpendicular) direction with respect to the continuous flow. In the specific, exemplary embodiment shown in FIG. 7A, dispensing device 50 supplies liquid LQ to control electrode $E_1$.

To create a droplet on the electrode array, the control electrode directly beneath the main body of liquid LQ (control electrode $E_1$) and at least two control electrodes adjacent to the edge of the liquid body (e.g., control electrodes $E_1$ and $E_3$) are energized. This causes the dispensed body of liquid LQ to spread across control electrodes $E_1$ and $E_2$ as shown in FIG. 7A. In a manner analogous to the SPLIT operation described hereinabove with reference to FIGS.

6A-6C, the intermediate control electrode (control electrode $E_2$) is then de-energized to create a hydrophobic region between two effectively hydrophilic regions. The liquid meniscus breaks above the hydrophobic region to form or "pinch off" a new droplet D, which is centered on control electrode $E_3$ as shown in FIG. 7B. From this point, further energize/de-energize sequencing of other electrodes of the array can be effected to move droplet D in any desired row-wise and/or column-wise direction to other areas on the electrode array. Moreover, for a continuous input flow of liquid LQ, this dispensing process can be repeated to create a train of droplets on the grid or array, thereby discretizing the continuous flow. As described in more detail hereinbelow, the discretization process is highly useful for implementing droplet-based processes on the array, especially when a plurality of concurrent operations on many droplets are contemplated.

7.3 Droplet-Based Mixing Strategies

Figure 8A:
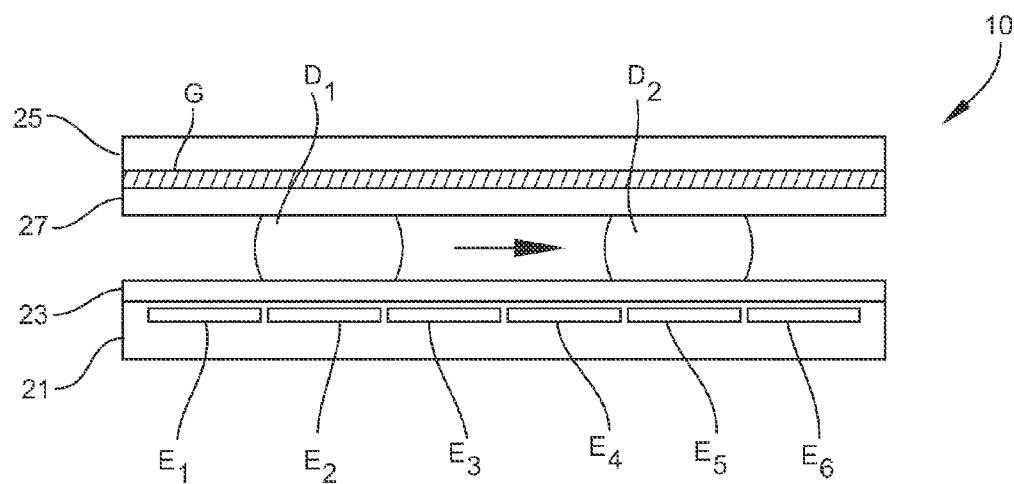
FIG. 8A is a cross-sectional view illustrating an electrowetting microactuator mechanism of the invention implementing a one-dimensional linear droplet merging process.
Figure 8B:
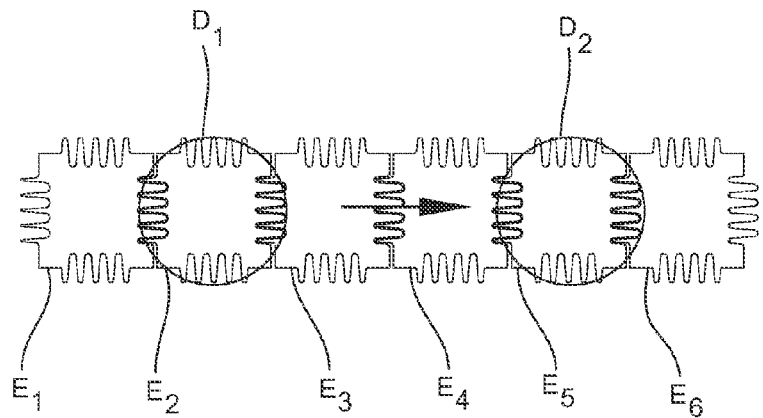
FIG. 8B is a top plan view of the configuration in FIG. 8A with the upper plane removed.

Examples of several strategies for mixing droplets in accordance with the present invention will now be described. Referring to FIGS. 8A and 8B, a configuration such as that of electrowetting microactuator mechanism 10, described hereinabove with reference to FIG. 1, can be employed to carry out merging and mixing operations on two or more droplets, e.g., droplets $D_1$ and $D_2$. In FIGS. 8A and 8B, droplets $D_1$ and $D_2$ are initially centrally positioned on control electrodes $E_2$ and $E_5$, respectively. Droplets $D_1$ and $D_2$ can be actuated by electrowetting to move toward each other and merge together on a final electrode in the manner described previously with reference to FIGS. 5A-5C. The final electrode can be an intermediately disposed electrode such as electrode $E_3$ or $E_4$. Alternatively, one droplet can move across one or more control electrodes and merge into another stationary droplet. Thus, as illustrated in FIGS. 8A and 8B, droplet $D_1$ can be actuated to move across intermediate electrodes $E_3$ and $E_4$ as indicated by the arrow and merge with droplet $D_2$ residing on electrode, such that the merging of droplets $D_1$ and $D_2$ occurs on electrode $E_5$. The combined droplet can then be actively mixed according to either a one-dimensional linear, two-dimensional linear, or two-dimensional loop mixing strategy.

As one example of a one-dimensional linear mixing strategy, multiple droplets can be merged as just described, and the resulting combined droplet then oscillated (or "shaken" or "switched") back and forth at a desired frequency over a few electrodes to cause perturbations in the contents of the combined droplet. This mixing process is described in the EXAMPLE set forth hereinabove and can involve any number of linearly arranged electrodes, such as electrodes in a row or column of an array. FIGS. 9A, 9B and 9C illustrate two-, three-, and four-electrode series, respectively, in which merging and mixing by shaking can be performed. As another example of one-dimensional linear mixing, multiple droplets are merged, and the combined droplet or droplets are then split apart as described hereinabove. The resulting split/merged droplets are then oscillated back and forth at a desired frequency over a few electrodes. The split/merged droplets can then be recombined, re-split, and re-oscillated for a number of successive cycles until the desired degree of mixing has been attained. Both of these one-dimensional, linear mixing approaches produce reversible flow within the combined droplet or droplets. It is thus possible that the mixing currents established by motion in one direction could be undone or reversed when the combined droplet oscillates back the other way. Therefore, in some situations, the reversible flow attending one-dimensional mixing processes may require undesirably large mixing times.

Referring now to FIGS. 10A-10C, another example of one-dimensional linear mixing referred to as "mixing-in-transport" is illustrated. This method entails combining two or more droplets and then continuously actuating the combined droplet in a forward direction along a desired flow path until mixing is complete. Referring to FIG. 10A, a combined droplet D is transported from a starting electrode $E_o$ along a programmed path of electrodes on the array until it reaches a preselected destination electrode $E_f$. Destination electrode $E_f$ can be a location on the array at which a subsequent process such as analysis, reaction, incubation, or detection is programmed to occur. In such a case, the flow path over which combined droplet D is actively mixed, indicated by the arrow, also serves as the analysis flow path over which the sample is transported from the input to the processing area on the array. The number of electrodes comprising the selected path from starting electrode $E_o$ to destination electrode $E_f$ corresponds to the number of actuations to which combined droplet D is subject. Hence, through the use of a sufficient number of intermediate path electrodes, combined droplet D will be fully mixed by the time it reaches destination electrode $E_f$. It will be noted that the flow path does not reverse as in the case of the aforedescribed oscillatory mixing techniques. The flow path can, however include one or more right-angle turns through the x-y plane of the array as indicated by the respective arrows in FIGS. 10A-10C. In some cases, turning the path produces unique flow patterns that enhance the mixing effect. In FIG. 10B, the flow path has a ladder or step structure consisting of a number of right-angle turns. In FIG. 10C, destination electrode $E_f$ lies in the same row as starting electrode $E_o$, but combined droplet D is actuated through a flow path that deviates from and subsequently returns to that row in order to increase the number of electrodes over which combined droplet D travels and the number of turns executed.

Referring now to FIG. 11, an example of a two-dimensional linear mixing strategy is illustrated. One electrode row $E_{ROW}$ and one electrode column $E_{COL}$ of the array are utilized. Droplets $D_1$ and $D_2$ are moved toward each other along electrode row $E_{ROW}$ and merged as described hereinabove, forming a merged droplet $D_3$ centered on the electrode disposed at the intersection of electrode row $E_{ROW}$ and electrode column $E_{COL}$. Selected electrodes of electrode column $E_{COL}$ are then sequentially energized and de-energized in the manner described hereinabove to split merged droplet $D_3$ into split droplets $D_4$ and $D_5$. Split droplets $D_4$ and $D_5$ are then moved along electrode column $E_{COL}$. This continued movement of split droplets $D_4$ and $D_5$ enhances the mixing effect on the contents of split droplets $D_4$ and $D_5$.

Referring now to FIGS. 12A and 12B, examples of two-dimensional loop mixing strategies are illustrated. In FIG. 12A, a combined droplet D is circulated clockwise or counterclockwise in a circular, square or other closed loop path along the electrodes of selected rows and columns of the array, as indicated by the arrow. This cyclical actuation of combined droplet D is effected through appropriate sequencing of the electrodes comprising the selected path. Combined droplet D is cycled in this manner for a number of times sufficient to mix its contents. The cycling of combined droplet D produces nonreversible flow patterns that enhance the mixing effect and reduce the time required for complete mixing. In FIG. 12A, the path circumscribes only one central electrode not used for actuation, although the path could be made larger so as to circumscribe more central electrodes.

In FIG. 12B, a sub-array of at least four adjacent electrodes $E_1$-$E_4$ is utilized. Combined droplet D is large enough to overlap all four electrodes $E_1$-$E_4$ of the sub-array simultaneously. The larger size of combined droplet D could be the result of merging two smaller-sized droplets without splitting, or could be the result of first merging two pairs of droplets and thereafter combining the two merged droplets. Combined droplet D is rotated around the sub-array by sequencing electrodes $E_1$-$E_4$ in the order appropriate for effecting either clockwise or counterclockwise rotation. As compared with the mixing strategy illustrated in FIG. 12A, however, a portion of the larger-sized combined droplet D remains "pinned" at or near the intersection of the four electrodes $E_1$-$E_4$ of the sub-array. Thus, combined droplet D in effect rotates or spins about the intersecting region where the pinned portion is located. This effect gives rise to unique internal flow patterns that enhance the mixing effect attributed to rotating or spinning combined droplet D and that promote nonreversible flow. Moreover, the ability to mix combined droplet D using only four electrodes $E_1$-$E_4$ enables the cyclical actuation to occur at high frequencies and with less power requirements.

The mixing strategy illustrated in FIG. 12B can also be implemented using other sizes of arrays. For instance, a 2×4 array has been found to work well in accordance with the invention.

For all of the above-described mixing strategies, it will be noted the droplets involved can be of equal size or unequal volumes. In a situation where an n:1 volume ratio of mixing is required, the electrode areas can be proportionately chosen to yield a one-droplet (n) to one-droplet (1) mixing.

FIG. 13 depicts graphical data illustrating the performance of the one-dimensional linear mixing strategy. The time for complete mixing is plotted as a function of frequency of droplet oscillation (i.e., the switch time between one electrode and a neighboring electrode). Curves are respectively plotted for the 2-electrode (see FIG. 9A), 3-electrode (see FIG. 9B), and 4-electrode (see FIG. 9C) mixing configurations. Mixing times were obtained for 1, 2, 4, 8, and 16 Hz frequencies. The actuation voltage applied to each electrode was 50 V. It was observed that increasing the frequency of switching results in faster mixing times. Similarly, for a given frequency, increasing the number of electrodes also results in improved mixing. It was concluded that increasing the number of electrodes on which the oscillation of the merged droplets is performed increases the number of multi-laminate configurations generated within the droplet, thereby increasing the interfacial area available for diffusion.

FIG. 14 depicts graphical data illustrating the performance of the two-dimensional loop mixing strategy in which the droplet is large enough to overlap the 2×2 electrode sub-array (see FIG. 12B). Mixing times were obtained for 8, 16, 32, and 64 Hz frequencies. As in the experiment that produced the plot of FIG. 13, the actuation voltage applied to each electrode was 50 V. It was concluded that two-dimensional mixing reduces the effect of flow reversibility associated with one-dimensional mixing. Moreover, the fact that the droplet rotates about a point enabled the switching frequency to be increased up to 64 Hz for an actuation voltage of 50 V. This frequency would not have been possible in a one-dimensional linear actuation case at the same voltage. It is further believed that the fact that the droplet overlaps all four electrodes simultaneously enabled droplet transport at such high frequencies and low voltages. The time between the sequential firing of any two adjacent electrodes of the 2×2 sub-array can be reduced because the droplet is in electrical communication with both electrodes simultaneously. That is, the lag time and distance needed for the droplet to physically move from one electrode to another is reduced. Consequently, the velocity of the droplet can be increased in the case of two-dimensional mixing, allowing vortices to form and thereby promoting mixing.

7.4 Droplet-Based Sampling and Processing

Referring now to FIGS. 15A and 15B, a method for sampling and subsequently processing droplets from a continuous-flow fluid input source 61 is schematically illustrated in accordance with the invention. More particularly, the method enables the discretization of uniformly-sized sample droplets S from continuous-flow source 61 by means of electrowetting-based techniques as described hereinabove, in preparation for subsequent droplet-based, on-chip and/or off-chip procedures (e.g., mixing, reacting, incubation, analysis, detection, monitoring, and the like). In this context, the term "continuous" is taken to denote a volume of liquid that has not been discretized into smaller-volume droplets. Non-limiting examples of continuous-flow inputs include capillary-scale streams, fingers, slugs, aliquots, and metered doses of fluids introduced to a substrate surface or other plane from an appropriate source or dispensing device. Sample droplets S will typically contain an analyte substance of interest (e.g., a pharmaceutical molecule to be identified such as by mass spectrometry, or a known molecule whose concentration is to be determined such as by spectroscopy). The several sample droplets S shown in FIGS. 15A and 15B represent either separate sample droplets S that have been discretized from continuous-flow source 61, or a single sample droplet S movable to different locations on the electrode array over time and along various analysis flow paths available in accordance with the sequencing of the electrodes.

The method can be characterized as digitizing analytical signals from an analog input to facilitate the processing of such signals. It will be understood that the droplet-manipulative operations depicted in FIGS. 15A and 15B can advantageously occur on an electrode array as described hereinabove. Such array can be fabricated on or embedded in the surface of a microfluidic chip, with or without other features or devices ordinarily associated with IC, MEMS, and microfluidic technologies. Through appropriate sequencing and control of the electrodes of the array such as through communication with an appropriate electronic controller, sampling (including droplet formation and transport) can be done on a continuous and automated basis.

In FIG. 15A, the liquid input flow of continuous-flow source 61 is supplied to the electrode array at a suitable injection point. Utilizing the electrowetting-based techniques described hereinabove, continuous liquid flow 61 is fragmented or discretized into a series or train of sample droplets S of uniform size. One or more of these newly formed sample droplets S can then be manipulated according to a desired protocol, which can include one or more of the fundamental MOVE, MERGE, MIX and/or SPLIT operations described hereinabove, as well as any operations derived from these fundamental operations. In particular, the invention enables sample droplets S to be diverted from continuous liquid input flow 61 for on-chip analysis or other on-chip processing. For example, FIG. 15A shows droplets being transported along programmable analysis flow paths across the microfluidic chip to one or more functional cells or regions situated on the surface of microfluidic chip such as cells 63 and 65.

Functional cells 63 and 65 can comprise, for example, mixers, reactors, detectors, or storage areas. In the case of mixers and reactors, sample droplets S are combined with additive droplets $R_1$ and/or $R_2$ that are supplied from one or more separate reservoirs or injection sites on or adjacent to the microfluidic chip and conveyed across the microfluidic chip according to the electrowetting technique. In the case of mixers, additive droplets $R_1$ and/or $R_2$ can be other sample substances whose compositions are different from sample droplets S. Alternatively, when dilution of sample droplets S is desired, additive droplets $R_1$ and/or $R_2$ can be solvents of differing types. In the case of reactors, additive droplets $R_1$ and/or $R_2$ can contain chemical reagents of differing types. For example, the electrode array or a portion thereof could be employed as a miniaturized version of multi-sample liquid handling/assaying apparatus, which conventionally requires the use of such large components as 96-well microtitre plates, solvent bottles, liquid transfer tubing, syringe or peristaltic pumps, multi-part valves, and robotic systems.

Functional cells 63 and 65 preferably comprise one or more electrode-containing unit cells on the array. Such functional cells 63 and 65 can in many cases be defined by the sequencing of their corresponding control electrodes, where the sequencing is programmed as part of the desired protocol and controlled by an electronic control unit communicating with the microfluidic chip. Accordingly, functional cells 63 and 65 can be created anywhere on the electrode array of the microfluidic chip and reconfigured on a real-time basis. For example, FIG. 16 illustrates a mixer cell, generally designated MC, that can be created for mixing or diluting a sample droplet S with an additive droplet R according to any of the mixing strategies disclosed herein. Mixer cell MC comprises a 5×3 matrix of electrode-containing unit cells that could be part of a larger electrode array provided by the chip. Mixer cell MC is thus rendered from five electrode/cell rows ROW1-ROW5 and three electrode/cell columns COL1-COL3. MERGE and SPLIT operations can occur at the centrally located electrodes $E_1$-$E_3$ as described hereinabove with reference to FIGS. 5A-6C. The electrodes associated with outer columns COL1 and COL3 and outer rows ROW1 and ROW5 can be used to define transport paths over which sample droplet S and additive droplet R are conveyed from other areas of the electrode array, such as after being discretized from continuous-flow source 61 (see FIG. 15A or 15B). A 2×2 sub-array can be defined for implementing two-dimensional loop mixing processes as illustrated in FIG. 12B. During a MIX, MERGE, SPLIT, or HOLD operation, some or all of the electrodes associated with outer columns COL1 and COL3 and outer rows ROW1 and ROW5 can be grounded to serve as gates and thus isolate mixer cell MC from other areas on the chip. If necessary, complete or substantially complete mixing can be accomplished by a passive mechanism such as diffusion, or by an active mechanism such as by moving or "shaking" the combined droplet according to electrowetting as described hereinabove. The invention contemplates providing other types of functional cells, including functional cells that are essentially miniaturized embodiments or emulations of traditional, macro-scale devices or instruments such as reactors, detectors, and other analytical or measuring instruments. For example, a droplet could be isolated and held in a single row or column of the main electrode array, or at a cell situated off the main array, to emulate a sample holding cell or flow cell through which a beam of light is passed in connection with known optical spectroscopic techniques. A light beam of an initial intensity could be provided from an input optical fiber and passed through the droplet contained by the sample cell. The attenuated light beam leaving the droplet could then enter an output optical fiber and routed to an appropriate detection apparatus such as a photocell. The optical fibers could be positioned on either side of the sample cell, or could be provided in a miniature dip probe that is incorporated with or inserted into the sample cell.

Referring back to FIG. 15A, upon completion of a process executed at a functional cell (e.g., cell 63 or 65), the resulting product droplets (not shown) can be conveyed to respective reservoirs 67 or 69 located either on or off the microfluidic chip for the purpose of waste collection, storage, or output. In addition, sample droplets S and/or product droplets can be recombined into a continuous liquid output flow 71 at a suitable output site on or adjacent to the microfluidic chip for the purposes of collection, waste reception, or output to a further process. Moreover, the droplets processed by functional cell 63 or 65 can be prepared sample droplets that have been diluted and/or reacted in one or more steps, and then transported by electrowetting to another portion of the chip dedicated to detection or measurement of the analyte. Some detection sites can, for example, contain bound enzymes or other biomolecular recognition agents, and be specific for particular analytes. Other detection sites can consist of a general means of detection such as an optical system for fluorescence- or absorbance-based assays, an example of which is given hereinabove.

In the alternative embodiment shown in FIG. 15B, continuous liquid flow 61 is supplied from an input site 61A, and completely traverses the surface of the microfluidic chip to an output site 61B. In this embodiment, sample droplets S are formed (i.e., continuous liquid input flow 61 is sampled) at specific, selectable unit-cell locations along the length of continuous liquid input flow 61 such as the illustrated location 73, and subsequent electrowetting-based manipulations are executed as described hereinabove in relation to the embodiment of FIG. 15A.

The methods described in connection with FIGS. 15A and 15B have utility in many applications. Applications of on-line microfluidic analysis can include, for example, analysis of microdialysis or other biological perfusion flows, environmental and water quality monitoring and monitoring of industrial and chemical processes such as fermentation. Analysis can include the determination of the presence, concentration or activity of any specific substance within the flowing liquid. On-line continuous analysis is beneficial in any application where real-time measurement of a time-varying chemical signal is required, a classic example being glucose monitoring of diabetic patients. Microfluidics reduces the quantity of sample required for an analysis, thereby allowing less invasive sampling techniques that avoid depleting the analyte being measured, while also permitting miniaturized and portable instruments to be realized.

The droplet-based methods of the invention provide a number of advantages over known continuous flow-based microscale methods as well as more conventional macroscale instrument-based methods. Referring to either FIG. 15A or 15B, the flow of sample droplets S from continuous-flow source 61 to the analysis portion of the chip (i.e., the analysis flow) is controlled independently of the continuous flow (i.e., the input flow), thereby allowing a great deal of flexibility in carrying out the analyses. The de-coupling of the analysis flow from the continuous input flow allows each respective flow to be separately optimized and controlled. For example, in microdialysis, the continuous flow can be optimized to achieve a particular recovery rate while the analysis flow is optimized for a particular sensitivity or sampling rate. Reagent droplets R can be mixed with sample droplets S in the analysis flow without affecting or contaminating the main input flow. Sample droplets S in the analysis flow can be stored or incubated indefinitely without interrupting the input flow. Analyses requiring different lengths of time can be carried out simultaneously and in parallel without interrupting the input flow.

In either embodiment depicted in FIG. 15A or 15B, the analysis or other processing of sample droplets S is carried out on-line insofar as the analysis occurs as part of the same sequential process as the input of continuous-flow source 61. However, the analysis is not carried out in-line with respect to continuous liquid input flow 61, because newly formed sample droplets S are diverted away from continuous liquid input flow 61. This design thus allows the analysis flow to be de-coupled from the input flow.

As another advantage, multiple analytes can be simultaneously measured. Since continuous liquid flow 61 is fragmented into sample droplets S, each sample droplet S can be mixed with a different reagent droplet $R_1$ or $R_2$ or conducted to a different test site on the chip to allow simultaneous measurement of multiple analytes in a single sample without cross-talk or cross-contamination. Additionally, multiple step chemical protocols are possible, thereby allowing a wide range of types of analyses to be performed in a single chip.

Moreover, calibration and sample measurements can be multiplexed. Calibrant droplets can be generated and measured between samples. Calibration does not require cessation of the input flow, and periodic recalibration during monitoring is possible. In addition, detection or sensing can be multiplexed for multiple analytes. For example, a single fluorimeter or absorbance detector may be utilized to measure multiple analytes by sequencing the delivery of sample droplets S to the detector site.

Another important advantage is the reconfigurability of the operation of the chip. Sampling rates can be dynamically varied through software control. Mixing ratios, calibration procedures, and specific tests can all be controlled through software, allowing flexible and reconfigurable operation of the chip. Feedback control is possible, which allows analysis results to influence the operation of the chip.

7.5 Droplet-Based Binary Interpolating Digital Mixing

Referring now to FIG. 17, a binary mixing apparatus, generally designated 100, is illustrated in accordance with the invention. Binary mixing apparatus 100 is useful for implementing a droplet-based, variable dilution binary mixing technique in one, two or more mixing phases to obtain desired mixing ratios. The degree of precision of the resulting mixing ratio depends on the number of discrete binary mixing units utilized. As one example, FIG. 17 schematically illustrates a first binary mixing unit 110 and a second binary mixing unit 210. When more than one mixing unit is provided, a buffer 310 is preferably provided in fluid communication with the mixing units to store intermediate products and transfer intermediate products between the mixing units as needed. A suitable electronic controller EC such as a microprocessor capable of executing the instructions of a computer program communicates with first binary mixing unit 110, second binary mixing unit 210, and buffer 310 through suitable communication lines 111, 211, and 311, respectively.

Binary mixing apparatus 100 can be fabricated on a microfluidic chip for the purpose of carrying out binary interpolating digital mixing procedures in accordance with the invention. In designing the physical layouts of the various droplet-handling components of binary mixing apparatus 100 (examples of which are illustrated in FIGS. 18A and 20), electrode design and transportation design (scheduling) were considered. The particular physical layout at least in part determines the code or instruction set executed by electronic controller EC to control the electrodes and thus the types and sequences of droplet-based manipulation to be performed. Preferably, the electrode-containing droplet-handling regions of binary mixing apparatus 100 are structured as shown in the cross-sectional view of FIG. 1, described hereinabove in connection with electrowetting microactuator mechanism 10, or according to a single-sided electrode configurations described hereinbelow. The electrodes of each mixing unit can be sequenced to implement any of the mixing strategies disclosed herein.

The architecture of binary mixing apparatus 100 is designed to take full advantage of accelerated rates observed in droplet-to-droplet mixing experiments, while allowing precisely controlled mixing ratios that can be varied dynamically for multi-point calibrations. As will become evident from the description herein, binary mixing apparatus 100 can handle a wide range of mixing ratios with certain accuracy, and enables mixing patterns that demonstrate high parallelism in the mixing operation as well as scalability in the construction of mixing components in a two-dimensional array. Binary mixing apparatus 100 can handle a wide range of droplet sizes. There is, however, a lower limit on droplet size if sample droplets are being prepared for the purpose of a detection or measurement.

The architecture of binary mixing apparatus 100 is based on the recognition that the most efficient mixing most likely occurs between two droplets moving toward each other. This has been observed from experiments, and could be explained by the fact that convection induced by shear movement of fluids accelerates the mixing process much faster than pure physical diffusion. Thus, as a general design principle, one-by-one mixing is utilized as much as possible. As indicated hereinabove, one-by-one mixing preferably involves both mixing and splitting operations to maintain uniform droplet size. The basic MIX and SPLIT operations have been described hereinabove with reference to FIGS. 5A-6C.

Certain assumptions have been made in design of the architecture of binary mixing apparatus 100, and include the following:

1. Full mixing occurs in terms of chemical and/or physical processes given adequate time.
2. Equal droplet splitting occurs in terms of physical volume and chemical components.
3. Negligible residues are produced during droplet transportation.
4. Mixing time for large dilution ratios is a bottleneck.
5. There are tolerances on mixing ratios.
6. Transportation time is negligible compared to mixing.

Preferred design requirements and constraints were also considered, and include the following:

1. Minimum volume of mixture output to guarantee detectability.
2. Maximum number of independent control electrodes.
3. Maximum mixing area.

4. Maximum number of actuation per electrode.

5. Reconfigurability for different mixing ratios.

Thus, one design objective was to complete the mixing process using a minimum number of mixing-splitting operations while maintaining the accuracy of the mixing ratio.

Moreover, some desirable attributes for an ideal mixing architecture were considered to be as follows:

1. Accurate mixing ratio.

2. Small number of mixing cycles. Since many mixing processes will involve more than one mixing phase, during the first phase the two binary mixing units 110 and 210 are operated in parallel to and independent of each other. The second mixing phase, however, can only start after the first phase is finished. Thus, the total mixing time of two-phase mixing should be the maximum mixing time of first and second binary mixing units 110 and 210 in the first phase plus the mixing time of either first binary mixing unit 110 or second binary mixing unit 210 in the second phase. Accordingly, the mixing cycle is defined as the total mixing time required to finish one mixing process. It is standardized in terms of mixing operations, which are assumed to be the most time consuming operations as compared to, for example, droplet transport.

3. Small number of total mixing operations. A single binary mixing operation that consists of mixing, splitting and/or transportation is a source of error. Also, more mixing operations also mean more usage of the electrodes, which may be another cause of error due to the charge accumulation on electrodes.

4. Simplicity of operations.

5. Scalability. The capability of the binary mixing apparatus 100 to handle different mixing ratios and extendibility of the structure to multiple mixing units when large throughput is demanded.

6. Parallelism.

The architecture of binary mixing apparatus 100 implements multiple hierarchies of binary mixing phases, with the first hierarchy providing the approximate mixing ratio and the following ones employed as the calibration mechanism. The concept is analogous to an interpolating Digital-to-Analog Converter (DAC) whose architecture is divided into two parts, with the main DAC handling the MSB (most significant bit) in a binary manner and the sub-DAC dealing with calibration and correction down to the LSB (least significant bit). An example of a one-phase binary mixing process carried out to produce sixteen sample droplets diluted to a concentration of 1/32 is described hereinbelow with reference to FIGS. 19A-19F.

It is believed that mixing in a binary manner results in dilution to large ratios in the power of two with only a few mixing operations. The accuracy of the ratio can be calibrated by further mixing two intermediate products in a binary manner. For example, one mixing process could produce concentrations of 1/8, and another could produce concentrations of 1/16. When these two mixtures further mix with 1:1, 1:3, 3:1, 1:7, and 7:1 ratios, respectively, the final product would have concentrations of 1/10.67, 1/12.8, 1/9.14, 1/14.2, and 1/8.53, respectively. Based on this principle, any ratio can be obtained in a few mixing phases with acceptable tolerance. If further accuracy is needed, an additional mixing phase using products from the previous phase can be used to calibrate the ratio. As indicated previously, the process of approaching the expected ratio to high accuracy could be characterized as a successive approximation process that is similar to one used in Analog to Digital converter design. It is an approach that trades off speed with accuracy. However, the number of mixing phases required for adequate accuracy is surprisingly small. Generally, when the required ratio is smaller than 32, two mixing phases are often enough. Ratios larger than 32 but smaller than 64 would possibly need three mixing phases. It is also observed that different combinations of intermediate products mixed with a range of binary ratios would produce more interpolating points to further increase the accuracy, thus eliminating the necessities of using extra mixing phases.

Based on known mathematical principles, the architecture of binary mixing apparatus 100 can be designed to have preferably two same-structured mixing units (e.g., first binary mixing unit 110 and second binary mixing unit 210 shown in FIG. 17), with each binary mixing unit 110 and 210 handling binary mixing and generating certain volumes of mixture. Each binary mixing unit 110 and 210 can produce different mixing ratios of a power of two according to different operations. In the first mixing phase, the sample is mixed with the reagent with a ratio of any of the series (1:1, 1:3, 1:7 . . . 1:$2^{n-1}$) using two binary mixing units 110 and 210 in parallel. The products are two mixtures with the same volume. The ratio of the two mixtures is determined by the required ratio of the final product, and preferably is controlled by a computer program. In a second phase, the two mixtures mix with a certain binary ratio in one of the two units. Buffer 310 is used to store some of the intermediate products when second phase mixing is carried out in one of binary mixing units 110 or 210. Since the volume of the intermediate product is limited (e.g., 16 droplets), the second mixing cannot be carried out with an arbitrarily large binary ratio. From the description herein of the structure and operation of binary mixing apparatus 100, it can be demonstrated that the possible binary ratio in the following mixing phase is constrained to be less than or equal to 31, given that 4 columns and 16 droplets are generated from each unit. Even so, sufficient accuracy could be obtained after a second phase. If further accuracy is demanded, additional mixing can be carried out to generate a mixture closer to the requirement, using the product from the second phase and another mixture with power of two series ratio (e.g., a calibration mixture).

From the description above, it can be observed that generating powers of two series mixtures can be a fundamental process in obtaining an expected ratio. The exact ratio of this mixture could be decided ahead of time or varied dynamically. For example, during the first phase of mixing, the two ratios could be calculated ahead of time according to the required ratio. In the phase following the second phase, however, the calibration mixture could be decided dynamically, given the feedback from the quality of previous mixing. Even if predecided, it is likely that extra time would be needed to prepare the calibration mixture before a further phase mixing is carried out. In such a case, the use of only two binary mixing units 110 and 210 might be not enough, and an extra binary mixing unit could be added to prepare the calibration mixture in parallel with the previous calibration mixing process.

The determination of a mixing strategy includes calculating the number of mixing phases and the mixing ratio for each phase according to the required ratio and its tolerance. This determination can be solved by an optimization process with the number of mixing operations and time of the mixing as the objective function.

Referring now to FIGS. 18A and 18B, an exemplary architecture for first binary mixing unit 110 is illustrated, with the understanding that second binary mixing unit 210 and any other additional mixing units provided can be similarly designed. The embodiment shown in FIG. 18A is capable of one-phase mixing, while the embodiment shown in FIG. 20 (to be briefly described hereinbelow) is capable of two-phase mixing. As shown in FIG. 18A, first binary mixing unit 110 generally comprises a 7×7 electrode matrix or array, generally designated EA, consisting of 49 matrix electrodes and their associated cells $E_{ij}$, where "i" designates 1, 2, . . . , 7 rows of electrodes and "j" designates 1, 2, . . . , 7 columns of electrodes. FIG. 18B identifies matrix electrodes $E_{ij}$ of electrode array EA in accordance with a two-dimensional system of rows ROW1-ROW7 and columns COL1-COL7. The invention, however, is not limited to any specific number of electrodes, rows, and columns. A larger or smaller electrode array EA could be provided as appropriate.

Referring back to FIG. 18A, a sample reservoir 113, waste reservoir 115, and reagent reservoir 117 are also provided. Depending on the position of reservoirs 113, 115 and 117 in relation to electrode array EA, a suitable number and arrangement of transport or path electrodes and associated cells $T_1$-$T_4$ are provided for conveying droplets to and from electrode array EA. A number of electrical leads (e.g., L) are connected to matrix electrodes $E_{ij}$ and transport electrodes $T_1$-$T_4$ to control the movement or other manipulation of droplets. It will be understood that electrical leads L communicate with a suitable electronic controller such as a microprocessor (e.g., electronic controller EC in FIG. 17). Each matrix electrode $E_{ij}$ could have its own independent electrical lead connection. However, to reduce the number of electrical leads L and hence simplify the architecture of first binary mixing unit 110, the electrodes of each of columns COL2-COL7 (see FIG. 18B) are connected to common electrical leads L as shown in FIG. 18A. These common connections must be taken into consideration when writing the protocol for mixing operations to be carried out by first binary mixing unit 110.

In effect, each binary mixing unit 110 and 210 of binary mixing apparatus 100 is designed to have 4×4 logic cells with each cell storing the sample, reagent or intermediate mixture. This can be conceptualized by comparing the matrix layout of FIG. 18B with the 4×4 logic cell matrix illustrated in FIGS. 19A-19F. The 4×4 construct accounts for the fact that droplets combine on intermediate control electrodes from adjacent control electrodes (e.g., intermediate control electrode $E_2$ and adjacent control electrodes $E_1$ and $E_3$ in FIGS. 5A-6C), the mixed droplet is then split, and the newly formed mixed droplets are then returned to the adjacent control electrodes at the completion of the MIX (or MIX-SPLIT) operation. Hence, certain rows of electrodes need only be used as temporary intermediate electrodes during the actual droplet combination event. The construct also accounts for the fact that certain columns of electrodes need only be used for droplet transport (e.g., shifting droplets from one column to another to make room for the addition of new reagent droplets). In view of the foregoing, electrode rows ROW2, ROW4 and ROW6, and columns COL2, COL4 and COL6 in FIG. 18B are depicted simply as lines in FIGS. 19A-19F. Also in FIGS. 19A-19F, active electrodes are indicated by shaded bars, mixing operations are indicated by the symbol "- - - -> <- - - -", and transport operations are indicated by the symbol "- - - ->". Additionally, droplet concentrations are indicated by numbers (e.g., 0, 1, ½) next to rows and columns where droplets reside.

It can be seen that one-by-one mixing can occur between some of the adjacent cells in horizontal or vertical directions (from the perspective of the drawing sheets containing FIGS. 19A-19F), depending on whether active electrodes exist between the two cells. In the first column, between any of the two adjacent row cells containing droplets, an active electrode exists that allows the two adjacent row cells to perform mixing operations. In other columns, there are no active electrodes between two row cells. This is illustrated, for example, in FIG. 19A. Between any of the columns containing droplets, electrodes exist that allow any of the cells in one column to conduct a mixing operation with the cells of its adjacent column simultaneously. This is illustrated, for example, in FIG. 19D. By the use of the active electrodes, the content of a logic cell (i.e., a droplet) can move from one row to another in the first column, or move between columns. The employment of the 4×4 logic structure is designed for the optimization of binary operations, as demonstrated by the following example. It will be noted that the volume output of the present one-mixing-unit embodiment of first binary mixing unit 110 is limited to 16 droplets, although the physical volume of the final product can be adjusted by changing the size of each droplet.

To demonstrate how binary mixing apparatus 100 can produce any of the power of two ratios, FIGS. 19A-19F illustrate an example of a series of mixing operations targeting a 1:31 ratio (equal to ⅟32 concentration). It can be seen that the mixing process has two basic stages: a row mix and a column mix. Generally, the purpose of the row mix is to approach the range of the mixing ratio with a minimum volume of two mixing inputs. The purpose of the column mix is to produce the required volume at the output and at the same time obtain another four-fold increase in ratio. Thus, as indicated in FIGS. 19A-19F, to obtain a 1:31 ratio, the row mix results in a 1:7 ratio or ⅛ concentration (see FIG. 19D). The column mix assists in achieving the final product ratio of 1:31 or ⅟32 concentration (see FIG. 19F).

Figure 19A:
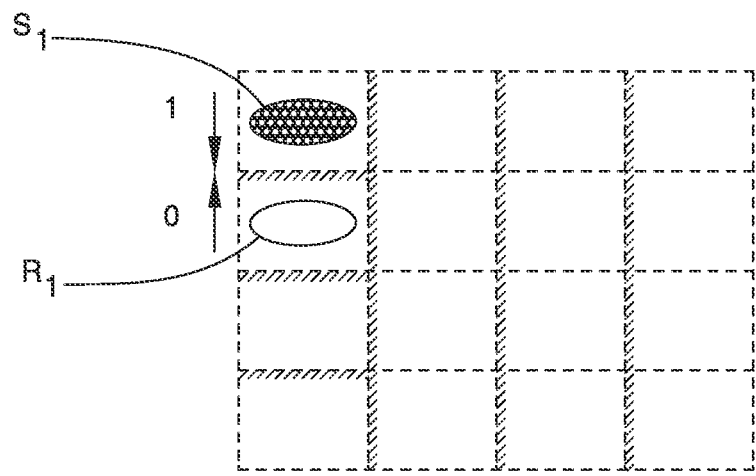
Figure 19B:
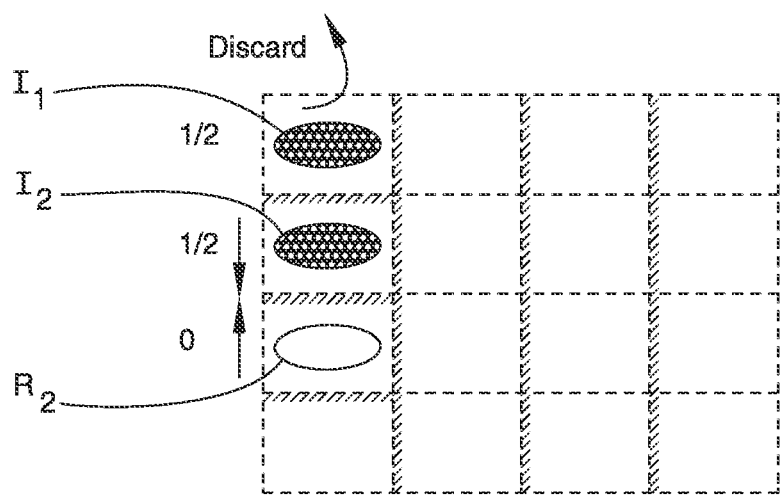
Figure 19C:
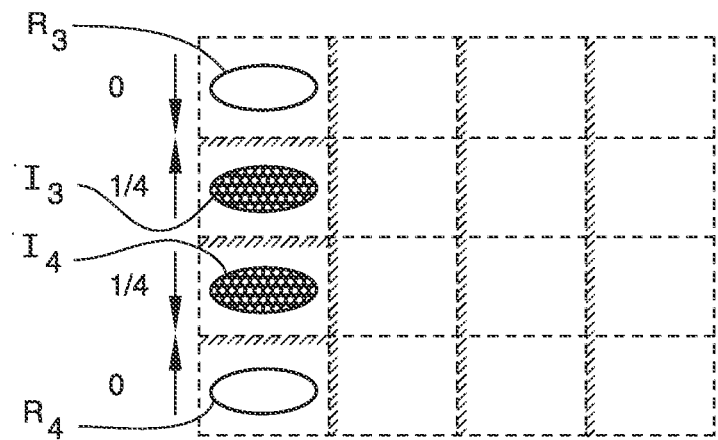

Referring specifically to FIG. 19A, a single row mix is performed by combining a sample droplet $S_1$ having a concentration of 1 (i.e., 100%) with a reagent (or solvent) droplet $R_1$ having a concentration of 0. This results in two intermediate-mixture droplets $I_1$ and $I_2$, each having a ½ concentration as shown in FIG. 19B. One of the intermediate-mixture droplets (e.g., $I_1$) is discarded, and a new reagent droplet $R_2$ is moved to the logic cell adjacent to the remaining intermediate-mixture droplet (e.g., $I_2$). Another row mix is performed by combining intermediate-mixture droplet $I_2$ and reagent droplet $R_2$. This results two intermediate-mixture droplets $I_3$ and $I_4$, each having a ¼ concentration as shown in FIG. 19C. Two new reagent droplets $R_3$ and $R_4$ are then added and, in a double row mix operation, combined with respective intermediate-mixture droplets $I_3$ and $I_4$. This results in four intermediate-mixture droplets $I_5$-$I_8$, each having a ⅛ concentration as shown in FIG. 19D.

Figure 19D:
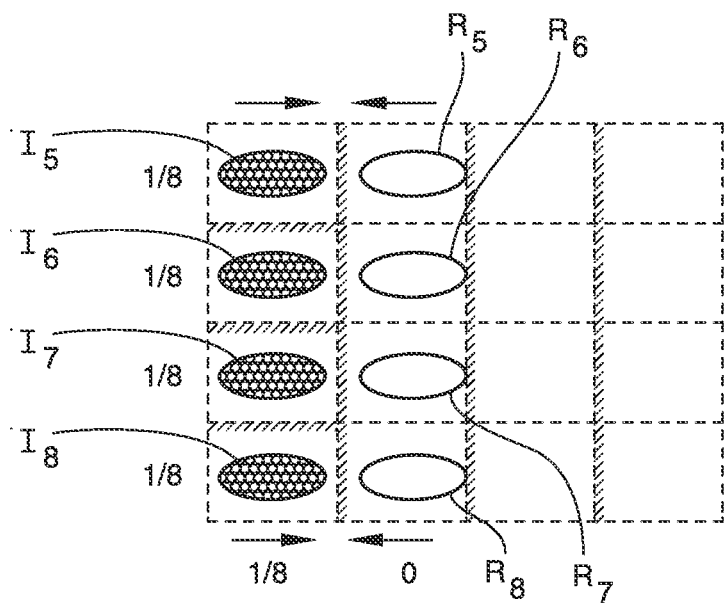
Figure 19E:
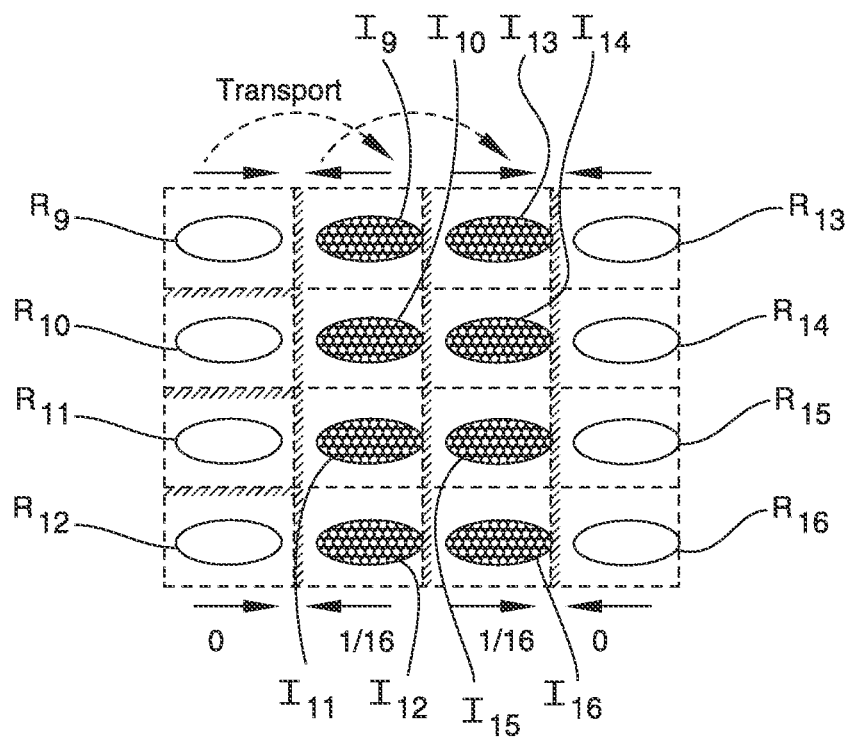

As also shown in FIG. 19D, four new reagent droplets $R_5$-$R_8$ are then moved onto the matrix adjacent to respective intermediate-mixture droplets $I_5$-$I_8$. A column mix is then performed as between each corresponding pair of intermediate-mixture droplets $I_5$-$I_8$ and reagent droplets $R_5$-$R_8$. This produces eight intermediate-mixture droplets $I_9$-$I_{16}$, each having a ⅟16 concentration as shown in FIG. 19E. As also shown in FIG. 19E, each column of four intermediate-mixture droplets, $I_9$-$I_{12}$ and $I_{13}$-$I_{16}$, respectively, is shifted over one column to the right to enable two columns of new reagent droplets, $R_9$-$R_{12}$ and $R_{13}$-$R_{16}$, respectively, to be loaded onto the outer columns of the matrix. Each corresponding pair of intermediate-mixture droplets and reagent droplets (e.g., $I_9$ and $R_9$, $I_{10}$ and $R_{10}$, etc.) is then combined through additional column mix operations.

Figure 19F:
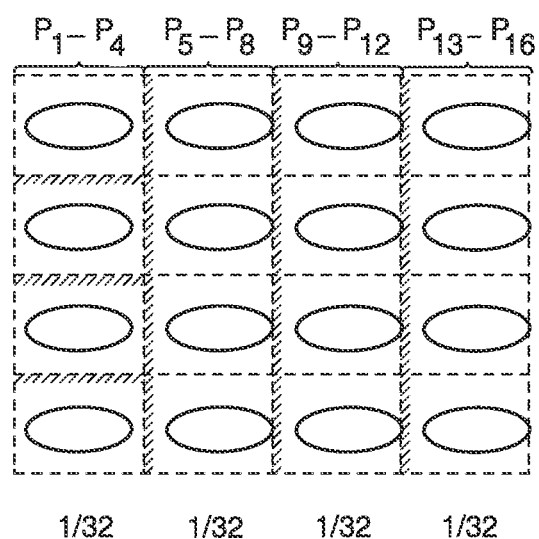

As a result of these mixing operations, sixteen final-mixture product droplets $P_1$-$P_{16}$, are produced, each having a final concentration of ⅟32 (corresponding to the target mix ratio of 1:31) as shown in FIG. 19F. Product droplets $P_1$-$P_{16}$ are now prepared for any subsequent operation contemplated, such sampling, detection, analysis, and the like as described by way of example hereinabove. Additionally, depending on the precise mix ratio desired, product droplets $P_1$-$P_{16}$ can be subjected to a second or even a third phase of mixing operations if needed as described hereinabove. Such additional mixing phases can occur at a different area on the electrode array of which first binary mixing unit 110 could be a part. Alternatively, as illustrated in FIG. 17, the final-mixture droplets can be conveyed to another binary mixing apparatus (e.g., second binary mixing unit 210) that fluidly communicates directly with first binary mixing unit 110 or through buffer 310.

The method of the invention can be applied to ratios less than or greater than 31. For example, if the goal is to obtain a ratio of 1:15, the row mix would mix the input to a ratio of 1:3, which would require two mixing operations instead of three for obtaining a mixing ratio of 1:7. In terms of mixing operations, FIGS. 19A-19F can be used to show that the first stage for row mix (single) and the discard operation for the second stage could be eliminated in such a case.

To further explain the detailed operations for completing the mixing of 1:31, a pseudo code for the example specifically illustrated in FIGS. 19A-19F (and with general reference to FIG. 18B) is listed as follows:

1. Load S (1,1), Load R (2,1), Row Mix 1,2
2. (Discard (1,1), Load R (3,1)), Row Mix 2,3
3. Load R (1,1) Load R (3,1), (Row Mix 1,2, Row Mix 3,4)
4. Column Load R2, Column Mix 1,2
5. Column Move 2 to 3, Column Move 1 to 2, column Load R1. Column Load R4, (Column Mix 1,2 Column Mix 3,4)
6. Finish The above pseudo code also standardizes the possible mixing operations into one mixing process. The sequence of the operations is subject to more potential optimization to increase the throughput of the mixing while decreasing the number of mixing operations. This design also keeps in mind that the number of active electrodes should be maintained as small as possible while making sure all the mixing operations function properly. In the preferred embodiment, each binary mixing unit 110 and 210 (see FIG. 17) is designed to have 13 active electrodes to handle the mixing functions. The capability of transporting the droplets into and inside the each binary mixing unit 110 and 210 is another consideration. Initially, the two outside columns of the array could be used as transportation channels running along both sides of the mixer to deliver droplets into the mixer simultaneously with other operations of the mixer. The same number of electrodes can also handle these transportation functions.

The second phase is the mixing process when the intermediate products from two binary mixing units 110 and 210 (see FIG. 17) are to be mixed. It is similar to the standard binary mixing process in the first phase described hereinabove with reference to FIGS. 19A-19F. The only difference is that the second-phase mixing is carried out in one of binary mixing units 110 and 210 holding the previous mixing product (e.g., product droplets $P_1$-$P_{16}$ shown in FIG. 19F). As indicated previously, buffer 310 is used to hold some of the product during the process.

It can be calculated that the maximum ratio of mixing during the second phase is limited to 31. The reason is that to obtain the maximum ratio, row mixing should be used as much as possible. When row mixing is used to increase the ratio, less input is lost during the discard process. Thus, when there are finite amounts of input material, the first choice is to see how far the row mixing can go until there is just enough volume left to fulfill the requirement for mixture output. In this way, it could be known that two mixtures with 16 droplets can only mix with the largest ratio of 1:31 when the output requirement is specified to no less than 16 droplets. It can also be demonstrated from FIGS. 19A-19F that to mix with a ratio of 1:31, 16 droplets of reagents would be the minimum amount.

The physical layout for first binary mixing unit 110 illustrated in FIG. 18A can be modified to better achieve two-phase mixing capability. Accordingly, referring now to FIG. 20, a two-phase mixing unit, generally designated 410, is illustrated. The architecture of two-phase mixing unit 410 is similar to that of first binary mixing unit 110 of FIG. 18A, and thus includes the 7×7 matrix, a sample reservoir 413, a waste reservoir 415, a reagent reservoir 417, and an appropriate number and arrangement of off-array electrodes as needed for transport of droplets from the various reservoirs to the 7×7 matrix. Two-phase mixing unit 410 additionally includes a cleaning reservoir 419 to supply cleaning fluid between mixing processes, as well as an outlet site 421 for transporting product droplets to other mixing units or to buffer 310 (see FIG. 17). Moreover, it can be seen that additional rows and columns of electrodes are provided at the perimeter of the 7×7 matrix to provide transport paths for droplets to and from the matrix.

Further insight into the performance of the architecture of binary mixing apparatus 100 can be obtained by considering the TABLE set forth hereinbelow. This TABLE was constructed to list all the possible interpolating mixing ratios using a two-phase mixing strategy for a maximum mixing ratio of 63 (or, equivalently, a maximum concentration of 1/64). The corresponding mixing parameters, such as the mixing ratio for mixing unit 1 and 2 (e.g., first and second binary mixing units 110 and 210) in the first phase, the mixing ratio for the second phase, and the total mixing cycles are also recorded. The TABLE can serve as a basis for selecting the proper mixing strategy and/or further optimization in terms of trading off accuracy with time, improving resource usage when multiple mixers exist, decreasing total mixing operations, improving parallelism, and so on. The TABLE can be provided as a look-up table or data structure as part of the software used to control apparatus 100.

The TABLE shows that there are a total of 196 mixing strategies using the architecture of the invention, which corresponds to 152 unique mixing points. The 196 mixing strategies are calculated by interpolating any possible combinations of two mixtures with power of two ratios under 63. These points have non-linear instead of linear intervals. The smaller the ratio, the smaller the interval. The achievable points are plotted in FIG. 21. It is evident from the TABLE that the number of achievable ratios is larger than traditional linear mixing points and the distribution is more reasonable. In addition, certain volumes of output other than one droplet can allow more tolerance on the error caused by one-by-one mixing. In terms of mixing cycles, the best performance is for mixing ratios of the power of two compared to their nearby ratios. In terms of accuracy, the larger the ratio, generally the worse the performance, since a smaller number of interpolating points can be achieved.

It can be observed from the two-phase mix ing plan plotted in FIG. 21 that there are not enough points when the target ratio is larger than 36. FIG. 21 shows that there is no point around a ratio of 40. The difference between the target and theoretical achievable ratio could amount to 3. However, by careful examination of the achievable points around 40, an appropriate usage of the remaining mixture from phase one to further calibrate the available points can result in several additional interpolating points between 36.5714 and 42.6667, where the largest error exists from the phase two mixing plan. For instance, the mixing plan #183 in the TABLE calls for obtaining mixture 1 and mixture 2 with ratios of 1:31 and 1:63, respectively, then mixing them with a ratio of 3:1. It is known that there are ¾ parts of mixture 2 left. So it is possible to mix the mixture from phase two with a concentration of 36.517 with mixture 2 of concentration 63 using ratio of 3:1, 7:1, etc. That leads to a point at 40.9, 38.5, etc. In such manner, more accuracy is possible with an additional mixing phase, but with only a small increase in mixing cycles (two and three cycles, respectively, in this example), and at the expense of no additional preparation of calibration mixture.

FIG. 22 demonstrates all the achievable points by one-phase, two-phase, and three-phase mixing plans. The total number of points is 2044. The points achieved by phase three are obtained by using the product from phase two and remaining products from phase one. They are calculated by considering the volume of the remaining product from phase one after phase two has finished and reusing them to mix with products from phase two. The possible mixing ratios of phase three are determined by the mixing ratio of phase two.

TABLE

| Mix Plan Number | Target Mix Ratio | Mix Unit 1 Mix Ratio | Mix Unit 2 Mix Ratio | Phase 2 Mix Ratio | Total Mix Cycles |
|---|---|---|---|---|---|
| 1 | 1.0159 | 1:0 | 1:1 | 31:1 | 6 |
| 2 | 1.0240 | 1:0 | 1:3 | 31:1 | 7 |
| 3 | 1.0281 | 1:0 | 1:7 | 31:1 | 8 |
| 4 | 1.0302 | 1:0 | 1:15 | 31:1 | 9 |
| 5 | 1.0312 | 1:0 | 1:31 | 31:1 | 10 |
| 6 | 1.0317 | 1:0 | 1:63 | 31:1 | 11 |
| 7 | 1.0323 | 1:0 | 1:1 | 15:1 | 5 |
| 8 | 1.0492 | 1:0 | 1:3 | 15:1 | 6 |
| 9 | 1.0579 | 1:0 | 1:7 | 15:1 | 7 |
| 10 | 1.0622 | 1:0 | 1:15 | 15:1 | 8 |
| 11 | 1.0644 | 1:0 | 1:31 | 15:1 | 9 |
| 12 | 1.0656 | 1:0 | 1:63 | 15:1 | 10 |
| 13 | 1.0667 | 1:0 | 1:1 | 7:1 | 4 |
| 14 | 1.1034 | 1:0 | 1:3 | 7:1 | 5 |
| 15 | 1.1228 | 1:0 | 1:7 | 7:1 | 6 |
| 16 | 1.1327 | 1:0 | 1:15 | 7:1 | 7 |
| 17 | 1.1378 | 1:0 | 1:31 | 7:1 | 8 |
| 18 | 1.1403 | 1:0 | 1:63 | 7:1 | 9 |
| 19 | 1.1429 | 1:0 | 1:1 | 3:1 | 3 |
| 20 | 1.2308 | 1:0 | 1:3 | 3:1 | 4 |
| 21 | 1.2800 | 1:0 | 1:7 | 3:1 | 5 |
| 22 | 1.3061 | 1:0 | 1:15 | 3:1 | 6 |
| 23 | 1.3196 | 1:0 | 1:31 | 3:1 | 7 |
| 24 | 1.3264 | 1:0 | 1:63 | 3:1 | 8 |
| 25 | 1.3333 | 1:0 | 1:1 | 1:1 | 2 |
| 26 | 1.6000 | 1:0 | 1:1 | 1:3 | 3 |
| 27 | 1.6000 | 1:0 | 1:3 | 1:1 | 3 |
| 28 | 1.7778 | 1:0 | 1:1 | 1:7 | 4 |
| 29 | 1.7778 | 1:0 | 1:7 | 1:1 | 4 |
| 30 | 1.8824 | 1:0 | 1:1 | 1:15 | 5 |
| 31 | 1.8824 | 1:0 | 1:15 | 1:1 | 5 |
| 32 | 1.9394 | 1:0 | 1:1 | 1:31 | 6 |
| 33 | 1.9394 | 1:0 | 1:31 | 1:1 | 6 |

TABLE-continued

| Mix Plan Number | Target Mix Ratio | Mix Unit 1 Mix Ratio | Mix Unit 2 Mix Ratio | Phase 2 Mix Ratio | Total Mix Cycles |
|---|---|---|---|---|---|
| 34 | 1.9692 | 1:0 | 1:63 | 1:1 | 7 |
| 35 | 2.0000 | 1:1 | N/A | N/A | 1 |
| 36 | 2.0317 | 1:1 | 1:3 | 31:1 | 7 |
| 37 | 2.0480 | 1:1 | 1:7 | 31:1 | 8 |
| 38 | 2.0562 | 1:1 | 1:15 | 31:1 | 9 |
| 39 | 2.0604 | 1:1 | 1:31 | 31:1 | 10 |
| 40 | 2.0624 | 1:1 | 1:63 | 31:1 | 11 |
| 41 | 2.0645 | 1:1 | 1:3 | 15:1 | 6 |
| 42 | 2.0981 | 1:1 | 1:7 | 15:1 | 7 |
| 43 | 2.1157 | 1:1 | 1:15 | 15:1 | 8 |
| 44 | 2.1245 | 1:1 | 1:31 | 15:1 | 9 |
| 45 | 2.1289 | 1:1 | 1:63 | 15:1 | 10 |
| 46 | 2.1333 | 1:1 | 1:3 | 7:1 | 5 |
| 47 | 2.2069 | 1:1 | 1:7 | 7:1 | 6 |
| 48 | 2.2456 | 1:1 | 1:15 | 7:1 | 7 |
| 49 | 2.2655 | 1:1 | 1:31 | 7:1 | 8 |
| 50 | 2.2756 | 1:1 | 1:63 | 7:1 | 9 |
| 51 | 2.2857 | 1:0 | 1:3 | 1:3 | 4 |
| 52 | 2.2857 | 1:1 | 1:3 | 3:1 | 4 |
| 53 | 2.4615 | 1:1 | 1:7 | 3:1 | 5 |
| 54 | 2.5600 | 1:1 | 1:15 | 3:1 | 6 |
| 55 | 2.6122 | 1:1 | 1:31 | 3:1 | 7 |
| 56 | 2.6392 | 1:1 | 1:63 | 3:1 | 8 |
| 57 | 2.6667 | 1:1 | 1:3 | 1:1 | 3 |
| 58 | 2.9091 | 1:0 | 1:3 | 1:7 | 5 |
| 59 | 2.9091 | 1:0 | 1:7 | 1:3 | 5 |
| 60 | 3.2000 | 1:1 | 1:3 | 1:3 | 4 |
| 61 | 3.2000 | 1:1 | 1:7 | 1:1 | 4 |
| 62 | 3.3684 | 1:0 | 1:3 | 1:15 | 6 |
| 63 | 3.3684 | 1:0 | 1:15 | 1:3 | 6 |
| 64 | 3.5556 | 1:1 | 1:3 | 1:7 | 5 |
| 65 | 3.5556 | 1:1 | 1:15 | 1:1 | 5 |
| 66 | 3.6571 | 1:0 | 1:3 | 1:31 | 7 |
| 67 | 3.6571 | 1:0 | 1:31 | 1:3 | 7 |
| 68 | 3.7647 | 1:1 | 1:3 | 1:15 | 6 |
| 69 | 3.7647 | 1:1 | 1:31 | 1:1 | 6 |
| 70 | 3.8209 | 1:0 | 1:63 | 1:3 | 8 |
| 71 | 3.8788 | 1:1 | 1:3 | 1:31 | 7 |
| 72 | 3.8788 | 1:1 | 1:63 | 1:1 | 7 |
| 73 | 4.0000 | 1:3 | N/A | N/A | 3 |
| 74 | 4.0635 | 1:3 | 1:7 | 31:1 | 8 |
| 75 | 4.0960 | 1:3 | 1:15 | 31:1 | 9 |
| 76 | 4.1124 | 1:3 | 1:31 | 31:1 | 10 |
| 77 | 4.1207 | 1:3 | 1:63 | 31:1 | 11 |
| 78 | 4.1290 | 1:3 | 1:7 | 15:1 | 7 |
| 79 | 4.1967 | 1:3 | 1:15 | 15:1 | 8 |
| 80 | 4.2314 | 1:3 | 1:31 | 15:1 | 9 |
| 81 | 4.2490 | 1:3 | 1:63 | 15:1 | 10 |
| 82 | 4.2667 | 1:0 | 1:7 | 1:7 | 6 |
| 83 | 4.2667 | 1:3 | 1:7 | 7:1 | 6 |
| 84 | 4.4138 | 1:3 | 1:15 | 7:1 | 7 |
| 85 | 4.4912 | 1:3 | 1:31 | 7:1 | 8 |
| 86 | 4.5310 | 1:3 | 1:63 | 7:1 | 9 |
| 87 | 4.5714 | 1:1 | 1:7 | 1:3 | 5 |
| 88 | 4.5714 | 1:3 | 1:7 | 3:1 | 5 |
| 89 | 4.9231 | 1:3 | 1:15 | 3:1 | 6 |
| 90 | 5.1200 | 1:3 | 1:31 | 3:1 | 7 |
| 91 | 5.2245 | 1:3 | 1:63 | 3:1 | 8 |
| 92 | 5.3333 | 1:3 | 1:7 | 1:1 | 4 |
| 93 | 5.5652 | 1:0 | 1:7 | 1:15 | 7 |
| 94 | 5.5652 | 1:0 | 1:15 | 1:7 | 7 |
| 95 | 5.8182 | 1:1 | 1:7 | 1:7 | 6 |
| 96 | 5.8182 | 1:1 | 1:15 | 1:3 | 6 |
| 97 | 6.4000 | 1:3 | 1:7 | 1:3 | 5 |
| 98 | 6.4000 | 1:3 | 1:15 | 1:1 | 5 |
| 99 | 6.5641 | 1:0 | 1:7 | 1:31 | 8 |
| 100 | 6.5641 | 1:0 | 1:31 | 1:7 | 8 |
| 101 | 6.7368 | 1:1 | 1:7 | 1:15 | 7 |
| 102 | 6.7368 | 1:1 | 1:31 | 1:3 | 7 |
| 103 | 7.1111 | 1:3 | 1:7 | 1:7 | 6 |
| 104 | 7.1111 | 1:3 | 1:31 | 1:1 | 6 |
| 105 | 7.2113 | 1:0 | 1:63 | 1:7 | 9 |
| 106 | 7.3143 | 1:1 | 1:7 | 1:31 | 8 |
| 107 | 7.3143 | 1:1 | 1:63 | 1:3 | 8 |
| 108 | 7.5294 | 1:3 | 1:7 | 1:15 | 7 |
| 109 | 7.5294 | 1:3 | 1:63 | 1:1 | 7 |

TABLE-continued

| Mix Plan Number | Target Mix Ratio | Mix Unit 1 Mix Ratio | Mix Unit 2 Mix Ratio | Phase 2 Mix Ratio | Total Mix Cycles |
|---|---|---|---|---|---|
| 110 | 7.7576 | 1:3 | 1:7 | 1:31 | 8 |
| 111 | 8.0000 | 1:7 | N/A | N/A | 4 |
| 112 | 8.1270 | 1:7 | 1:15 | 31:1 | 9 |
| 113 | 8.1920 | 1:7 | 1:31 | 31:1 | 10 |
| 114 | 8.2249 | 1:7 | 1:63 | 31:1 | 11 |
| 115 | 8.2581 | 1:0 | 1:15 | 1:15 | 8 |
| 116 | 8.2581 | 1:7 | 1:15 | 15:1 | 8 |
| 117 | 8.3934 | 1:7 | 1:31 | 15:1 | 9 |
| 118 | 8.4628 | 1:7 | 1:63 | 15:1 | 10 |
| 119 | 8.5333 | 1:1 | 1:15 | 1:7 | 7 |
| 120 | 8.5333 | 1:7 | 1:15 | 7:1 | 7 |
| 121 | 8.8276 | 1:7 | 1:31 | 7:1 | 8 |
| 122 | 8.9825 | 1:7 | 1:63 | 7:1 | 9 |
| 123 | 9.1429 | 1:3 | 1:15 | 1:3 | 6 |
| 124 | 9.1429 | 1:7 | 1:15 | 3:1 | 6 |
| 125 | 9.8462 | 1:7 | 1:31 | 3:1 | 7 |
| 126 | 10.2400 | 1:7 | 1:63 | 3:1 | 8 |
| 127 | 10.6667 | 1:7 | 1:15 | 1:1 | 5 |
| 125 | 10.8936 | 1:0 | 1:15 | 1:31 | 9 |
| 129 | 10.8936 | 1:0 | 1:31 | 1:15 | 9 |
| 130 | 11.1304 | 1:1 | 1:15 | 1:15 | 8 |
| 131 | 11.1304 | 1:1 | 1:31 | 1:7 | 8 |
| 132 | 11.6364 | 1:3 | 1:15 | 1:7 | 7 |
| 133 | 11.6364 | 1:3 | 1:31 | 1:3 | 7 |
| 134 | 12.8000 | 1:7 | 1:15 | 1:3 | 6 |
| 135 | 12.8000 | 1:7 | 1:31 | 1:1 | 6 |
| 136 | 12.9620 | 1:0 | 1:63 | 1:15 | 10 |
| 137 | 13.1282 | 1:1 | 1:15 | 1:31 | 9 |
| 138 | 13.1282 | 1:1 | 1:63 | 1:7 | 9 |
| 139 | 13.4737 | 1:3 | 1:15 | 1:15 | 8 |
| 140 | 13.4737 | 1:3 | 1:63 | 1:3 | 8 |
| 141 | 14.2222 | 1:7 | 1:15 | 1:7 | 7 |
| 142 | 14.2222 | 1:7 | 1:63 | 1:1 | 7 |
| 143 | 14.6286 | 1:3 | 1:15 | 1:31 | 9 |
| 144 | 15.0588 | 1:7 | 1:15 | 1:15 | 8 |
| 145 | 15.5152 | 1:7 | 1:15 | 1:31 | 9 |
| 146 | 16.0000 | 1:15 | N/A | N/A | 5 |
| 147 | 16.2540 | 1:0 | 1:31 | 1:31 | 10 |
| 148 | 16.2540 | 1:15 | 1:31 | 31:1 | 10 |
| 149 | 16.3840 | 1:15 | 1:63 | 31:1 | 11 |
| 150 | 16.5161 | 1:1 | 1:31 | 1:15 | 9 |
| 151 | 16.5161 | 1:15 | 1:31 | 15:1 | 9 |
| 152 | 16.7869 | 1:15 | 1:63 | 15:1 | 10 |
| 153 | 17.0667 | 1:3 | 1:31 | 1:7 | 8 |
| 154 | 17.0667 | 1:15 | 1:31 | 7:1 | 8 |
| 155 | 17:6552 | 1:15 | 1:63 | 7:1 | 9 |
| 156 | 18.2857 | 1:7 | 1:31 | 1:3 | 7 |
| 157 | 18.2857 | 1:15 | 1:31 | 3:1 | 7 |
| 158 | 19.6923 | 1:15 | 1:63 | 3:1 | 8 |
| 159 | 21.3333 | 1:15 | 1:31 | 1:1 | 6 |
| 160 | 21.5579 | 1:0 | 1:63 | 1:31 | 11 |
| 161 | 21.7872 | 1:1 | 1:31 | 1:31 | 10 |
| 162 | 21.7872 | 1:1 | 1:63 | 1:15 | 10 |
| 163 | 22.2609 | 1:3 | 1:31 | 1:15 | 9 |
| 164 | 22.2609 | 1:3 | 1:63 | 1:7 | 9 |
| 165 | 23.2727 | 1:7 | 1:31 | 1:7 | 8 |
| 166 | 23.2727 | 1:7 | 1:63 | 1:3 | 8 |
| 167 | 25.6000 | 1:15 | 1:31 | 1:3 | 7 |
| 168 | 25.6000 | 1:15 | 1:63 | 1:1 | 7 |
| 169 | 26.2564 | 1:3 | 1:31 | 1:31 | 10 |
| 170 | 26.9474 | 1:7 | 1:31 | 1:15 | 9 |
| 171 | 28.4444 | 1:15 | 1:31 | 1:7 | 8 |
| 172 | 29.2571 | 1:7 | 1:31 | 1:31 | 10 |
| 173 | 30.1176 | 1:15 | 1:31 | 1:15 | 9 |
| 174 | 31.0303 | 1:15 | 1:31 | 1:31 | 10 |
| 175 | 32.0000 | 1:31 | N/A | N/A | 6 |
| 176 | 32.5079 | 1:1 | 1:63 | 1:31 | 11 |
| 177 | 32.5079 | 1:31 | 1:63 | 31:1 | 11 |
| 178 | 33.0323 | 1:3 | 1:63 | 1:15 | 10 |
| 179 | 33.0323 | 1:31 | 1:63 | 15:1 | 10 |
| 180 | 34.1333 | 1:7 | 1:63 | 1:7 | 9 |
| 181 | 34.1333 | 1:31 | 1:63 | 7:1 | 9 |
| 182 | 36.5714 | 1:15 | 1:63 | 1:3 | 8 |
| 183 | 36.5714 | 1:31 | 1:63 | 3:1 | 8 |
| 184 | 42.6667 | 1:31 | 1:63 | 1:1 | 7 |
| 185 | 43.5745 | 1:3 | 1:63 | 1:31 | 11 |
| 186 | 44.5217 | 1:7 | 1:63 | 1:15 | 10 |
| 187 | 46.5455 | 1:15 | 1:63 | 1:7 | 9 |
| 188 | 51.2000 | 1:31 | 1:63 | 1:3 | 8 |
| 190 | 52.5128 | 1:7 | 1:63 | 1:31 | 11 |
| 191 | 53.8947 | 1:15 | 1:63 | 1:15 | 10 |
| 192 | 56.8889 | 1:31 | 1:63 | 1:7 | 9 |
| 193 | 58.5143 | 1:15 | 1:63 | 1:31 | 11 |
| 194 | 60.2353 | 1:31 | 1:63 | 1:15 | 10 |
| 195 | 62.0606 | 1:31 | 1:63 | 1:31 | 11 |
| 196 | 64.0000 | 1:63 | N/A | N/A | 7 |

7.6 Electrowetting-Based Droplet Actuation on a Single-Sided Electrode Array The aspects of the invention thus far have been described in connection with the use of a droplet actuating apparatus that has a two-sided electrode configuration such as microactuator mechanism 10 illustrated in FIG. 1. That is, lower plane 12 contains control or drive electrodes $E_1$-$E_3$ and upper plane 14 contains ground electrode G. As regards microactuator mechanism 10, the function of upper plane 14 is to bias droplet D at the ground potential or some other reference potential. The grounding (or biasing to reference) of upper plane 14 in connection with the selective biasing of drive electrodes $E_1$-$E_3$ of lower plane 12 generates a potential difference that enables droplet D to be moved by the step-wise electrowetting technique described herein. However, in accordance with another embodiment of the invention, the design of the apparatus employed for two-dimensional electrowetting-based droplet manipulation can be simplified and made more flexible by eliminating the need for a grounded upper plane 14.

Referring now to FIGS. 23A and 23B, a single-sided electrowetting microactuator mechanism, generally designated 500, is illustrated. Microactuator mechanism 500 comprises a lower plane 512 similar to that of mechanism 10 of FIG. 1, and thus includes a suitable substrate 521 on which two-dimensional array of closely packed drive electrodes E (e.g., drive electrodes $E_1$-$E_3$ and others) are embedded such as by patterning a conductive layer of copper, chrome, ITO, and the like. A dielectric layer 523 covers drive electrodes E. Dielectric layer 523 is hydrophobic, and/or is treated with a hydrophobic layer (not specifically shown). As a primary difference from microactuator mechanism 10 of FIG. 1, a two-dimensional grid of conducting lines G at a reference potential (e.g., conducting lines $G_1$-$G_6$ and others) has been superimposed on the electrode array of microactuator mechanism 500 of FIGS. 23A and 23B, with each conducting line G running through the gaps between adjacent drive electrodes E. The reference potential can be a ground potential, a nominal potential, or some other potential that is lower than the actuation potential applied to drive electrodes E. Each conducting line G can be a wire, bar, or any other conductive structure that has a much narrower width/length aspect ratio in relation to drive electrodes E. Each conducting line G could alternatively comprise a closely packed series of smaller electrodes, but in most cases this alternative would impractical due to the increased number of electrical connections that would be required.

Importantly, the conducting line grid is coplanar or substantially coplanar with the electrode array. The conducting line grid can be embedded on lower plane 512 by means of microfabrication processes commonly used to create conductive interconnect structures on microchips. It thus can be seen that microactuator mechanism 500 can be constructed as a single-substrate device. It is preferable, however, to include an upper plane 514 comprising a plate 525 having a hydrophobic surface 527, such as a suitable plastic sheet or a hydrophobized glass plate. Unlike microactuator mechanism 10 of FIG. 1, however, upper plane 514 of microactuator mechanism 500 of FIGS. 23A and 23B does not function as an electrode to bias droplet D. Instead, upper plane 514 functions solely as a structural component to contain droplet D and any filler fluid such as an inert gas or immiscible liquid.

In the use of microactuator mechanism 500 for electrowetting-based droplet manipulations, it is still a requirement that a ground or reference connection to droplet D be maintained essentially constantly throughout the droplet transport event. Hence, the size or volume of droplet D is selected to ensure that droplet D overlaps all adjacent drive electrodes E as well as all conducting lines G surrounding the drive electrode on which droplet D resides (e.g., electrode $E_2$ in FIG. 23B). Moreover, it is preferable that dielectric layer 523 be patterned to cover only drive electrodes E so that conducting lines C are exposed to droplet D or at least are not electrically isolated from droplet D. At the same time, however, it is preferable that conducting lines G be hydrophobic along with drive electrodes E so as not to impair movement of droplet D. Thus, in a preferred embodiment, after dielectric layer 523 is patterned, both drive electrodes E and conducting lines G are coated or otherwise treated so as render them hydrophobic. The hydrophobization of conducting lines G is not specifically shown in FIGS. 23A and 23B. It will be understood, however, that the hydrophobic layer covering conducting lines G is so thin that an electrical contact between droplet D and conducting lines G can still be maintained, due to the porosity of the hydrophobic layer.

To operate microactuator mechanism 500, a suitable voltage source V and electrical lead components are connected with conducting lines G and drive electrodes E. Because conducting lines G are disposed in the same plane as drive electrodes E, application of an electrical potential between conducting lines G and a selected one of drive electrodes $E_1$, $E_2$, or $E_3$ (with the selection being represented by switches $S_1$-$S_3$ in FIG. 23A) establishes an electric field in the region of dielectric layer 523 beneath droplet D. Analogous to the operation of microactuator mechanism 10 of FIG. 1, the electric field in turn creates a surface tension gradient to cause droplet D overlapping the energized electrode to move toward that electrode (e.g., drive electrode $E_3$ if movement is intended in right-hand direction in FIG. 23A). The electrode array can be sequenced in a predetermined manner according to a set of software instructions, or in real time in response to a suitable feedback circuit.

It will thus be noted that microactuator mechanism 500 with its single-sided electrode configuration can be used to implement all functions and methods described hereinabove in connection with the two-sided electrode configuration of FIG. 1, e.g., dispensing, transporting, merging, mixing, incubating, splitting, analyzing, monitoring, reacting, detecting, disposing, and so on to realize a miniaturized lab-on-a-chip system. For instance, to move droplet D shown in FIG. 23B to the right, drive electrodes $E_2$ and $E_3$ are activated to cause droplet D to spread onto drive electrode $E_3$. Subsequent de-activation of drive electrode $E_2$ causes droplet D to relax to a more favorable lower energy state, and droplet D becomes centered on drive electrode $E_3$. As another example, to split droplet D, drive electrodes $E_1$, $E_2$ and $E_3$ are activated to cause droplet D to spread onto drive electrodes $E_1$ and $E_3$. Drive electrode $E_2$ is then de-activated to cause droplet D to break into two droplets respectively centered on drive electrodes $E_1$ and $E_3$.

Referring now to FIGS. 24A-24D, an alternative single-sided electrode configuration is illustrated in accordance with the present invention. A base substrate containing an array of row and column biasing electrodes $E_{ij}$ is again utilized as in previously described embodiments. Referring specifically to FIG. 24A, an array or portion of an array is shown in which three rows of electrodes $E_{11}$-$E_{14}$, $E_{21}$-$E_{25}$, and $E_{31}$-$E_{34}$, respectively, are provided. The rows and columns of the electrode array can be aligned as described herein for other embodiments of the invention. Alternatively, as specifically shown in FIG. 24A, the array can be misaligned such that the electrodes in any given row are offset from the electrodes of adjacent rows. For instance, electrodes $E_{11}$-$E_{14}$ of the first row and electrodes $E_{31}$-$E_{34}$ of the third row are offset from electrodes $E_{21}$-$E_{25}$ of the intermediate second row. Whether aligned or misaligned, the electrode array is preferably covered with insulating and hydrophobic layers as in previously described embodiments. As in the configuration illustrated in FIGS. 23A and 23B, a top plate (not shown) can be provided for containment but does not function as an electrode.

In operation, selected biasing electrodes $E_{ij}$ are dynamically assigned as either driving electrodes or grounding (or reference) electrodes. To effect droplet actuation, the assignment of a given electrode as a drive electrode requires that an adjacent electrode be assigned as a ground or reference electrode to create a circuit inclusive with droplet D and thereby enable the application of an actuation voltage. In FIG. 24A, electrode $E_{21}$ is energized and thus serves as the drive electrode, and electrode $E_{22}$ is grounded or otherwise set to a reference potential. All other electrodes $E_{ij}$ of the illustrated array, or at least those electrodes surrounding the driving/reference electrode pair $E_{21}$/$E_{22}$, remain in an electrically floating state. As shown in FIG. 24A, this activation causes droplet D overlapping both electrodes $E_{21}$ and $E_{22}$ to seek an energetically favorable state by moving so as to become centered along the gap or interfacial region between electrodes $E_{21}$ and $E_{22}$.

In FIG. 24B, electrode $E_{21}$ is deactivated and electrode $E_{11}$ from an adjacent row is activated to serve as the next driving electrode. Electrode $E_{22}$ remains grounded or referenced. This causes droplet D to center itself between electrodes $E_{21}$ and $E_{22}$ by moving in a resultant northeast direction, as indicated by the arrow. As shown in FIG. 24C, droplet D is actuated to the right along the gap between the first two electrode rows by deactivating electrode $E_{11}$ and activating electrode $E_{12}$. As shown in FIG. 24D, electrode $E_{22}$ is disconnected from ground or reference and electrode $E_{23}$ is then grounded or referenced to cause droplet D to continue to advance to the right. It can be seen that additional sequencing of electrodes $E_{ij}$ to render them either driving or reference electrodes can be performed to cause droplet D to move in any direction along any desired flow path on the electrode array. It can be further seen that, unlike previously described embodiments, the flow path of droplet transport occurs along the gaps between electrodes $E_{ij}$ as opposed to along the centers of electrodes $E_{ij}$ themselves. It is also observed that the required actuation voltage will in most cases be higher as compared with the configuration shown in FIGS. 23A and 23B, because the dielectric layer covers both the driving and reference electrodes and thus its thickness is effectively doubled.

Referring now to FIGS. 25A and 25B, an electrode array with aligned rows and columns can be used to cause droplet transport in straight lines in either the north/south (FIG. 25A) or east/west (FIG. 25B) directions. The operation is analogous to that just described with reference to FIGS. 24A-24D. That is, programmable sequencing of pairs of drive and reference electrodes causes the movement of droplet D along the intended direction. In FIG. 25A, electrodes $E_{12}$, $E_{22}$ and $E_{32}$ of one column are selectively set to a ground or reference potential and electrodes $E_{13}$, $E_{23}$ and $E_{33}$ of an adjacent column are selectively energized. In FIG. 25B, electrodes $E_{11}$, $E_{12}$, $E_{13}$ and $E_{14}$ of one row are selectively energized and electrodes $E_{21}$, $E_{22}$, $E_{23}$ and $E_{24}$ of an adjacent row are selectively grounded or otherwise referenced.

It will be noted that a microactuator mechanism provided with the alternative single-sided electrode configurations illustrated in FIGS. 24A-24D and FIGS. 25A and 25B can be used to implement all functions and methods described hereinabove in connection with the two-sided electrode configuration of FIG. 1. For instance, to split droplet D in either of the alternative configurations, three or more adjacent electrodes are activated to spread droplet D and an appropriately selected intervening electrode is then de-activated to break droplet D into two droplets.

It will be understood that various details of the invention may be changed without departing from the scope of the invention. Furthermore, the foregoing description is for the purpose of illustration only, and not for the purpose of limitation—the invention being defined by the claims.

What is claimed is:

1. A binary mixing process, comprising:
   (a) providing a binary mixing apparatus for mixing two droplets comprising a first binary mixing unit,
      wherein the first binary mixing unit comprises an electrode array comprising X rows of electrodes and X columns of electrodes to form an electrode array consisting of $X^2$ matrix electrodes and associated cells $EA_{ij}$ where $i$ is a positive integer that designates 1, 2, . . . X rows of electrodes, and where $j$ is a positive integer that designates 1, 2, . . . X columns of electrodes,
      wherein the first binary mixing unit comprises a logic cell matrix comprising a subset of the rows and columns of the electrode array consisting of matrix electrodes and associated cells $EA_{ij}$ in which $i$ and $j$ are both odd integers, and each cell of the logic cell matrix is capable of storing one of a sample droplet, a reagent droplet or an intermediate-mixture droplet,
      wherein electrodes situated in rows of the electrode array consisting of matrix electrodes and associated cells $EA_{ij}$ in which $i$ is an even integer comprise electrodes on which merging and/or splitting of the sample droplet, the reagent droplet, and/or the intermediate-mixture droplet occurs, and
      wherein electrodes situated in columns of the electrode array consisting of matrix electrodes and associated cells $EA_{ij}$ in which $j$ is an even integer comprise electrodes on which transport of the sample droplet, the reagent droplet, or the intermediate-mixture droplet occurs; and
   (b) using the binary mixing apparatus to perform a first mixing phase comprising a row mix, a column mix, or a combination of a series of row mixes and/or column mixes of a sample droplet, a reagent droplet, and/or an intermediate-mixture droplet and to dilute the concentration of the sample droplet to a desired ratio in a series of ratios selected from the group consisting of 1:1, 1:3, 1:7 . . . 1:$2^{n-1}$, wherein n is a positive integer equal to the number of mixing operations performed.

2. The process of claim 1, wherein the binary mixing apparatus further comprises a second binary mixing unit, and a buffer in fluid communication with the first and second binary mixing units to store intermediate products and transfer intermediate products between the first and second binary mixing units.

3. The process of claim 2, wherein the second binary mixing unit comprises an electrode array comprising X rows of electrodes and X columns of electrodes to form an electrode array consisting of $X^2$ matrix electrodes and associated cells $EA_{ij}$ where $i$ is a positive integer that designates 1, 2, . . . X rows of electrodes, and where $j$ is a positive integer that designates 1, 2, . . . X columns of electrodes,
   wherein the second binary mixing unit comprises a logic cell matrix comprising a subset of the rows and columns of the electrode array consisting of matrix electrodes and associated cells $EA_{ij}$ in which $i$ and $j$ are both odd integers, and each cell of the logic cell matrix is capable of storing one of a sample droplet, a reagent droplet, or an intermediate-mixture droplet,
   wherein electrodes situated in rows of the electrode array consisting of matrix electrodes and associated cells $EA_{ij}$ in which $i$ is an even integer comprise electrodes on which merging and/or splitting of the sample droplet, the reagent droplet, and/or the intermediate-mixture droplet occurs, and
   wherein electrodes situated in columns of the electrode array consisting of matrix electrodes and associated cells $EA_{ij}$ in which $j$ is an even integer comprise electrodes on which transport of the sample droplet, the reagent droplet, or the intermediate-mixture droplet occurs.

4. The process of claim 3, wherein the binary mixing apparatus further comprises a microprocessor capable of executing the instructions of a computer program in communication with the first binary mixing unit, second binary mixing unit, and buffer through one or more communication lines.

5. The process of claim 4, wherein the binary mixing apparatus further comprises electrode containing droplet-handling regions for each mixing unit which can be sequentially activated to implement one or more mixing operations selected from the group consisting of droplet discarding, droplet merging, droplet splitting, and combinations thereof.

6. The process of claim 5, wherein first and second binary mixing units are capable of producing a volume of droplets that is equivalent to the number of associated cells in each of the respective logic cell matrices.

7. The process of claim 6, wherein the first and second binary mixing units further comprise a sample reservoir, a waste reservoir, and a reagent reservoir in fluid communication with the electrode array.

8. The process of claim 7, wherein the first and second binary mixing units comprises a plurality of transport electrodes and associated cells for transporting droplets to and from the electrode array.

9. The process of claim 8, wherein the first binary mixing unit comprises a plurality of electrical leads connected to matrix electrodes $EA_{ij}$ and the transport electrodes to control the movement or manipulation of droplets.

10. The process of claim 9, wherein the binary mixing apparatus is fabricated on a microfluidic chip.

11. The process of claims 1 or 10, wherein the first and/or second binary mixing units comprise a 7×7 electrode array consisting of 49 matrix electrodes and associated cells $EA_{ij}$, where $i$ designates 1, 2, . . . , 7 rows of electrodes and $j$ designates 1, 2, . . . , 7 columns of electrodes.

12. The process of claim 11, wherein the binary mixing apparatus is used to perform a first single row mix by combining a sample droplet $S_1$ having a concentration of 1 with a reagent droplet $R_1$ having a concentration of 0 to produce two intermediate-mixture droplets $I_1$ and $I_2$, each intermediate-mixture droplet having ½ of the concentration of sample droplet $S_1$.

13. The process of claim 12, further comprising discarding at least one of intermediate-mixture droplets $I_1$ or $I_2$, and transporting a second reagent droplet $R_2$ having a concentration of 0 to a logic cell in the same column as, and adjacent to, the remaining intermediate-mixture droplet $I_1$ or $I_2$.

14. The process of claim 13, further comprising using the binary mixing apparatus to perform a second single row mix by combining the remaining intermediate-mixture droplet $I_1$ or $I_2$ and the second reagent droplet $R_2$ to produce two intermediate-mixture droplets $I_3$ or $I_4$, each intermediate-mixture droplet having ¼ of the concentration of sample droplet $S_1$.

15. The process of claim 14, further comprising transporting a third reagent droplet $R_3$ and a fourth reagent droplet $R_4$, each having a concentration of 0, to logic cells in the same column as, and adjacent to, the intermediate-mixture droplets $I_3$ and $I_4$.

16. The process of claim 15, further comprising using the binary mixing apparatus to perform a double row mixing operation by combining the intermediate-mixture droplets $I_3$ and $I_4$ with the respective reagent droplets $R_3$ and $R_4$ to produce four intermediate-mixture droplets $I_5$, $I_6$, $I_7$, and $I_8$, each intermediate-mixture droplet having ⅛ of the concentration of sample droplet $S_1$.

17. The process of claim 16, further comprising transporting a fifth reagent droplet $R_5$, a sixth reagent droplet $R_6$, a seventh reagent droplet $R_7$, and an eighth reagent droplet $R_8$, each having a concentration of 0, to logic cells in a different column than, and adjacent to, the intermediate-mixture droplets $I_5$, $I_6$, $I_7$, and $I_8$.

18. The process of claim 17, further comprising using the binary mixing apparatus to perform a first column mix operation between each corresponding pair of intermediate-mixture droplets $I_5$, $I_6$, $I_7$, and $I_8$ and reagent droplets $R_5$, $R_6$, $R_7$, and $R_8$ to produce eight intermediate-mixture droplets $I_9$, $I_{10}$, $I_{11}$, $I_{12}$, $I_{13}$, $I_{14}$, $I_{15}$ and $I_{16}$, each having 1/16 of the concentration of sample droplet $S_1$, wherein intermediate-mixture droplets $I_9$, $I_{10}$, $I_{11}$, and $I_{12}$ are produced in a first column of the logic cell matrix, and intermediate-mixture droplets $I_{13}$, $I_{14}$, $I_{15}$ and $I_{16}$ are produced in a second column of the logic cell matrix.

19. The process of claim 18, further comprising transporting each intermediate-mixture droplet in the first and second columns of the logic cell matrix to the next adjacent column to the right in the logic cell matrix.

20. The process of claim 19, further comprising transporting four reagent droplets $R_9$, $R_{10}$, $R_{11}$ and $R_{12}$, each having a concentration of 0, to a column in the logic cell matrix that is adjacent to corresponding intermediate-mixture droplets $I_9$, $I_{10}$, $I_{11}$, and $I_{12}$, and transporting four reagent droplets $R_{13}$, $R_{14}$, $R_{15}$, and $R_{16}$, each having a concentration of 0, to a column in the logic cell matrix that is adjacent to corresponding intermediate-mixture droplets $I_{13}$, $I_{14}$, $I_{15}$, and $I_{16}$.

21. The process of claim 19, further comprising using the binary mixing apparatus to perform a double column mix operation between each corresponding pair of intermediate-mixture droplets $I_9$, $I_{10}$, $I_{11}$, $I_{12}$ and reagent droplets $R_{13}$, $R_{14}$, $R_{15}$, and $R_{16}$ and each corresponding pair of intermediate-mixture droplets $I_{13}$, $I_{14}$, $I_{15}$, and $I_{16}$ and reagent droplets $R_{13}$, $R_{14}$, $R_{15}$, and $R_{16}$ to produce sixteen final-mixture product droplets $P_1$, $P_2$, $P_3$, $P_4$, $P_5$, $P_6$, $P_7$, $P_8$, $P_9$, $P_{10}$, $P_{11}$, $P_{12}$, $P_{13}$, $P_{14}$, $P_{15}$ and $P_{16}$, each having 1/32 of the concentration of sample droplet $S_1$.

22. The process of claim 21, wherein the product droplets $P_1$-$P_{16}$ are used for sampling, detection, and/or analysis.

23. The process of claim 22, further comprising using the binary mixing apparatus to perform a second mixing phase comprising a row mix, a column mix, or a combination of a series of row mixes and/or column mixes of a sample droplet, a reagent droplet, and/or an intermediate-mixture droplet and to dilute the concentration of the sample droplet to a desired ratio in a series of ratios selected from the group consisting of 1:1, 1:3, 1:7 . . . 1:$2^{n-1}$, wherein n is a positive integer equal to the number of mixing operations performed.

24. The process of claim 23, wherein the second mixing phase is performed using the second binary mixing unit in parallel to, and independent of, the first mixing phase using the first binary mixing unit.

25. The process of claim 24, further comprising performing an additional mixing phase using products from a previous mixing phase to calibrate a mixing ratio for increased accuracy.

26. The process of claim 22, wherein the first binary mixing unit comprises a first surface area and the array of electrodes comprises a first array of electrodes disposed in at least a substantially co-planar relation on the first surface area, wherein the first array of electrodes comprises first drive electrodes and dedicated first reference electrodes.

27. The process of claim 26, wherein the binary mixing apparatus further comprises an electrode selector for dynamically creating a sequence of first electrode pairs on the first surface area, each first electrode pair comprising a selected first electrode pair comprising a selected first drive electrode biased to a first voltage and a selected first reference electrode biased to a second voltage less than the first voltage.

28. The process of claim 27, wherein the second binary mixing unit comprises a second surface area and the array of electrodes comprises a second array of electrodes disposed in at least a substantially co-planar relation on the second surface area, and a droplet outlet area communicating with the second surface area and with the first mixing unit, wherein the second array of electrodes comprises second drive electrodes and dedicated second reference electrodes.

29. The process of claim 28, wherein the electrode selector dynamically creates a sequence of second electrode pairs on the second surface area, each second electrode pair comprising a selected second drive electrode biased to a third voltage and a selected second reference electrode biased to a fourth voltage less than the third voltage.

30. The process of claim 29, wherein the electrode selector sequentially activates and de-activates one or more selected first drive electrodes to mix together two droplets supplied to the first surface area.

31. The process of claim 30, wherein the electrode selector sequentially activates and de-activates one or more selected second drive electrodes to mix together two other droplets supplied to the second surface area.

32. The process of claim 31, wherein mixing of the two droplets supplied to the first surface area is accomplished by electrowetting actuation wherein the droplets overlap a selected first drive electrode biased to a first voltage and a selected first reference electrode biased to a second voltage continuously.

33. The process of claim 32, wherein mixing of the two droplets supplied to the second surface area is accomplished by electrowetting actuation wherein the droplets overlap a selected second drive electrode biased to a second voltage and a selected second reference electrode biased to a second voltage continuously.

34. The process of claim 1, wherein the binary mixing apparatus further comprises:
(a) a substrate comprising a substrate surface;
(b) the electrode array, wherein the X rows of electrodes and X columns of electrodes comprise drive electrodes disposed on the substrate surface;
(c) a dedicated array of reference elements settable to a common reference potential and disposed in at least substantially co-planar relation to the electrode array, wherein the array of reference elements is electrically and physically distinct from the drive electrode array and further wherein each drive electrode is adjacent to at least one of the reference elements;
(d) a dielectric layer disposed on the substrate surface to cover the drive electrodes; and
(e) an electrode selector for sequentially activating and de-activating one or more selected drive electrodes of the array to sequentially bias the selected drive electrodes to an actuation voltage, whereby a droplet disposed on the substrate surface moves along a desired path defined by the selected drive electrodes.

35. The process according to claim 34, wherein the binary mixing apparatus further comprises a plate spaced from the substrate surface by a distance to define a space between the plate and the substrate surface, wherein the distance is sufficient to contain a droplet disposed in the space.

36. The process according to claim 35, wherein the plate comprises a plate surface facing the substrate surface, and the plate surface is hydrophobic.

37. The process according to claim 35, wherein the binary mixing apparatus further comprises a filler fluid disposed in the space.

38. The process according to claim 34, wherein at least outer portions of the drive electrodes and the reference elements are respectively hydrophobized.

39. The process according to claim 34, wherein the binary mixing apparatus further comprises a hydrophobic film disposed on the drive electrodes and the reference elements.

40. The process according to claim 34, wherein the array of reference elements comprises a grid of elongate structures.

41. The process according to claim 34, wherein the reference elements are set to a reference voltage less than the actuation voltage.

42. The process according to claim 34, wherein the reference elements are set to ground potential.

43. The process according to claim 34, wherein at least a portion of the dielectric layer is hydrophobic.

44. The process according to claim 34, wherein the electrode selector comprises an electronic processor.

45. The process according to claim 34, wherein the binary mixing apparatus further comprises a droplet inlet communicating with the substrate surface.

46. The process according to claim 45, wherein the binary mixing apparatus further comprises a droplet outlet communicating with the substrate surface.

* * * * *